United States Patent
Liu et al.

(10) Patent No.: US 11,885,800 B2
(45) Date of Patent: Jan. 30, 2024

(54) METHOD AND SYSTEM FOR DETECTING ANALYTE OF INTEREST USING MAGNETIC FIELD SENSOR AND MAGNETIC PARTICLES

(71) Applicant: IMRA America, Inc., Ann Arbor, MI (US)

(72) Inventors: Bing Liu, Ann Arbor, MI (US); Matthew L. Elani, Ann Arbor, MI (US); Alison R. Garrett, Ann Arbor, MI (US)

(73) Assignee: IMRA America, Inc., Ann Arbor, MI (US)

( * ) Notice: Subject to any disclaimer, the term of this patent is extended or adjusted under 35 U.S.C. 154(b) by 377 days.

(21) Appl. No.: 17/037,162

(22) Filed: Sep. 29, 2020

(65) Prior Publication Data
US 2022/0178919 A1    Jun. 9, 2022

Related U.S. Application Data

(60) Provisional application No. 62/916,995, filed on Oct. 18, 2019.

(51) Int. Cl.
*G01N 33/543* (2006.01)
*G01N 27/74* (2006.01)
(Continued)

(52) U.S. Cl.
CPC ..... *G01N 33/54333* (2013.01); *G01N 27/745* (2013.01); *G01N 33/54326* (2013.01);
(Continued)

(58) Field of Classification Search
CPC .......... G01N 33/54326; G01N 35/0098; B01L 2200/025
(Continued)

(56) References Cited

U.S. PATENT DOCUMENTS 5,981,297 A    11/1999 Baselt
6,437,563 B1    8/2002 Simmonds et al.
(Continued)

FOREIGN PATENT DOCUMENTS

EP    1552306    6/2008
WO    WO 2008/071820    6/2008
(Continued)

OTHER PUBLICATIONS

Marquina et al. GMR sensors and magnetic nanoparticles for immuno-chromatographic assays, Journal of Magnetism and Magnetic Materials, vol. 324, Issue 21, 2012, pp. 3495-3498 (Year: 2012).*

(Continued)

*Primary Examiner* — Christopher L Chin
(74) *Attorney, Agent, or Firm* — Knobbe, Martens, Olson & Bear, LLP

(57) ABSTRACT

A system includes an apparatus having at least one permanent magnet and at least one magnetic field sensor at a pole of the at least one permanent magnet and configured to be positioned relative to a surface of a membrane containing immobilized magnetic particles selectively bound to an analyte such that the magnetic particles are magnetized by the at least one permanent magnet. The system further includes a stage configured to move at least one of the apparatus and the membrane relative to one another with an oscillatory movement parallel to the surface of the membrane, at least one controller configured to control the oscillatory movement, and a data acquisition unit configured to receive signals from the at least one magnetic field sensor and the at least one controller method.

17 Claims, 41 Drawing Sheets

(51) Int. Cl.
  *G01N 33/68* (2006.01)
  *G01N 33/76* (2006.01)
  *G01N 35/00* (2006.01)

(52) U.S. Cl.
  CPC ......... *G01N 33/6887* (2013.01); *G01N 33/76* (2013.01); *B01L 2200/025* (2013.01); *G01N 35/0098* (2013.01)

(58) Field of Classification Search
  USPC ....................................... 436/526; 435/286.2
  See application file for complete search history.

(56) References Cited

U.S. PATENT DOCUMENTS

| | | | |
|---|---|---|---|
| 6,607,922 | B2 | 8/2003 | LaBorde |
| 6,995,021 | B2 | 2/2006 | Laitinen et al. |
| 8,026,716 | B2 | 9/2011 | Mäkiranta et al. |
| 9,488,585 | B2 | 11/2016 | Emeric et al. |
| 9,863,939 | B2 | 1/2018 | Wang et al. |
| 2001/0052769 | A1* | 12/2001 | Simmonds ........... G01N 27/745 324/204 |
| 2005/0287590 | A1* | 12/2005 | Matson ............ G01N 33/54353 435/7.1 |
| 2011/0192450 | A1 | 8/2011 | Liu et al. |
| 2014/0084902 | A1* | 3/2014 | Baikie .................. G01N 27/002 324/97 |
| 2018/0046892 | A1* | 2/2018 | Hyde ....................... A61B 5/00 |
| 2018/0106873 | A1* | 4/2018 | Wu ....................... G01R 33/093 |
| 2019/0316170 | A1* | 10/2019 | Kudo ................ G01N 21/6456 |

FOREIGN PATENT DOCUMENTS

| | | |
|---|---|---|
| WO | WO 2014/160844 | 10/2014 |
| WO | WO 2018/022776 | 2/2018 |

OTHER PUBLICATIONS

Barnett et al., "An Inexpensive, Fast and Sensitive Quantitative Lateral Flow Magneto-Immunoassay for Total Prostate Specific Antigen," Biosensors, vol. 4, pp. 204-220 (2014).

Coffey et al., "On the Theory of Debye and Neel Relaxation of Single Domain Ferromagnetic Particles," Adv. Chem. Phys., vol. LXXXIII, pp. 263-464 (1993).

Fischer et al., "Brownian Relaxation of Magnetic Colloids," J. Mag. and Mag. Mat'ls, vol. 289, pp. 74-77 (2005).

Gijs, Martin A.M., "Magnetic bead handling on-chip: new opportunities for analytical applications," Microfluid Nanofluid, vol. 1, pp. 22-40 (2004).

Lei et al., Contactless Measurement of Magnetic Nanoparticles on Lateral Flow Strips Using Tunneling Magnetoresistance (TMR) Sensors in Differential Configuration, Sensors, vol. 16, p. 2130 (2016).

Miller et al., "A DNA array sensor utilizing magnetic microbeads and magnetoelectronic detection," J. Mag. and Mag. Mat'ls, vol. 225, pp. 138-144 (2001).

Park, Jongwon, "A giant magnetoresistive reader platform for quantitative lateral flow immunoassays," Sensors and Actuators A, vol. 250, pp. 55-59 (2016).

Park, Jongwon, "Superparamagnetic nanoparticle quantification using a giant magnetoresistive sensor and permanent magnets," J. Mag. and Mag. Mat'ls, vol. 389, pp. 56-60 (2015).

Tamanaha et al., "Magnetic labeling, detection, and system integration," Biosensors and Bioelectronics, vol. 24, pp. 1-13 (2008).

Yang et al., "Detection platforms for point-of-care testing based on colorimetric, luminescent and magnetic assays: A review," Talanta, vol. 202, pp. 96-110 (2019).

* cited by examiner

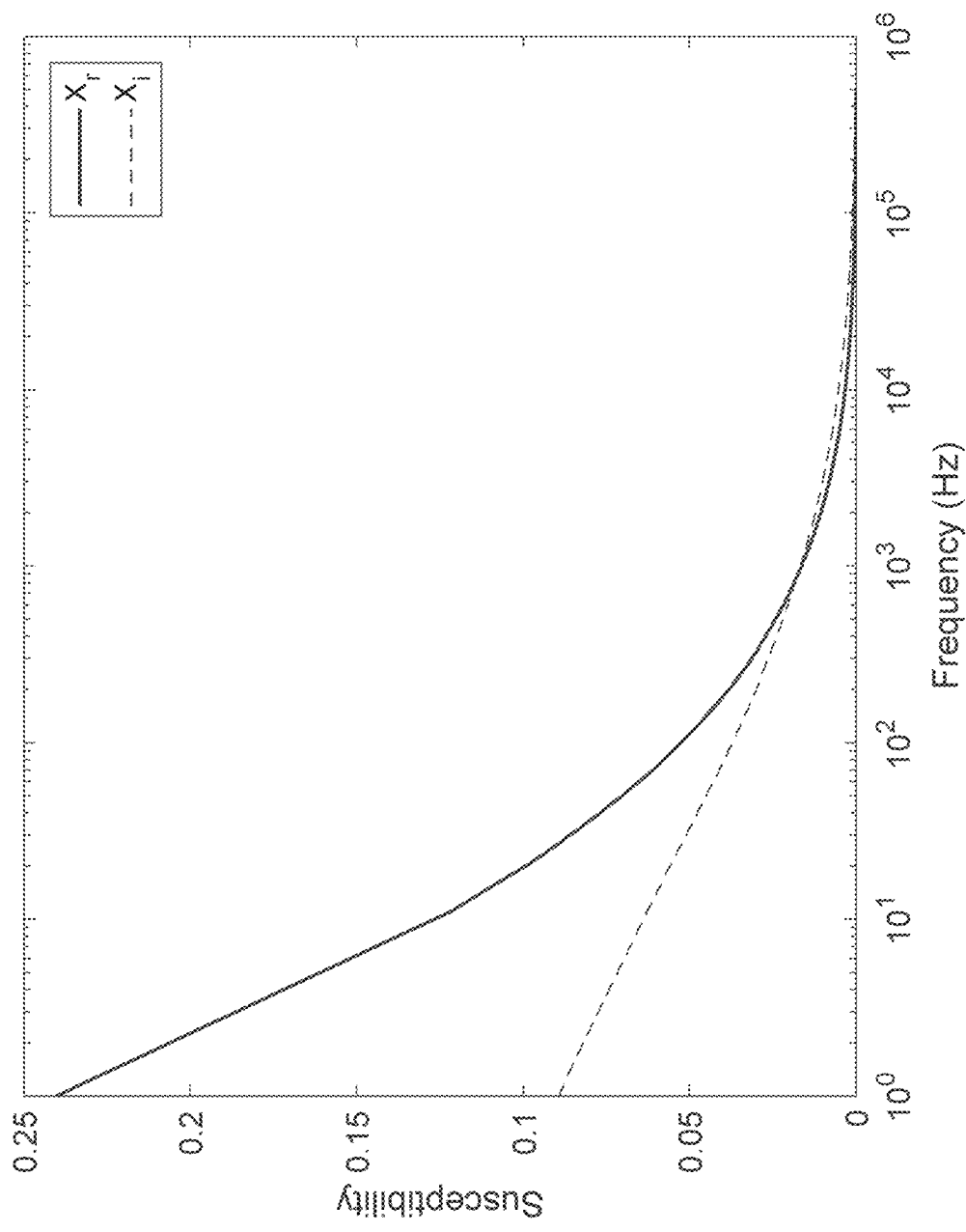

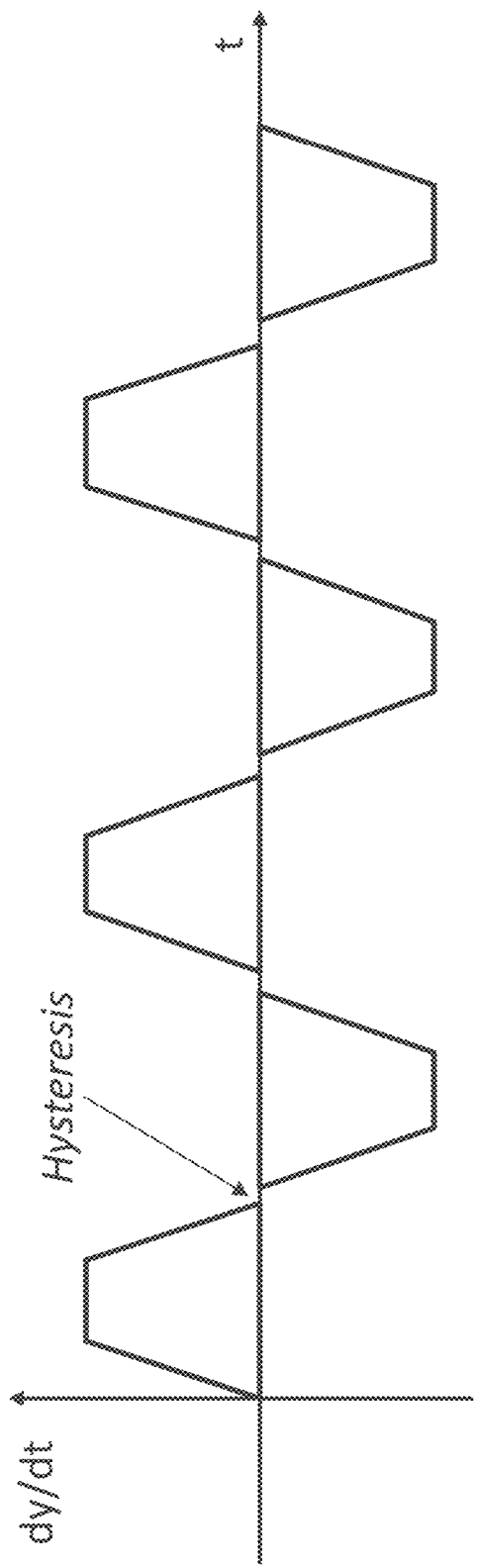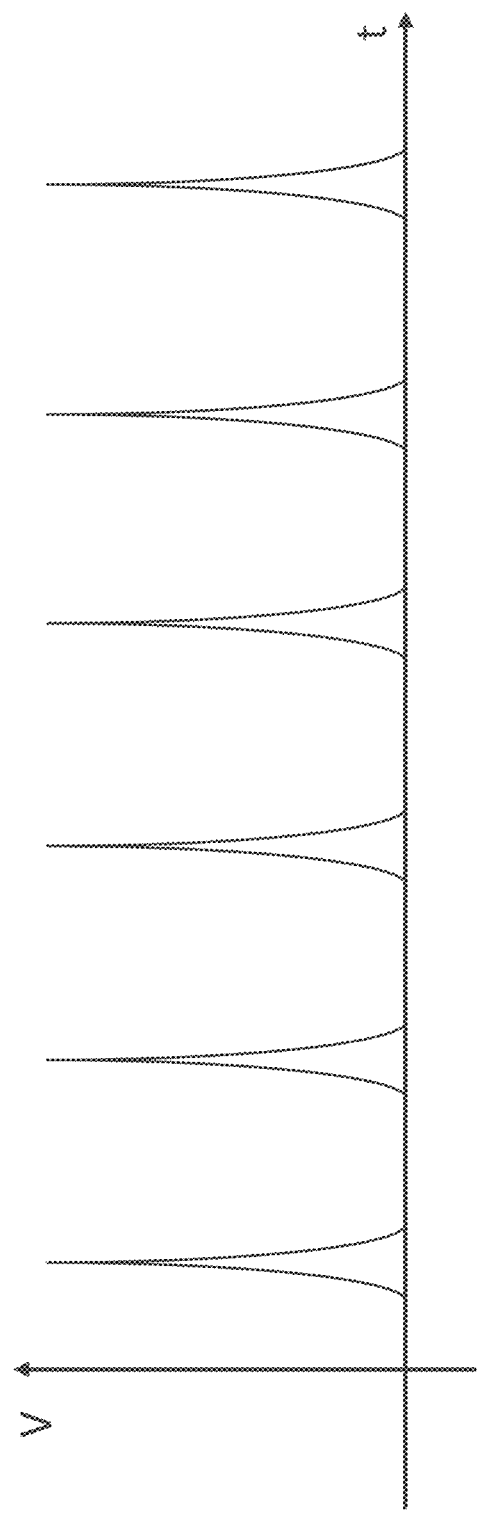
FIG. 7A: dv/dt
FIG. 7B: V

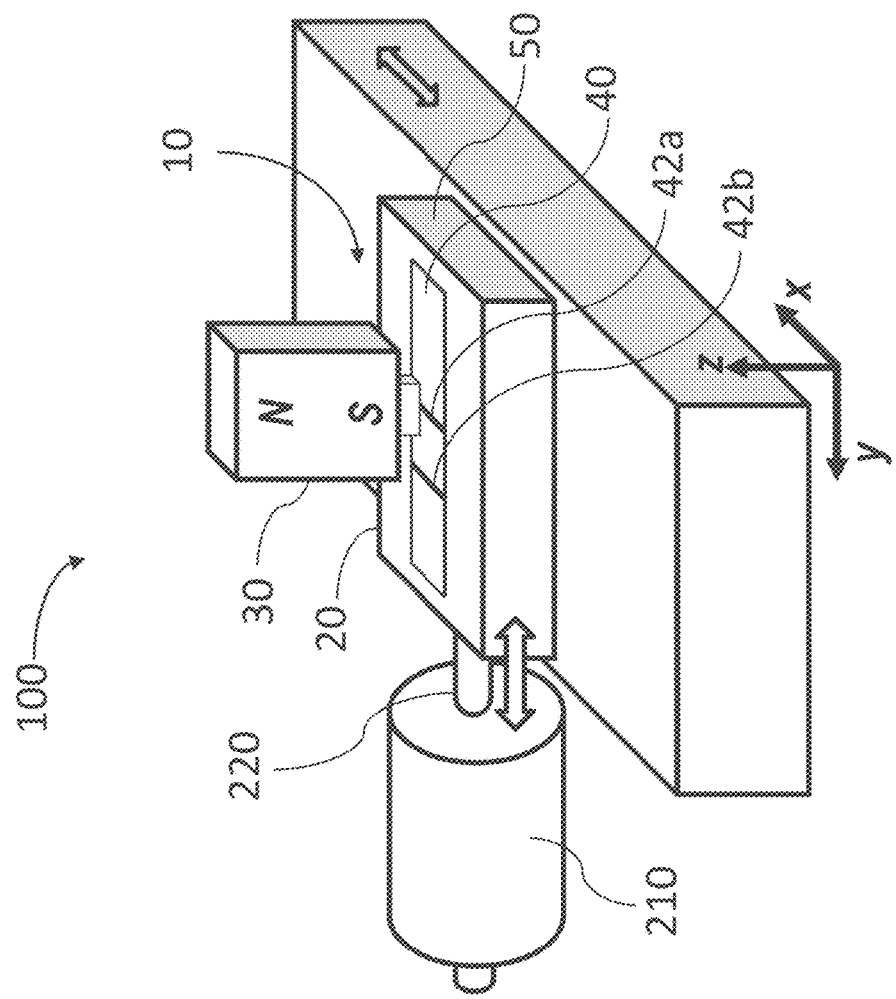
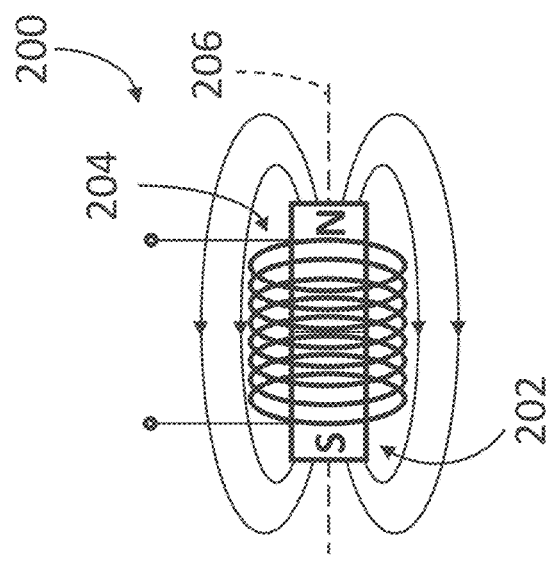
FIG. 19A
FIG. 19B

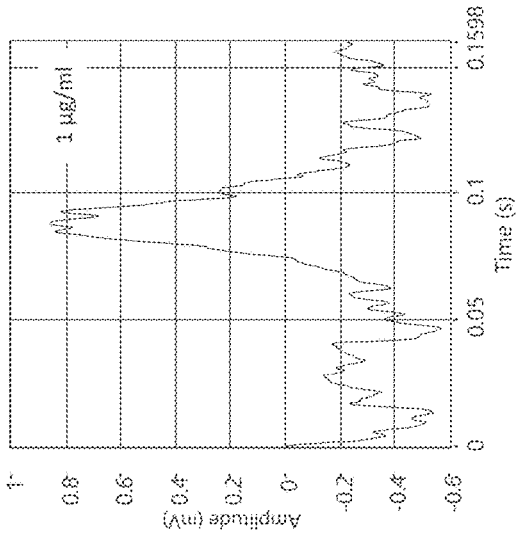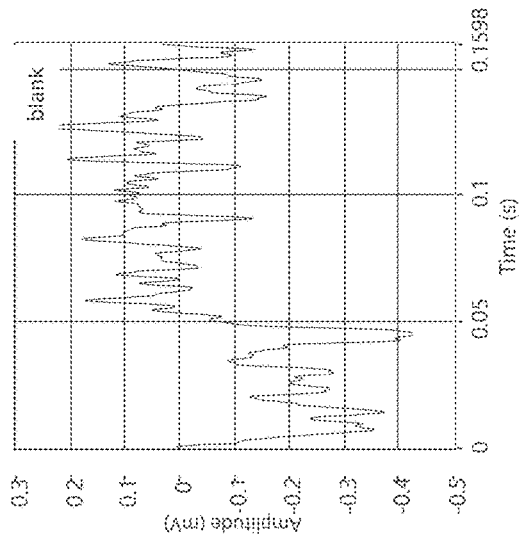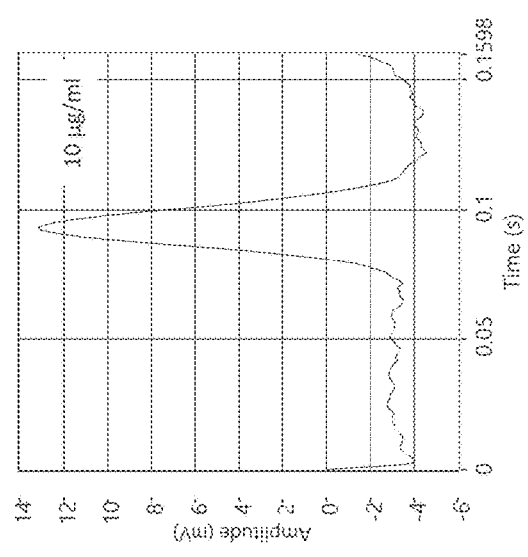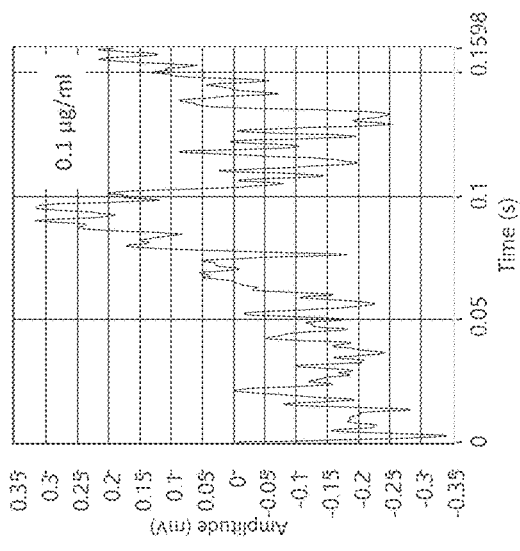

US 11,885,800 B2

METHOD AND SYSTEM FOR DETECTING ANALYTE OF INTEREST USING MAGNETIC FIELD SENSOR AND MAGNETIC PARTICLES

CLAIM OF PRIORITY

This application claims the benefit of priority to U.S. Provisional Appl. No. 62/916,995 filed on Oct. 18, 2019 and incorporated in its entirety by reference herein.

BACKGROUND

Field

This application relates generally to magnetic sensing and reader systems of biological assays using magnetic particles as probes.

Description of the Related Art

Biological binding assays, such as immunoassays and DNA hybridization assays, use either fluorescent molecules or solid particles as probes (e.g., signal reporter). The detection molecules (e.g., antibody or detection DNA) are first labeled with fluorescent molecules or solid particles, in a process also known as conjugation. Upon specific recognition and binding with antigen molecules, the probes are immobilized on a solid surface by the complementary capturing molecules (e.g., capture antibody or DNA). The assay results are obtained by measuring the fluorescence intensity of the bound fluorescent molecules or the color intensity of the bound solid particles.

The dominant fluorescence assay in diagnostics is the Enzyme-Linked Immunosorbent Assay (ELISA). The dominant solid particle-based assay is lateral flow assay (LFA), where gold nanoparticles are most commonly used due to their intense red color. ELISA has the advantage of high sensitivity but requires extensive technical training and controlled laboratories. Lateral flow assay is rapid, user-friendly, and very low-cost. Lateral flow assay can be constructed with low-cost materials such as nitrocellulose membranes for capillary flow of liquid sample, plastic backing card, fiber glass sample pad and liquid wick pad. However, lateral flow assays generally lack high sensitivity and quantitative results.

SUMMARY

In certain implementations, a method and system are provided for rapid and precise quantification of the concentration of molecules of interest. In certain implementations, the method and system provide a read out of the magnetic induction field intensity in the reaction zones (e.g., test line and control line) in a lateral flow assay using magnetic particles as the probe.

In certain implementations, an assembly comprises at least one magnetic (e.g., magnetoresistance) field sensor and at least one permanent magnet, the at least one magnetic field sensor attached to a pole of the at least one permanent magnet. The assembly is configured to be positioned such that the at least one magnetic field sensor is above a surface of a lateral flow membrane containing immobilized magnetic particles (e.g., such that the surface of the membrane is in close proximity to a surface of the at least one magnetic field sensor). In certain implementations, at least one of the assembly and the membrane is configured to be moved relative to the other with a periodic oscillatory mechanical movement (e.g., the membrane is moved relative to the assembly while the assembly is stationary; the assembly is moved relative to the membrane while the membrane remains stationary). The periodic oscillatory mechanical movement is in a direction that is substantially perpendicular to a test line and control line of the membrane, and has an amplitude that is at least twice a width of the test line and control line. In certain implementations, the periodic oscillatory mechanical movement has a frequency that does not cause significant mechanical hysteresis (e.g., time lag) of the oscillatory motion (e.g., does not cause motion instability that affects timing precision).

In certain implementations, the movement is provided by a mechanical motion stage (e.g., a stage comprising at least one piezoelectric actuator and/or at least one voice coil actuator). In certain implementations, a periodic trigger signal (e.g., electronic signal) is generated in synchronization with the periodic oscillatory mechanical movement and the trigger signal is supplied to a data acquisition (DAQ) unit to synchronize acquisition and time averaging of the magnetic field sensor signal with the movement.

In certain implementations, at least one of the assembly and the membrane are configured to be moved relative to the other with at least one second linear mechanical movement (e.g., the mechanical motion stage is configured to move the membrane for scanning the assembly in a direction along the test line and control line). For example, the at least one second linear mechanical movement can be in two substantially perpendicular directions (e.g., x-y motion) configured to provide a two-dimensional (2D) magnetic mapping of the test line and control line. The intensity of the sensor signal obtained during the 2D mapping can be summed along the test line and control line to provide a one-dimensional (1D) profile of the magnetic particle distribution in a direction substantially perpendicular to the test line and control line.

In certain implementations, the at least one magnetic field sensor comprises a Wheatstone bridge comprising four magnetoresistance sensors. In certain implementations, the Wheatstone bridge has a size that is smaller than a width of the test and control line (e.g., a size sufficiently small to provide 2D spatial resolution in lateral flow assay magnetic mapping).

In certain implementations, the membrane is held by a cassette and a position sensor (e.g., mechanical pressure sensor; proximity sensor) is positioned relative to (e.g., on, near, inside, below, or beneath) the membrane and/or the cassette, the position sensor indicative of a contact or a distance between the membrane and the at least one magnetic field sensor. A sensor signal generated by the position sensor (e.g., a signal indicative of a pressure applied by the cassette to the mechanical pressure sensor) is configured to be supplied as a feedback signal to a third linear actuator providing vertical movement (e.g., in a direction that is substantially perpendicular to a plane of the membrane), the third linear actuator configured to use the feedback signal to keep the distance between the membrane and the at least one magnetic field sensor substantially constant.

In certain implementations, a combined system and a lateral flow assay are configured to determine a presence and/or absence of one or more target analytes in a sample (e.g., to semi-quantitatively or to quantitatively determine an amount of at least one target analyte in a sample). Examples of target analytes compatible with certain implementations described herein include but are not limited to: biomarkers (e.g., antibodies to an infectious disease, cancer biomarkers, other indicators including proteins, peptides, nucleic acids, and polysaccharides); infectious disease agents (e.g., viruses, bacteria, molds); drugs of abuse. Samples compatible with certain implementations described herein can be biologically derived (e.g., from humans, animals, plants, fungi, yeast, or bacteria), or may be derived from food, water, soil, air, or other sources (e.g., to test for contamination). In certain implementations, the magnetic probe in this system advantageously enables analyte detection at concentrations that are at least one order of magnitude lower than concentrations that can be detected using a lateral flow assay based on optical sensing. Such increased sensitivity can be highly valuable in a number of fields, including but not limited to: point-of-care testing; food safety; animal health; other fields in which it is advantageous to quickly identify the presence and/or amount of a target analyte with a high degree of accuracy. Certain implementations described herein are configured to be readily integrated with existing lateral flow assays by exchanging the optical probe particles (e.g., gold nanoparticles) with magnetic particles (e.g., iron oxide nanoparticles).

BRIEF DESCRIPTION OF THE DRAWINGS

FIGS. 6A-6C are plots of theoretical calculations of the magnetic AC susceptibility of iron oxide nanoparticles as a function of frequency for particles of different sizes, assuming Gaussian distributions with $\sigma=2$ nm.

FIG. 7A schematically illustrates an example trapezoidal speed profile of a closed loop oscillation system with some hysteresis (e.g., time lag) at zero speed where the motion reverses direction in accordance with certain implementations described herein.

FIG. 7B schematically illustrates an example train of magnetic field sensor signals in accordance with certain implementations described herein in which the test line passes the sensor at the peak velocity of the oscillation.

FIGS. 19A-19B schematically illustrates an example voice coil linear actuator and an example system utilizing the voice coil linear actuator, respectively, in accordance with certain implementations described herein.

FIGS. 24A-24D show example measurements using a magnetic field sensor positioned beneath a series of membranes in accordance with certain implementations described herein.

The figures depict various implementations of the present disclosure for purposes of illustration and are not intended to be limiting. Wherever practicable, similar or like reference numbers or reference labels may be used in the figures and may indicate similar or like functionality.

DETAILED DESCRIPTION

Overview

Detection based on magnetic field sensing and magnetic particles as probes for lateral flow and other form of assays (e.g., in situ assays where a sensor is submerged in a sample) can provide several advantages compared with colorimetric detection of gold nanoparticles. For example, magnetic sensing is free of optical interference and can be applied to a wide variety of sample forms such as whole blood, solid samples, and unprocessed water samples.

Magnetic sensing also has the potential of improving sensitivity in lateral flow assay (e.g., on the order of picograms to nanograms per milliliter). In traditional colorimetric detection in lateral flow assay, the signal is based on color intensity generated by gold nanoparticles. In the reaction zone (e.g., test line and control line), where the gold nanoparticles are captured upon specific recognition and binding, only those particles in the top layer of the nitrocellulose membrane contribute to the color signal, as the light coming from the particles residing below the membrane surface are heavily scattered by the porous structure of the membrane. With magnetic detection, the signal generated by the magnetic particles residing in the whole depth of the reaction zones can be detected without scattering loss.

Lacking quantification (e.g., capability to differentiate at least between logarithmic steps; e.g., between 1, 0.1, 0.01 ng/ml, etc.) in lateral flow assay has been an obstacle to full realization of the potential of this technology. Magnetic sensing can help improve assay quantification, e.g., by providing sensitivity at depth below the surface of the test line, and by scanning and integrating along the test line, such that the entire population of the magnetic particles captured at the test line can be measured.

Applying magnetic sensing to biological assays presents various challenges. For example, the signals come from small magnetic particles (e.g., in lateral flow assays, the particle size is limited by the pores of nitrocellulose membrane to below 200 nm). Because the strength of magnetic induction of a point source follows an inverse quadratic law with distance, the signal drops quickly with increasing distance of the magnetic field sensor from the source, so the magnetic field sensor is to be positioned very close to the membrane where accessible space is limited.

Figure 1A:
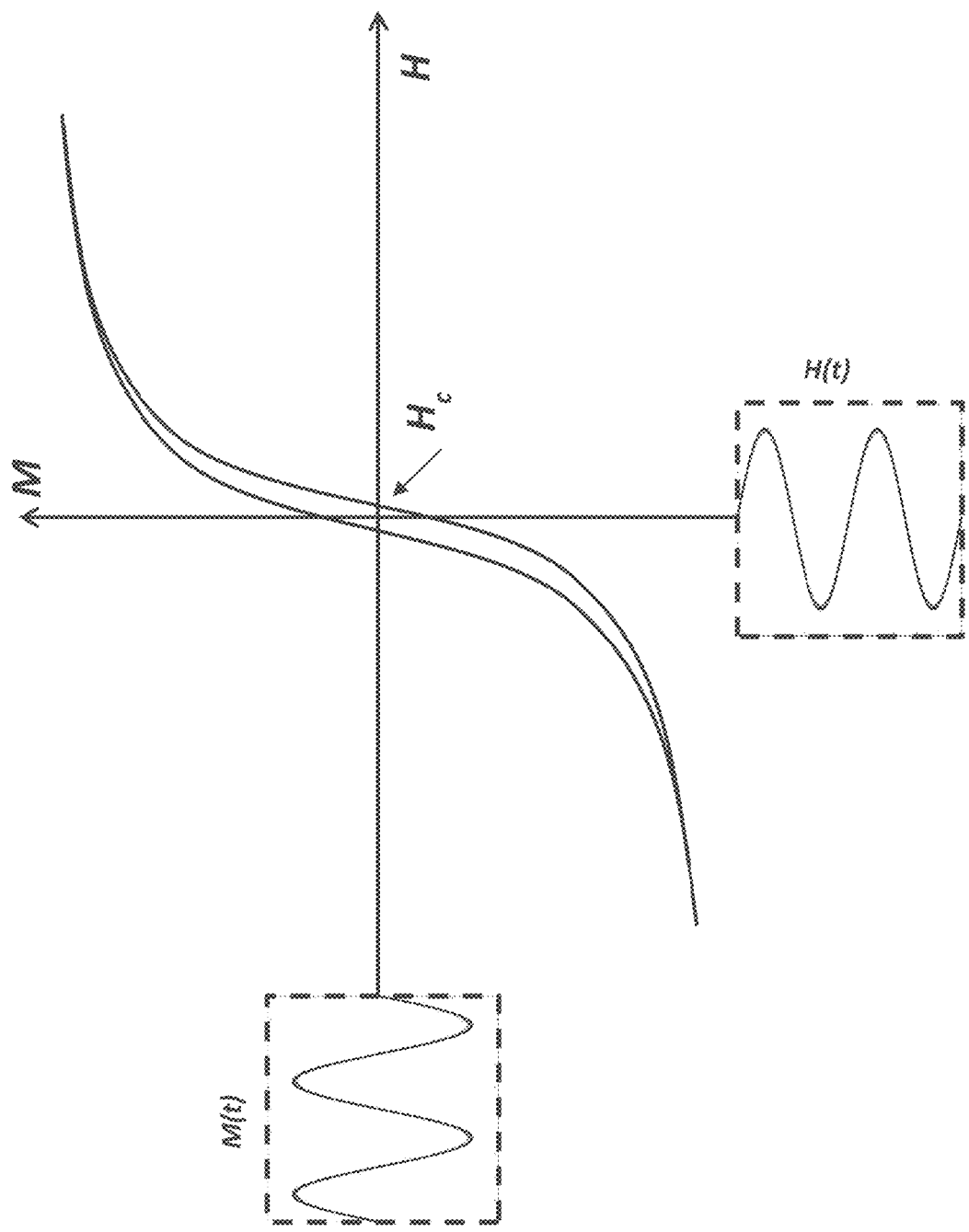
FIG. 1A shows an example magnetization curve of magnetic particles and FIGS. 1B and 1C schematically illustrate magnetization of magnetic particles using an AC magnetic coil and a permanent magnet, respectively, with an example positioning of a magnetoresistance (MR) sensor with respect to the magnetic particles and the magnetization source.
Figure 1C:
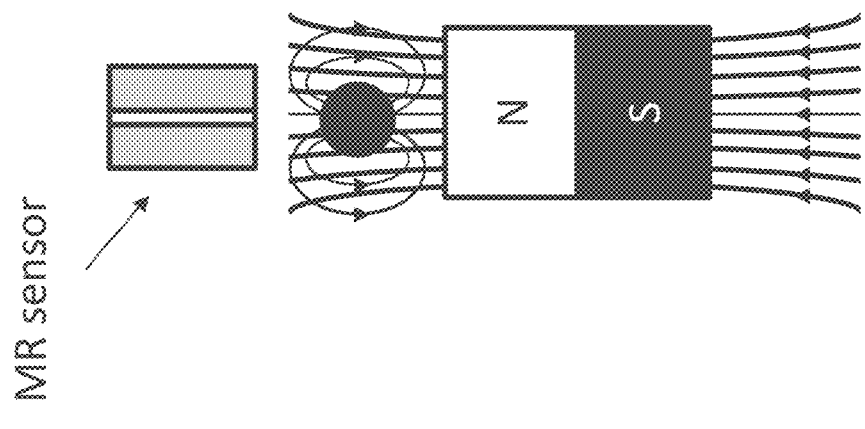
Figure 1B:
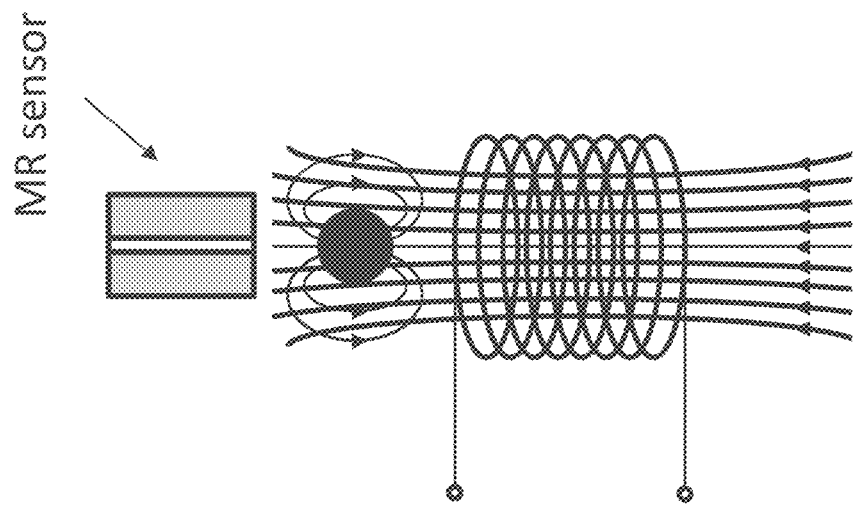

For another example, small magnetic particles are paramagnetic, so the particles do not produce magnetic induction without an external magnetic field to magnetize them. FIGS. 1A-1C schematically illustrate the general principle of magnetization of small particles and methods of detecting them. FIG. 1A shows an example magnetization curve of magnetic particles, in which the magnitude of magnetization M of a particle changes with the external magnetic field H following the hysteresis loop. For very small particles (e.g., less than 20 nm for iron oxide particles), the magnetic coercivity $H_c$ diminishes, and the particles become non-magnetic under zero external field. Such particles are also known as superparamagnetic and are ideal as probes for magnetic sensing in biological assays since the particles' magnetization M and magnetic induction B respond monotonously to the external magnetization field H, and the particles do not aggregate in liquid by magnetic dipole interaction.

To apply an external magnetic field of sufficient strength, a magnet (e.g., a magnetic coil as schematically illustrated in FIG. 1B or a permanent magnet as schematically illustrates in FIG. 1C) can be used. To generate strong AC magnetic field, the magnetic coil uses a high current power supply, and a magnetic core is often included. A narrow slit can be cut in the core where the magnetic field is most intense and uniform. Such components are often bulky, and can conflict with the limited free space available in lateral flow assay.

An additional, and potentially more severe, problem is that although the magnetic induction field of magnetic particles increases with the external magnetization field strength, the relatively weak magnetic induction field and the relatively strong external magnetization field are difficult to distinguish from one another using the magnetic field sensor (e.g., magnetoresistance or MR sensor or pickup coils). For DC magnetization, both fields have similar directions, except for small stray fields from the particles. For AC magnetization, both fields have the same frequency and phase.

A further complication in magnetic sensing for lateral flow assay is the background signals from unbound magnetic particles. Although porous nitrocellulose membranes allow fast capillary flow of the sample liquid, solid particles can be trapped in the pores, especially when the particles aggregate in liquid. The trapped particles can become a smeared magnetic background, affecting the assay sensitivity and accuracy at low antigen concentration.

Several methods and systems can be used to overcome the challenges in magnetic sensing for biological assay, depending on the assay format. For example, in configurations in which the magnetic field sensor (e.g., magnetoresistance-based; fabricated into dense arrays for multiplexing detection) can be submerged in a liquid sample (e.g., in situ assay), the biological reaction can be realized directly on the sensor surface to minimize the distance (e.g., less than or equal to 1 micron) between the magnetic particles and the sensor (see, e.g., U.S. Pat. Nos. 5,981,297 and 9,863,939). The microscopic distance between the magnetic particle and the sensor surface lowers the strength of the magnetization field for detection to a value (e.g., to below 50 Oe) that can be produced by a small coil. However, such a configuration only allows one-time use of the sensor since the biological molecules are permanently bonded to the sensor surface and cannot be reused after the biochemical reaction.

For lateral flow assays in which the space around the reaction zones is limited and a macroscopic distance between the sensor and magnetic particles is unavoidable, a strong external field is used to magnetize the magnetic particle. For example, a C-shaped magnet core with a narrow slit can be used to generate an intense and uniform magnetic field therein (see, e.g., U.S. Pat. Nos. 6,437,563 and 6,607,922) and a coil wrapped on the back of the magnetic core can provide high frequency AC modulation. The lateral flow membrane or a disk containing immobilized magnetic particles can be inserted into the slit at a close distance to the sensor. The sensor can include a pair of balanced pickup coils to differentiate the particles' magnetic induction field from the strong external magnetization field. To fit into the narrow slit of the C-shaped magnet, the lateral flow assay cassette containing the membrane can be a bow-shaped device, where the membrane is installed as the "string" of the bow without support (see, e.g., European Pat. No. EP 1552306).

Some configurations can utilize multiple high frequency AC magnetic coils for magnetization and picking up, where pairs of pickup coils (e.g., each pair including a measurement coil and a reference coil) are used for differentiating the particles' magnetic induction field from the external magnetization field (see, e.g., U.S. Pat. Nos. 6,995,021 and 8,026,716).

While coil-based magnetization and sensing methods can provide the advantages of high frequency modulation (e.g., high signal-to-noise ratio when combined with a lock-in amplifier), a drawback of certain such configurations is a lack of distinction between the specific bound magnetic particles in the reaction zone (e.g., particularly the test line) and nonspecific unbound magnetic particles trapped in the membrane. Unless the unbound particles are removed (e.g., by repeated washing), the background signal from the unbound particles at low antigen concentration can be comparable in strength to the signal from the specifically bound particles. In certain implementations described herein, the background signal from the unbound particles is advantageously reduced by using measurements with improved spatial resolution so as to spatially distinguish the reaction zone (e.g., test line) from the surrounding areas. Such spatial resolution is not provided by previous coil-based configurations in which the pickup magnetic coils either cover or enclose the space that includes the samples (e.g., the test line and a significantly large periphery area). Previous work using resonant coils in magnetic detection has not improved spatial resolution (see, e.g., Barnett et al., "An Inexpensive, Fast and Sensitive Quantitative Lateral Flow Magneto-Immunoassay for Total Prostate Specific Antigen," Biosensors, Vol. 4, pp. 204-220 (2014)).

In certain implementations described herein, the system comprises at least one magnetic field sensor based on magnetoresistance (MR) (e.g., gigantic magnetoresistance (GMR); tunneling magnetoresistance (TMR)) and the at least one magnetic field sensor is configured to be applied as a compact magnetic field sensor for ex situ biological assays where the sensor is separated in space from the assay (as compared with in situ assays where the sensor is within the assay liquids, see, e.g., U.S. Pat. Nos. 5,981,297 and 9,863,939). Progress in semiconductor manufacturing in the past decades has made such sensors available for broad applications, beyond their traditional usage as computer hard disk readers and in automotive speedometers.

For example, in a previous study of TMR sensors in lateral flow arrays, a C-shaped permanent magnet with a narrow slit provided the external magnetization field applied to the magnetic particles. Similar to the principle of using a balanced pair of pickup coils in coil-based methods, a pair of TMR sensors were positioned on both sides of the test line to differentiate against common mode background signal (e.g., from the external magnetization field). High frequency AC modulation of the TMR sensor power supply and a lock-in amplifier were used to improve the signal-to-noise ratio. An assay of human chorionic gonadotropin (hCG) demonstrated a limit of detection (LOD) of 25 mIU/ml of hCG (equivalent to about 2 ng/ml), which is not as good as other non-magnetic methods, such as a fluorescence-based lateral flow assay reader (see, e.g., U.S. Pat. No. 9,488,585). Although the small size of TMR sensors enabled high spatial resolution in principle, using a sensor pair for common mode rejection rendered the differential signal as a convolution of two signals from two sensors separated in space, and sacrificed the special resolution. (See, e.g., Lei et al., "Contactless Measurement of Magnetic Nanoparticles on Lateral Flow Strips Using Tunneling magnetoresistance (TMR) Sensors in Differential Configuration: Sensors, Vol. 16, p. 2130 (2016)).

For another example, reader platforms based on GMR sensors for quantitative lateral flow immunoassays have previously used a pair of strong permanent magnets (e.g., 4000 G) to provide a uniform and intense magnetization field, a Helmholtz coil to provide a sweeping magnetic field at an angle to the pair of permanent magnets, and a linear (DC) motor system to provide membrane cassette transportation and distance control between the sensor and the membrane. Signals were recorded when the membrane moved relative to the sensor, and stray fields of the magnetic particles parallel to the membrane plane were measured. Because such fields are strongest at a distance away from the particles, the resultant signal had a spatial span of 7 mm in the membrane plane. This wide span of signal of a single line severely limited the spatial resolution of detection and caused interference between the control line and the test line, both of which are used in standard lateral flow assays and are typically separated by only 5-10 mm (see, e.g., J. Park, "A Giant Magnetoresistive Reader Platform for Quantitative Lateral Flow Immunoassays," Sensors and Actuators A, Vol. 250, pp. 55-59 (2016); J. Park, "Superparamagnetic Nanoparticle Quantification Using a Giant Magnetoresistive Sensor and Permanent Magnets," J. Mag. And Mag. Mat'ls, Vol 389, pp. 56-60 (2015)).

Certain implementations described herein advantageously utilize magnetic detection for lateral flow and other biological assays to provide high sensitivity, sufficient specificity against the background unbound particles, and more reliable quantification (e.g., capability to differentiate between logarithmic steps; e.g., between 1, 0.1, 0.01 ng/ml, etc.) than previous configurations.

Example Implementations

Figure 2A:
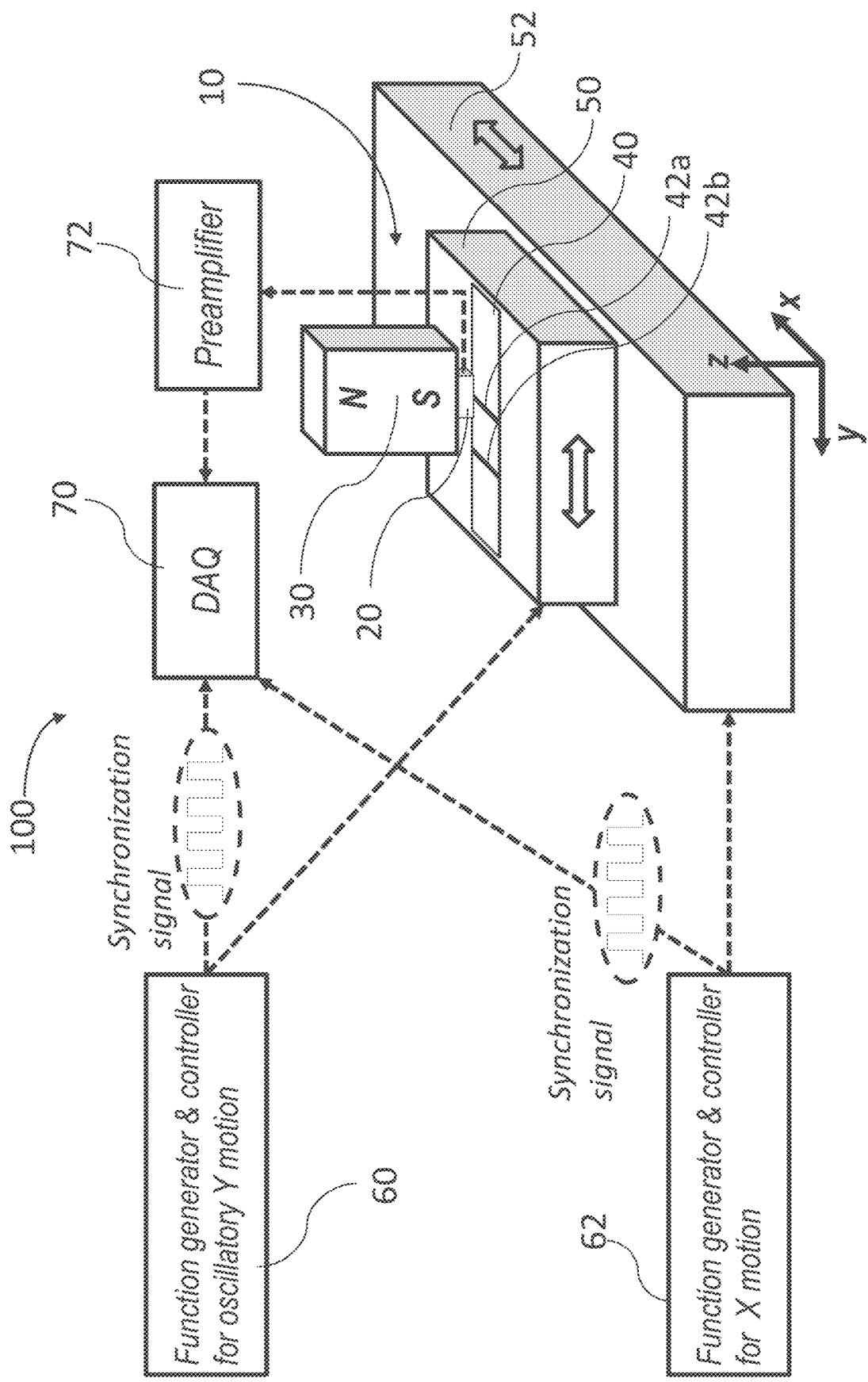
FIG. 2A schematically illustrates an example apparatus and an example system comprising the apparatus in accordance with certain implementations described herein.
Figure 2B:
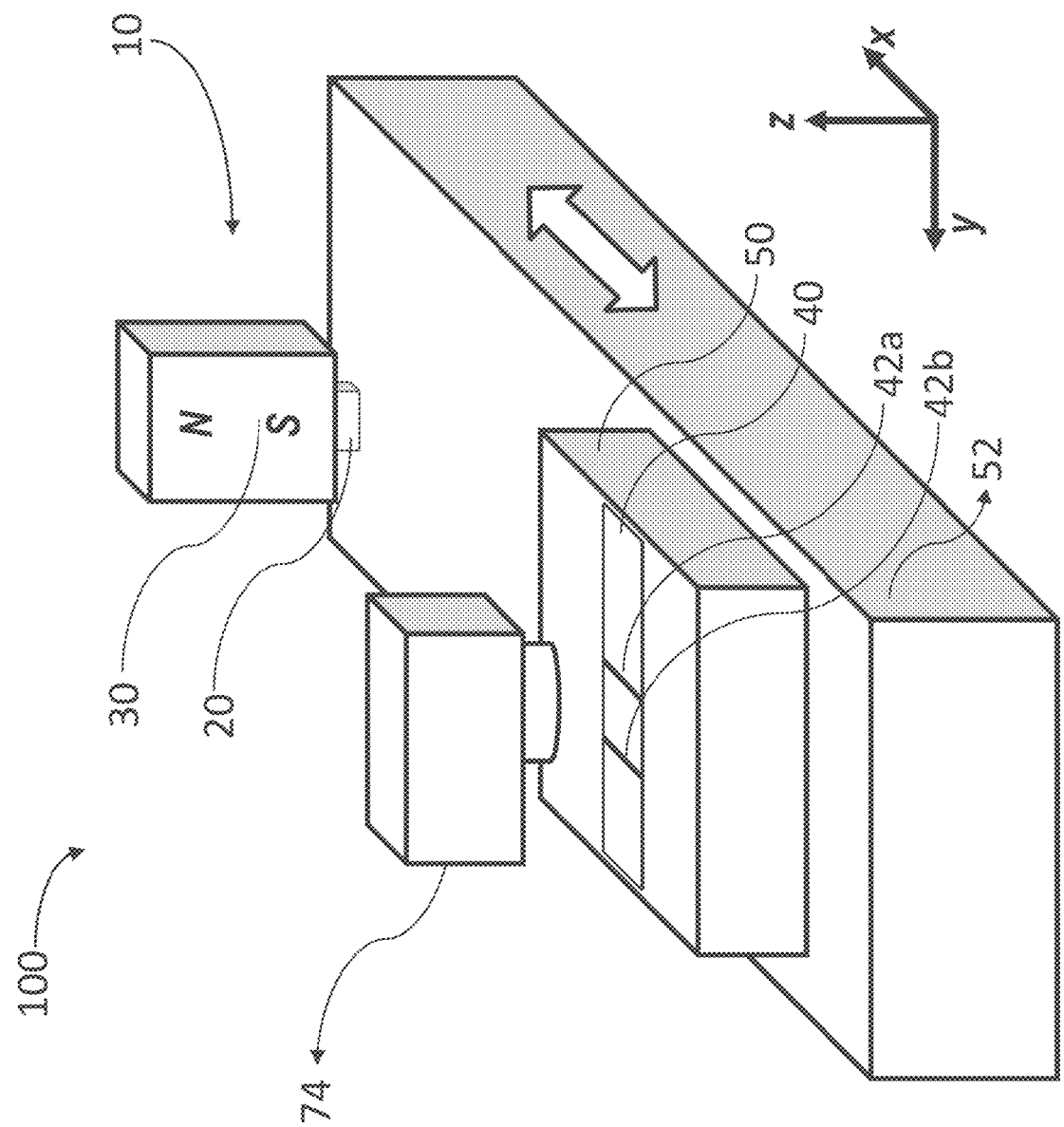
FIG. 2B schematically illustrates the example apparatus and another example system comprising the apparatus in accordance with certain implementations described herein.

FIG. 2A schematically illustrates an example apparatus 10 and an example system 100 comprising the apparatus 10 in accordance with certain implementations described herein. FIG. 2B schematically illustrates the example apparatus 10 and another example system 100 comprising the apparatus 10 in accordance with certain implementations described herein. The apparatus 10 comprises at least one magnetic field sensor 20 (e.g., a magnetoresistance sensor) and at least one permanent magnet 30, the at least one magnetic field sensor 20 at (e.g., attached to) a pole of the at least one permanent magnet 30. The apparatus 10 is configured to be positioned such that the at least one magnetic field sensor 20 is above a surface of a lateral flow membrane 40 containing immobilized magnetic particles (e.g., captured in reaction zones of a test line 42*a* and control line 42*b* of the membrane 40). The apparatus 10 can have an area of contact with the membrane 40 in a range of 1 mm$^2$ to 100 mm$^2$ (e.g., 1 mm×1 mm to 10 mm×10 mm), and/or is compatible with the dimensions of standard lateral flow assays (e.g., with membrane lengths of several centimeters, membrane width of 5 mm, test line and control line separation of 5 mm to 10 mm). As schematically illustrated by FIG. 2A, the surface of the membrane 40 is in close proximity to a surface of the at least one magnetic field sensor 20 (e.g., a distance between the surface of the membrane 40 and the surface of the magnetic field sensor 20 is in a range of less than or equal to 100 microns.

In certain implementations, the at least one magnetic field sensor 20 comprises at least one magnetoresistance (MR) sensor, examples of which include but are not limited to: gigantic magnetoresistance (GMR) sensors and tunneling magnetoresistance (TMR) sensors. The at least one MR sensor can have a wide range of dimensions and operation conditions in accordance with certain implementations described herein. For example, for highly sensitive applications, bare MR sensors without packaging can be as small as a few microns. With packaging protection for robust usage, the dimensions of the at least one MR sensor, including packaging, can be in a range of 5 mm to 10 mm, and/or is compatible with the dimensions of standard lateral flow assays. In certain implementations, the at least one MR sensor can be powered by an electric voltage in a range of 5 V to 10 V, which consumes a small amount of electric power, and is therefore compatible with compact design and portable usage.

In certain implementations, the at least one permanent magnet 30 comprises at least one ferromagnetic material, examples of which include but are not limited to: magnetic materials doped with rare earth elements, e.g., neodymium; samarium-cobalt. Magnets compatible with various implementations described herein are widely available with different shapes, sizes, and strengths. For example, the permanent magnet 30 can have a size in a range of 5 mm to 10 mm in each dimension, and/or can have a magnetic field strength in a range of 500 Oe to 1000 Oe.

In certain implementations, the lateral flow membrane 40 is a representation of a plural of solid supporting materials for immobilization of magnetic particles upon specific detection of analyte. Other solid materials that can be used to support the biological recognition reactions include but are not limited to: paper, glass, metal, and semiconductor. For example, a glass surface can be printed with antibodies or DNA molecules that bind specifically to a specific analyte. Gold surfaces are well known to have good affinity with proteins and antibodies. Assays established on such solid surfaces with magnetic particles can be detected with the method and system in accordance with certain implementations described herein. For another example, the membrane 40 can comprise nitrocellulose paper with printed capture antibody lines for capturing antigens (e.g., cut to a rectangular shape of 5 cm×50 cm). Liquid capillary flow capacity can be measured by the time for water to travel 4 cm along the membrane 40, and such time can be in a range of 80 seconds to 150 seconds. In certain implementations, the magnetic particles comprise (i) one or more magnetic materials configured to be magnetized and to generate a magnetic induction field in response to an applied external magnetic field and (ii) one or more surface coating materials that are configured to selectively bind to an analyte of interest to be detected (e.g., measured) in an assay of the analyte. For example, the magnetic particles can comprise magnetic iron oxide particles, which are widely used in biological separations and are compatible with certain implementations described herein. In certain implementations, the magnetic iron oxide particles have a size in a range of 20 nm to 200 nm and/or a magnetic susceptibility in a range of 20 emu/g to 100 emu/g, and have a surface coating (e.g., antibodies for biological recognition and binding). For another example, the magnetic particles comprise nanoparticles can include Au—Fe alloy nanoparticles and/or can be fabricated using various processes (see, e.g., U.S. Pat. Appl. Publ. No. 2011/0192450; Int'l Publ. No. WO2014/160844; Int'l Publ. No. WO2018/022776; each of which is incorporated in its entirety by reference herein). Such Au—Fe alloy particles have a magnetic susceptibility (e.g., in a range of 50 emu/g to 150 emu/g) that is higher than the magnetic susceptibility of iron oxide particles, so Au—Fe particles also have higher magnetic moments and generate stronger magnetic induction than do iron oxide particles. In certain implementations, in addition to being configured to generate a magnetic induction field, the magnetic nanoparticles are further configured to absorb light (e.g., in the visible range) and to generate colorimetric signals (e.g., color intensity) to be detected (e.g., measured) in an assay for the analyte of interest. For example, most iron oxide particles have a broad optical absorption in the visible range and have a dark brown color. Magnetic Au—Fe alloy particles have a broad and nearly flat optical absorption in the entire visible range and appear nearly black against the white background of the membrane 40.

In certain implementations, as schematically illustrated by FIGS. 2A-2B, the example system 100 further comprises a mechanical motion stage 50 (e.g., an x-y-z stage) mechanically coupled to at least one of the apparatus 10 and the lateral flow membrane 40. The stage 50 is configured to move at least one of the apparatus 10 and the membrane 40 relative to one another with a periodic oscillatory movement. For example, the stage 50 can be configured to move the membrane 40 relative to the apparatus 10 (e.g., while the apparatus 10 is stationary) in a direction that is substantially perpendicular to the test and control lines 42a, 42b (denoted herein as the y-direction). For another example, the stage 50 can be configured to move the apparatus 10 relative to the membrane 40 (e.g., while the membrane 40 is stationary) in a direction that is that is substantially perpendicular to the test and control lines 42a, 42b (denoted herein as the y-direction). In certain implementations, the periodic oscillatory mechanical movement has an amplitude in the y-direction (e.g., in a range of 2 mm to 5 mm) that is at least twice a width of the test line 42a and/or the control line 42b (e.g., at least twice a width of 1 mm), but less than the distance between the two lines 42a, 42b (e.g., to avoid interference) (e.g., less than a distance in a range of 5 mm to 10 mm). In certain implementations, the periodic oscillatory mechanical movement has a frequency in a range of 1 Hz to 10 Hz and a peak linear speed of oscillation (e.g., in the y-direction) in a range of 10 mm/s to 200 mm/s.

Various mechanisms (e.g., translation stages) for the periodic oscillatory mechanical movement are compatible with certain implementations described herein. Factors to be considered include but are not limited to: oscillation frequency, amplitude, range of motion, precision of motion (e.g., minimum hysteresis or time lag), electric and magnetic noise, device compactness, lifetime, and cost. Example mechanisms compatible with certain implementations described herein include but are not limited to: quartz oscillators, piezoelectric oscillators, piezoelectric actuators; piezoelectric motors; linear stepper motors, DC motors, and voice coils. In certain implementations described herein, the mechanism is selected or designed to advantageously provide oscillatory movement while reducing (e.g., avoiding; preventing; minimizing) one or more deleterious effects (e.g., severe hysteresis; quick wear of gears or other components; high noise).

For example, the stage 50 can comprise a voice coil configured to provide the oscillatory movement. The voice coil can comprise a magnetic coil and a permanent magnet that can oscillate freely against each other when an AC current is provided to the coil. In certain such implementations, the magnetic components of the system 100 (e.g., the magnetic coil and the opposite magnet of the voice coil) generate a periodic background signal in the magnetic field sensor 20 to be filtered out either electronically or digitally.

For another example, the stage 50 can comprise a piezoelectric oscillator configured to provide oscillatory movement with sufficient frequency (e.g., up to 5 Hz; up to 10 Hz; in a range of 1 Hz to 100 Hz), sufficient amplitude (e.g., up to 5 mm), wide range of motion (e.g., up to 20 mm), and low electric and magnetic noise. In certain such implementations, the piezoelectric oscillator has a higher hysteresis than does a voice coil, and the hysteresis can be minimized with a proper set of proportional, integral, and derivative (PID) parameters in the closed loop control system.

In certain implementations, as schematically illustrated by FIGS. 2A-2B, the stage 50 comprises a linear motion sub-stage 52 (e.g., linear stepper and/or DC motor stage) configured to move or scan at least one of the apparatus 10 and the membrane 40 relative to one another with a linear mechanical movement in a direction substantially parallel to the test and control lines 42a, 42b (denoted herein as the x-direction). For example, the sub-stage 52 can be configured to move or scan the membrane 40 relative to the apparatus 10 (e.g., while the apparatus 10 is stationary) in a direction that is substantially parallel to the test and control lines 42a, 42b, or the sub-stage 52 can be configured to move or scan the apparatus 10 relative to the membrane 40 (e.g., while the membrane 40 is stationary) in a direction that is substantially parallel to the test and control lines 42a, 42b. In certain implementations, the movement in the x-direction can be slower than the movement in the y-direction (e.g., the speed of the x-direction movement can be in a range of 1 mm/s to 10 mm/s. In certain implementations, the sub-stage 52 is configured to transport the membrane 40 to and from the measurement position (e.g., beneath the apparatus 10). In certain implementations, the stage 50 comprises the linear motion sub-stage 52 configured for scanning and a rotational sub-stage configured for transporting the membrane 40 to and from the measurement position.

In certain implementations, as schematically illustrated by FIG. 2A, the example system 100 further comprises a first controller 60 (e.g., a microprocessor circuit comprising a first function generator) configured to control the oscillatory movement of the stage 50 along the y-direction and a second controller 62 (e.g., a microprocessor circuit comprising a second function generator) configured to control the movement of the sub-stage 52 along the x-direction. In certain implementations, the first controller 60 is separate from the second controller 62, while in certain other implementations, the first controller 60 and the second controller 70 are components of the same circuitry.

In certain implementations, as schematically illustrated by FIG. 2A, the example system 100 further comprises a data acquisition (DAQ) unit 70 (e.g., comprising a microprocessor circuit). Both the first controller 60 and the second controller 62 can be configured to generate and transmit synchronization trigger signals to the DAQ unit 70, and the DAQ unit 70 can be configured to receive the synchronization trigger signals and sensor signals generated and transmitted by the at least one magnetic field sensor 20 (e.g., via a signal processing circuitry 72 as schematically illustrated by FIG. 2A). In certain implementations, the triggered time averaging of the sensor signals is in synchronization with the movement of the stage 50 in the x- and y-directions, and is processed by a computer (not shown) running a corresponding program.

The example system 100 schematically illustrated by FIGS. 2A-2B can be modified in accordance with certain implementations described herein. For example, instead of being moved with a periodic oscillatory movement in the y-direction, at least one of the apparatus 10 and the membrane 40 can be moved relative to one another with an periodic oscillatory movement in the x-direction and instead of being moved with a linear movement in the x-direction, at least one of the apparatus 10 and the membrane 40 can be moved relative to one another with a substantially linear movement in the y-direction.

In certain implementations, as schematically illustrated by FIG. 2B, the system 100 is configured to perform colorimetric reading in addition to the magnetic reading of the test and control lines 42a, 42b. For example, the system 100 can comprise a camera 74 (e.g., an optical camera) configured to be positioned above the membrane 40 (e.g., before the membrane 40 is positioned below the at least one magnetic field sensor 20 for magnetic reading. The images (e.g., photographs) obtained by the camera 74 can provide color intensity information regarding the test and control lines 42a, 42b. For example, when the analyte concentration is high such that the test line color is visible and readily detectable by the colorimetric reading using the camera 74, the color intensity information can be sufficient for the assay. When the analyte concentration is low such that the test line color is not visible and/or readily detectable by the colorimetric reading using the camera 74 (e.g., the assay can benefit from more sensitive detection), the system 100 can utilize the apparatus 10 to provide more sensitive and quantitative assay results from the membrane 40 in accordance with certain implementations described herein.

Figure 3A:
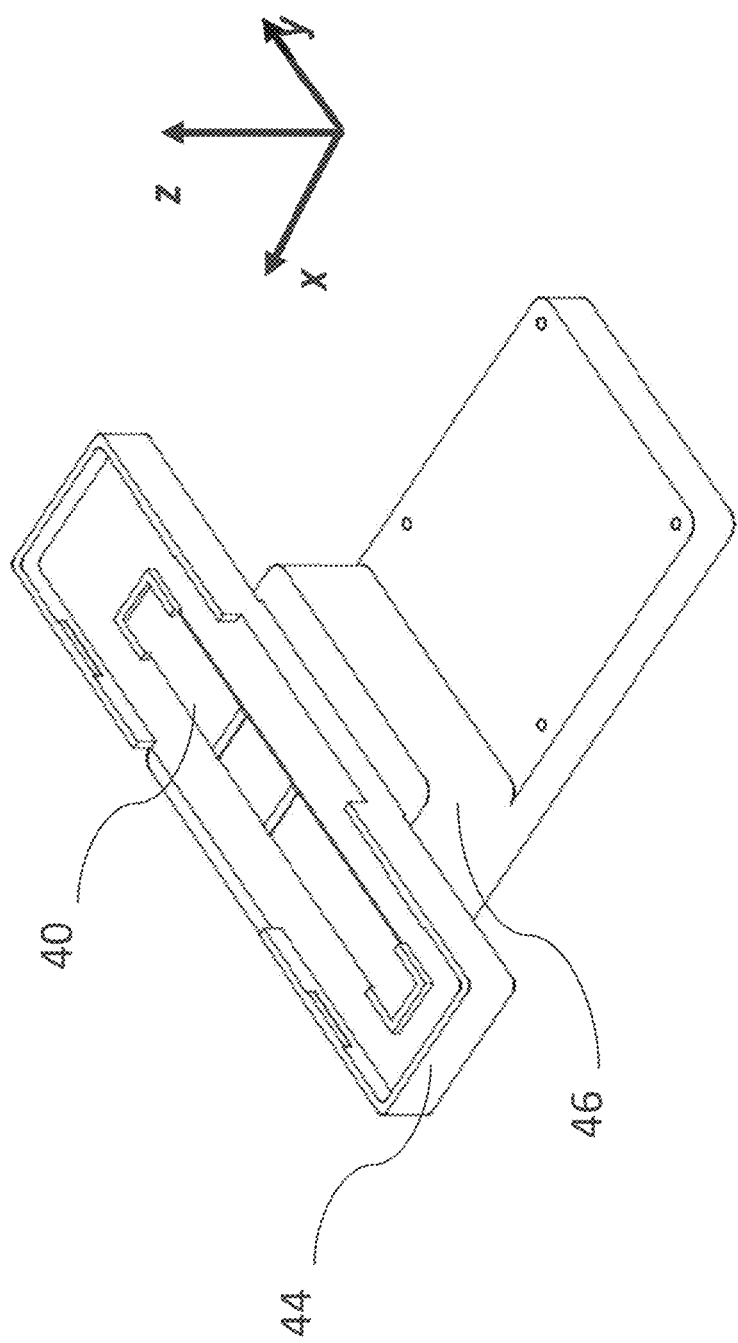
FIGS. 3A-3D show various views depicting an example apparatus and example system in accordance with certain implementations described herein.

FIGS. 3A-3D show various views depicting an example apparatus 10 and example system 100 in accordance with certain implementations described herein. FIG. 3A shows a cassette 44 containing the lateral flow membrane 40 in accordance with certain implementations described herein. In certain implementations, two sides of the cassette 44 are cut down to the level of the membrane 40 so that the cassette 44 can be transported smoothly to and from the measurement position below the apparatus 10 (e.g., below the magnetic field sensor 20). In certain implementations, the cassette 44 can be modified in other ways, or omitted, to allow for such smooth transportation. As illustrated by FIG. 3A, a cassette holder 46 can be configured to hold the cassette 44 and to be mounted on the stage 50. In certain implementations, a position sensor (e.g., pressure sensor; proximity sensor) (not shown) may be mounted (e.g., hidden) inside the cassette holder 46 beneath the cassette 44 and configured to monitor the position (e.g., distance) of the membrane 40 relative to the magnetic field sensor 20 (e.g., by monitoring the pressure between the membrane 40 and the magnetic field sensor 20). In certain such implementations, a signal from the position sensor can be used to maintain sufficient proximity between the membrane 40 and the magnetic field sensor 20 (e.g., close and constant contact without tearing the fragile membrane 40).

Figure 3B:
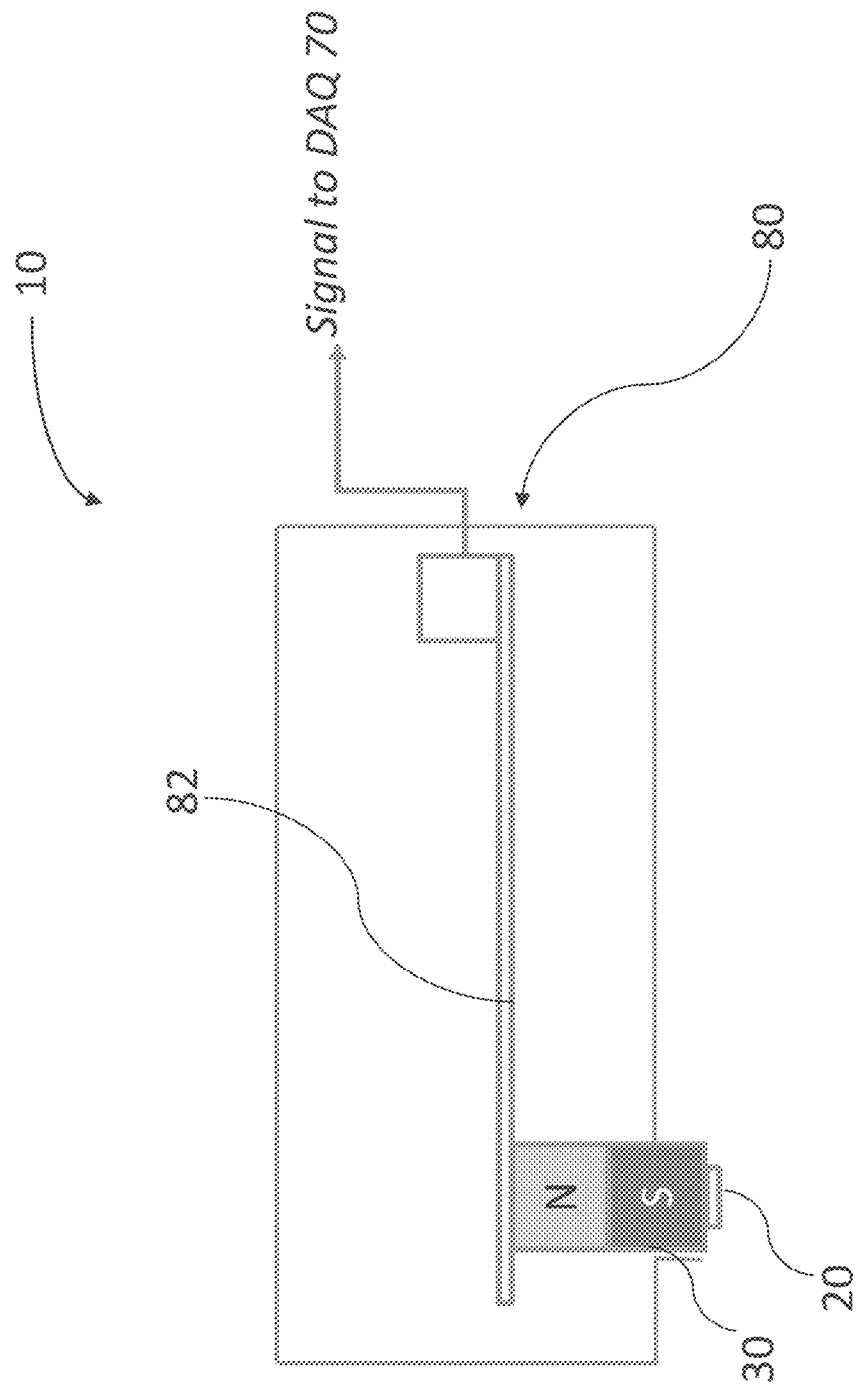

FIG. 3B schematically illustrates an example apparatus 10 in accordance with certain implementations described herein. The example apparatus 10 comprises the magnetic field sensor 20 and the permanent magnet 30 and a metal shielding box 80 containing a printed circuit board (PCB) 82 comprising the signal conditioning and preamplifier circuits of the signal processing circuitry 72. The shielding box 80 can be installed on a y-z stage 90 (e.g., manually-controlled and/or electronically-controlled) for precise height adjustment (denoted herein as the z-direction) and positioning of the magnetic field sensor 20 relative to the membrane 40 in the y-direction. The sensor signal from the magnetic field sensor 20 is transmitted to the DAQ unit 70 via the signal processing circuitry 72.

Figure 3C:
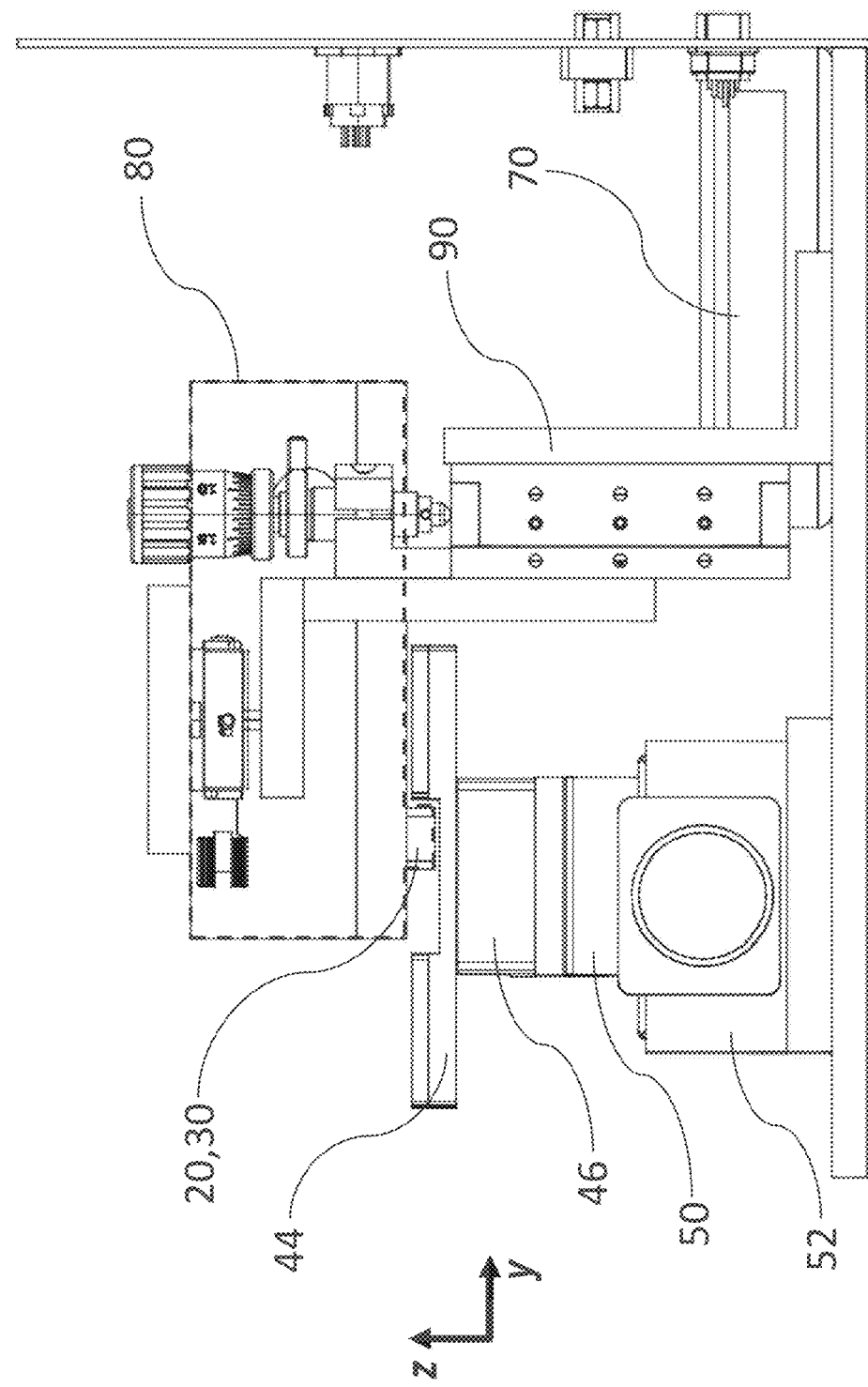
Figure 3D:
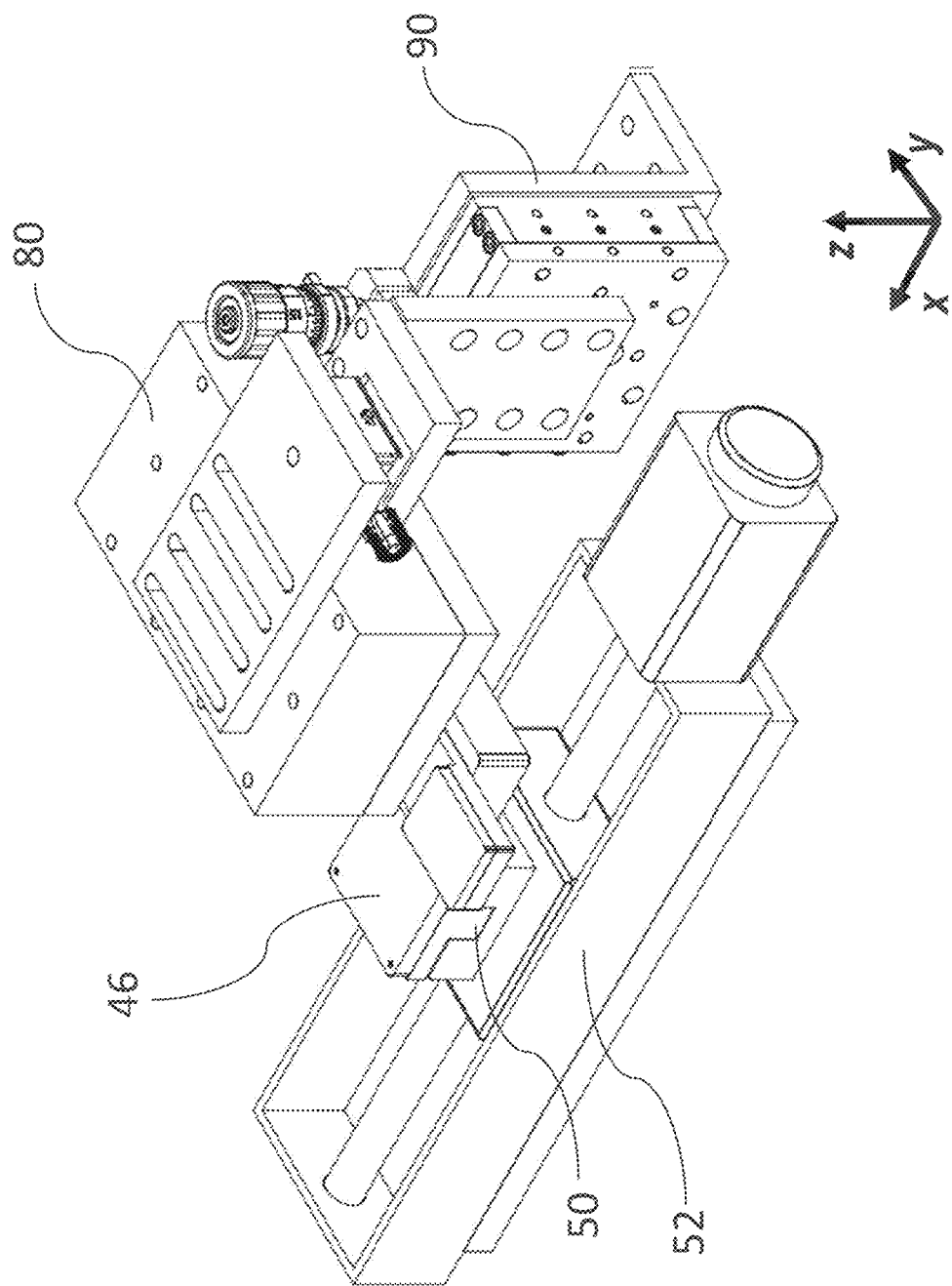

FIGS. 3C and 3D show a right-side view and a perspective view, respectively, of the example system 100 in accordance with certain implementations described herein. In FIG. 3C, the shielding box 80 is denoted by a dashed line. The linear motion sub-stage 52 can comprise a motor (e.g., stepper motor; DC motor) and can be configured to scan the membrane 40 in a direction along (e.g., substantially parallel to) the test and control lines 42a, 42b (e.g., along the x-direction) and/or to transport the membrane 40, cassette 44, and cassette holder 46 in and out of the measurement location for sample exchange (e.g., along the x-direction). The stage 50 can comprise a piezoelectric motor configured to oscillate the membrane 40 in a direction substantially perpendicular to the test and control lines 42a, 42b (e.g., along the y-direction) and can be mounted on top of the linear motor of the sub-stage 52.

Figure 4:
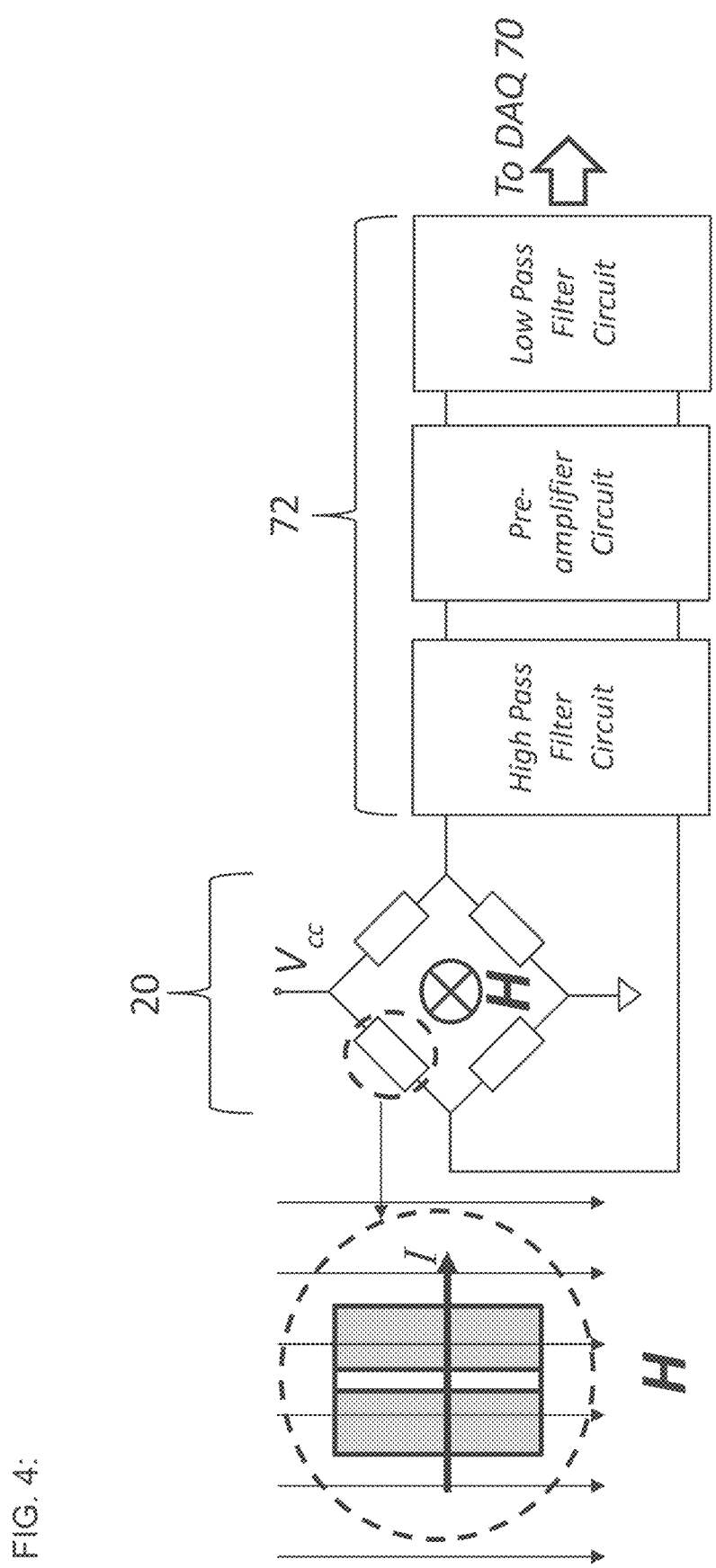
FIG. 4 schematically illustrates an example electronic block diagram of the at least one magnetic field sensor and example signal processing circuitry (e.g., for signal conditioning and amplification) in accordance with certain implementations described herein.

FIG. 4 schematically illustrates an example electronic block diagram of the at least one magnetic field sensor 20 and example signal processing circuitry 72 (e.g., for signal conditioning and amplification) in accordance with certain implementations described herein. The at least one magnetic field sensor 20 of FIG. 4 comprises four individual magnetic field sensors 20a-20d in a Wheatstone bridge configuration. The at least one magnetic field sensor 20 is configured for common mode rejection such that when an oscillating membrane 40 periodically passes over the Wheatstone bridge, the Wheatstone bridge generates a differential signal pertinent to the movement of the membrane 40. In certain implementations, the size (e.g., width in a plane substantially parallel to the membrane 40) of the Wheatstone bridge is configured to provide spatial resolution in 2D mapping of the test and control lines 42a, 42b. For example, the size of the Wheatstone bridge can be smaller than the linewidth of the test and control lines 42a, 42b (e.g., in a range of 0.1 mm to 0.5 mm). In certain implementations, the signal processing circuitry 72 comprises a high pass filter circuit having a first cutoff frequency (e.g., 0.3 Hz) configured to remove the DC baseline and a low pass filter circuit having a second cutoff frequency (e.g., 300 Hz) configured to remove high frequency noise. The dashed circle of FIG. 4 encircles a TMR sensor of the at least one magnetic field sensor 20 and the enlarged view at the left-side of FIG. 4 schematically illustrates the orientation of the TMR sensor with respect to the external magnetic field from the permanent magnet 30. While FIG. 4 schematically illustrates an example implementation using a TMR sensor (e.g., having a sufficiently high sensitivity for detection of the magnetic particles of the membrane 40), other types of magnetoresistance sensors (e.g., GMR sensors) can also be used in accordance with certain implementations described herein.

Figure 5:
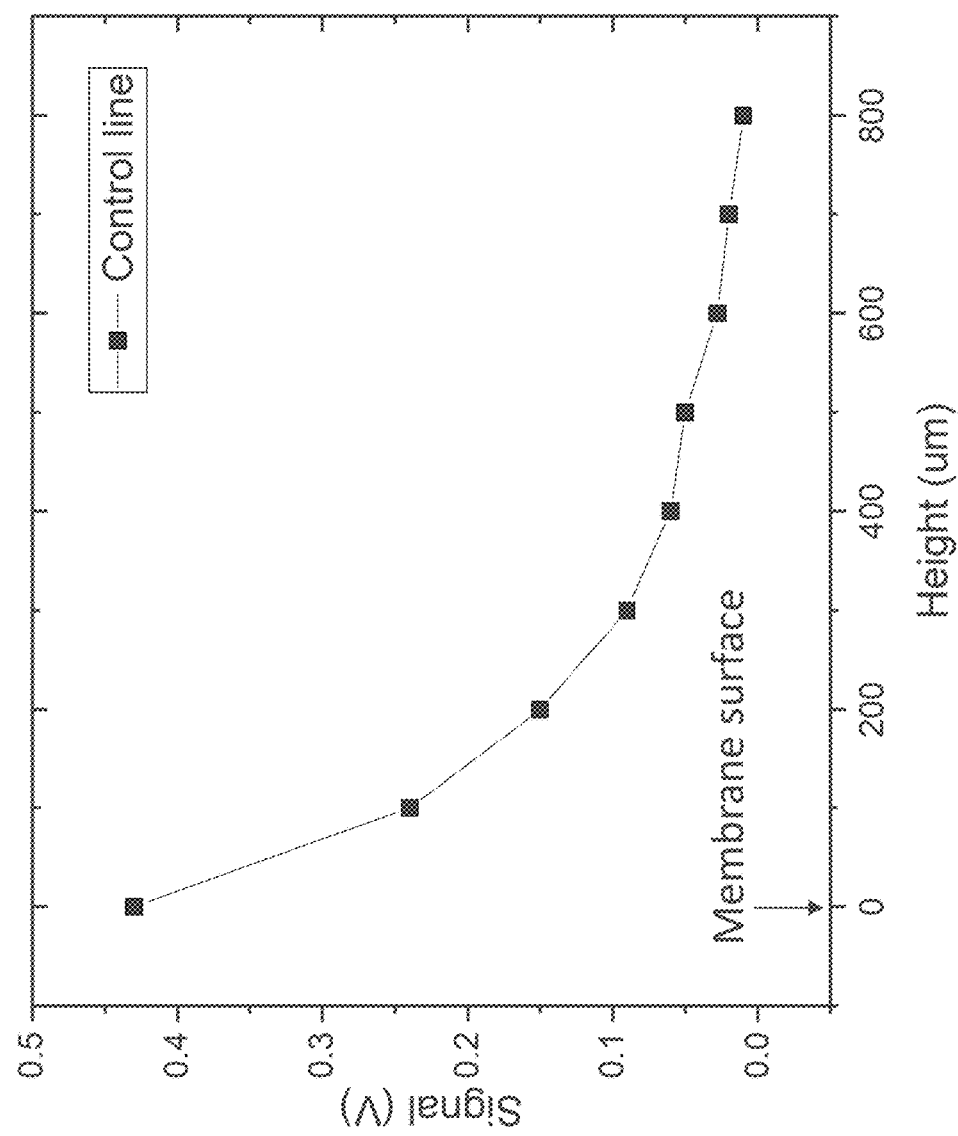
FIG. 5 shows an example plot of the dependence of the measured field sensor signal on the sensor height relative to the membrane surface in accordance with certain implementations described herein.

FIG. 5 shows an example plot of the dependence of the measured sensor signal on the sensor height relative to the membrane surface in accordance with certain implementations described herein. An inverse quadratic drop of the measured sensor signal with increasing distance is observed, which is expected for small particles as the source of the magnetic field. In certain implementations, to allow for ample signal detection, the distance between the sensor surface and the membrane surface is in a range of less than a few hundred microns (e.g., 0 to 100 microns).

In certain implementations, the magnetization field from the permanent magnet 30 is substantially constant in time (e.g., does not change), and modulation of the signal is performed by modulating the magnetic induction of the magnetic particles of the membrane 40, thus improving the signal-to-noise ratio. For example, a periodic oscillatory motion of the membrane 40 relative to the apparatus 10, or vice versa, is used (e.g., without using a sensor pair to differentiate the particles' magnetic signal from the external magnetization field). For example, the stage 50 (see, e.g., FIG. 3) can have an oscillation frequency in a range of 1 Hz to 10 Hz and an amplitude in a range of 1 mm to 5 mm. Other (e.g., higher) oscillation frequencies are also compatible with certain implementations described herein, although the frequency can be limited by the mechanical capability of the stage 50.

Compared with the high frequency AC modulation (e.g., kHz) used previously, low frequency mechanical modulation may initially appear to be impractical for improving the signal-to-noise ratio, especially considering the omnipresent 1/f noise. However, a careful examination of the effect of a linear motion of the membrane 40 relative to the magnetic field sensor 20 reveals a better situation, and in certain implementations, low frequency modulation of the magnetization is both feasible and favored for magnetic sensing in lateral flow assay. For example, assuming a sinusoidal motion along the y-direction of $y(t)=A \sin(2\pi ft)$, the corresponding velocity of the motion is $dy/dt=2\pi Af \cos(2\pi ft)$. For a frequency of 4 Hz and an amplitude of 2 mm (e.g., in accordance with certain implementations described herein), the peak velocity is about 50 mm/s. Assuming a linewidth of 1 mm for a lateral flow test line 42a, such an oscillatory motion at its peak velocity produces a pulsed signal of time width $\Delta t=0.02$ s. Fourier transformation of the pulsed signal gives a frequency bandwidth of $\Delta f=1/\Delta t$ of 50 Hz, which is much better than the fundamental oscillation frequency f for reduction of 1/f noise. In certain implementations, the maximum velocity is selected based on the distance between the test line 42a and the control line 42b (e.g., in a range of 5 mm to 10 mm) so as to provide acceleration and deceleration sufficient to distinguish the two lines 42a, 42b from one another.

More careful examination of the magnetization behavior of small magnetic particles in the frequency domain shows that low frequency magnetic modulation is favored for magnetic sensing in lateral flow assay. The magnetization curve of small magnetic particles denoted in FIG. 1A is not representative of AC magnetization, and the more proper theory of AC magnetization of small particles is the Neel relaxation theory (see, e.g., B. Fischer et al., "Brownian Relaxation of Magnetic Colloids," J. Mag. And Mag. Mat'ls, Vol. 289. Pp. 74-77 (2005)). The Neel relaxation theory considers the time scale of a small particle's magnetic moment relaxation under thermal equilibrium, and concludes that the magnetic moment relaxation time, and therefore the frequency response in AC magnetization, depends on the particle size.

Figure 6A:
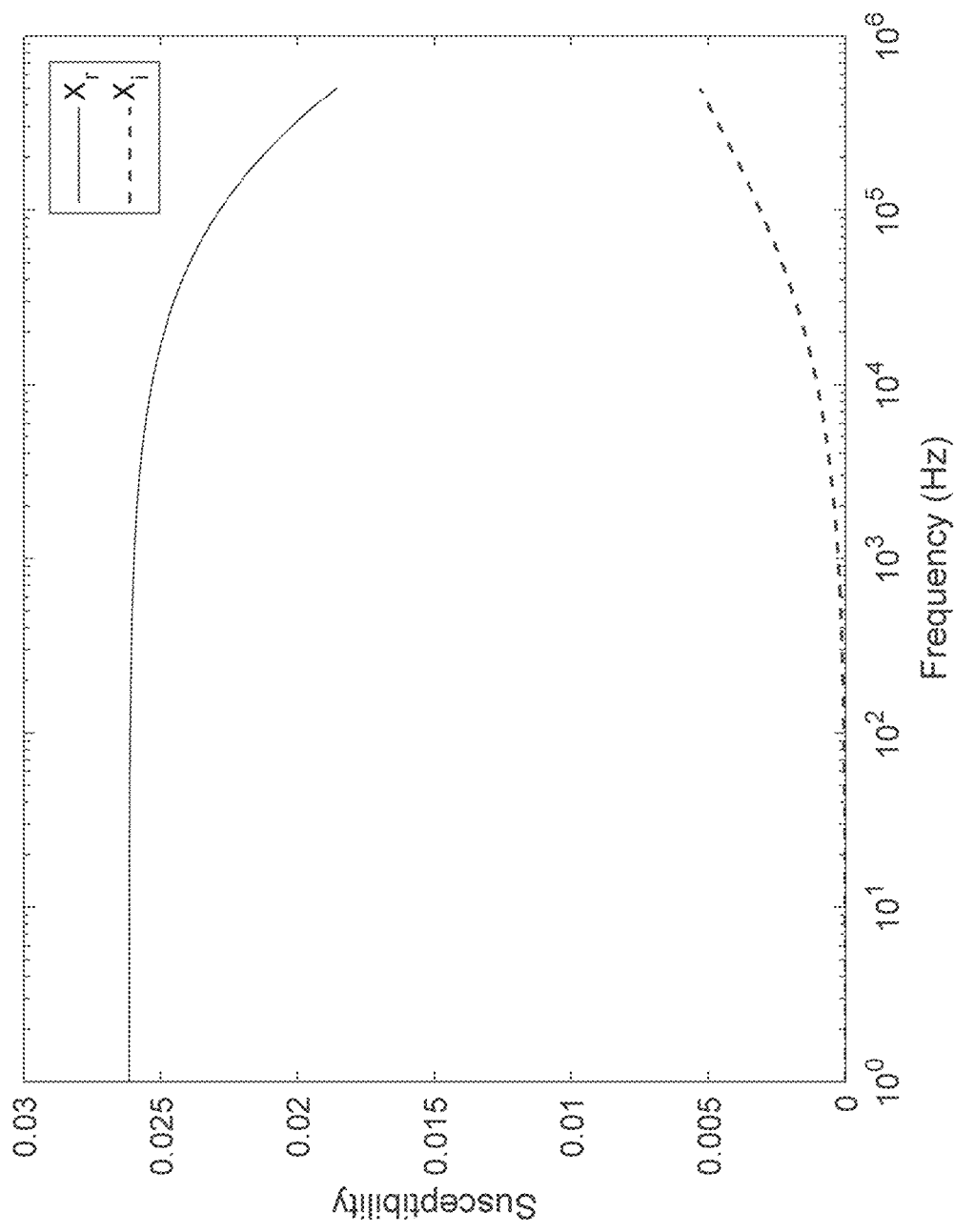
Figure 6B:
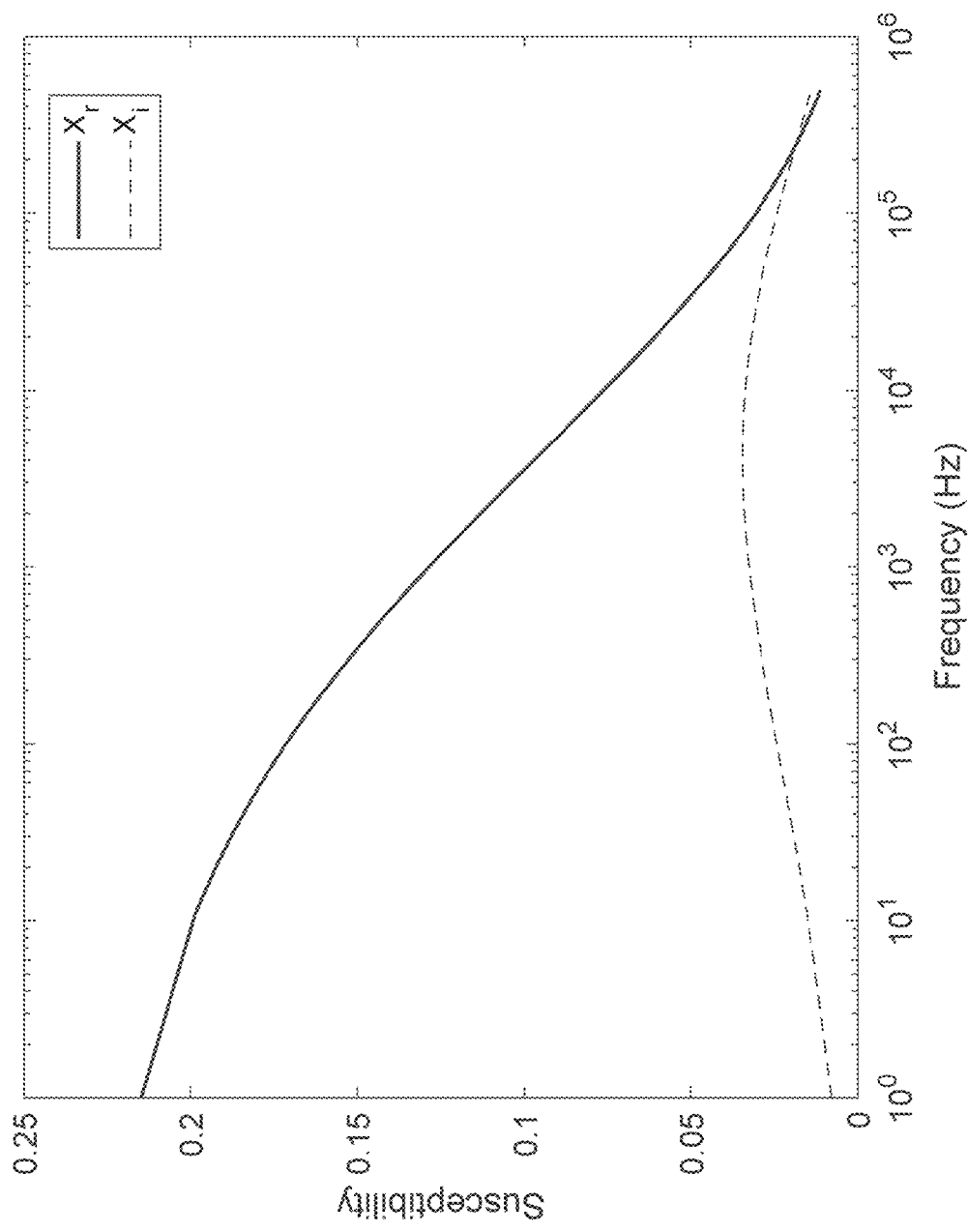

FIGS. 6A-6C are plots of theoretical calculations of the magnetic AC susceptibility ($X=M/H$) of iron oxide nanoparticles as a function of frequency for particles of different sizes (e.g., diameters) (FIG. 6A: 10 nm; FIG. 6B: 15 nm; FIG. 6C: 20 nm), assuming Gaussian distributions with $\sigma=2$ nm. The real part of the susceptibility $X_r$ is responsible for the magnetic induction of particles, while the imaginary part $X_i$ contributes to heat generation. In FIGS. 6A-6C, both $X_r$ and $X_i$ are normalized to DC values of 20 nm iron oxide particle. FIGS. 6A-6C show that except for very small particles of 10 nm, the susceptibility $X_r$ of magnetic particles drops quickly with frequency, diminishing at high frequency greater than 1 kHz. These calculations imply that smaller magnetic particles are advantageous for AC magnetization. However, since the total magnetic moment of a particle is proportional to its volume, larger particles (e.g., diameters greater than 10 nm) are advantageously used as magnetic probes for lateral flow as long as these larger particles can move through the pores of the membrane 40 (e.g., about 200 nm on average). In view of the drop of susceptibility with frequency for larger particles (e.g., diameters greater than 10 nm), in certain implementations, smaller frequencies (e.g., frequencies less than 1 kHz) can be advantageously used for such particles. In certain implementations, the particle size and frequency are selected (e.g., optimized) to provide a desired performance (e.g., susceptibility; mobility through the membrane pores).

In certain implementations, the bandwidth of the signal relies on the peak velocity (e.g., the timing) of the mechanical oscillation. FIG. 7A schematically illustrates an example trapezoidal speed profile of a closed loop oscillation system with some hysteresis (e.g., time lag) at zero speed where the motion reverses direction in accordance with certain implementations described herein. In a single oscillation period, the time span of the peak speed is only a portion of the period, so certain implementations described herein have the test line 42a pass through the magnetic field sensor (e.g., apparatus 10) at a peak speed of the oscillation to maximize the signal. In certain such implementations, the signal is a regular train of pulses in synchronization with the speed profile, as schematically illustrated in FIG. 7B.

Figure 7C:
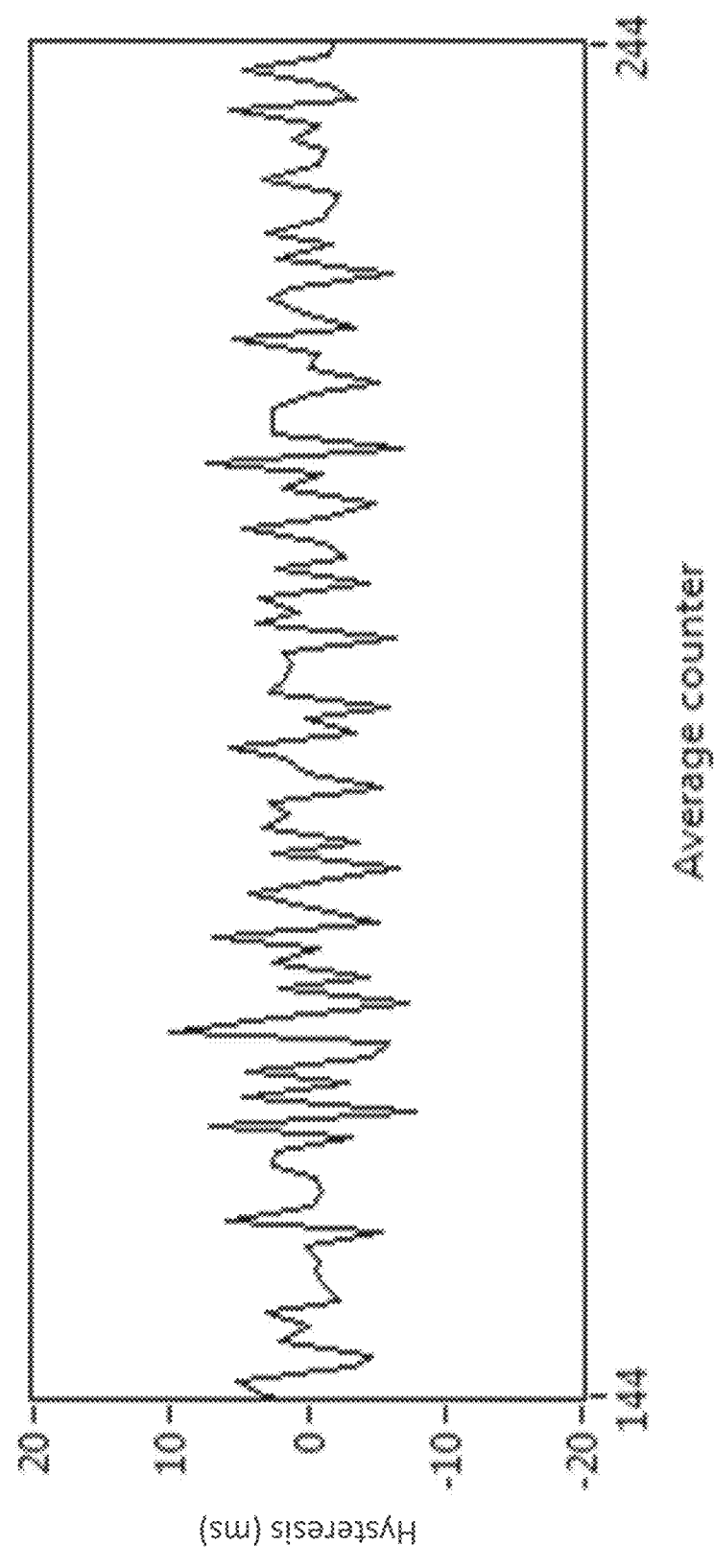
FIG. 7C is a plot of a measured series of mechanical hysteresis (e.g., time lag) of a hundred oscillations driven by a piezoelectric oscillation system at 4 Hz in accordance with certain implementations described herein.

In certain implementations, time averaging of the sensor signal is triggered by a trigger signal generated by the oscillation motion controller (e.g., first controller 60) in synchronization with the oscillation. Such triggered time averaging is equivalent to lock-in amplification for the purpose of noise reduction, and in certain implementations, mechanical hysteresis (e.g., time lag) is reduced (e.g., minimized) by optimizing the closed loop control parameters (e.g., PID) for precise timing of averaging, such that peak broadening, which lowers the signal-to-noise ratio and spatial resolution in the y-profile of the test and control lines 42a, 42b, is reduced (e.g., prevented). FIG. 7C is a plot of a measured series of hysteresis of a hundred oscillations driven by a piezoelectric oscillation system at 4 Hz in accordance with certain implementations described herein. The plot of FIG. 7C shows an average mechanical hysteresis of 2-3 ms, which results in about 1% error in timing, and is acceptable in certain implementations described herein.

Figure 8A:
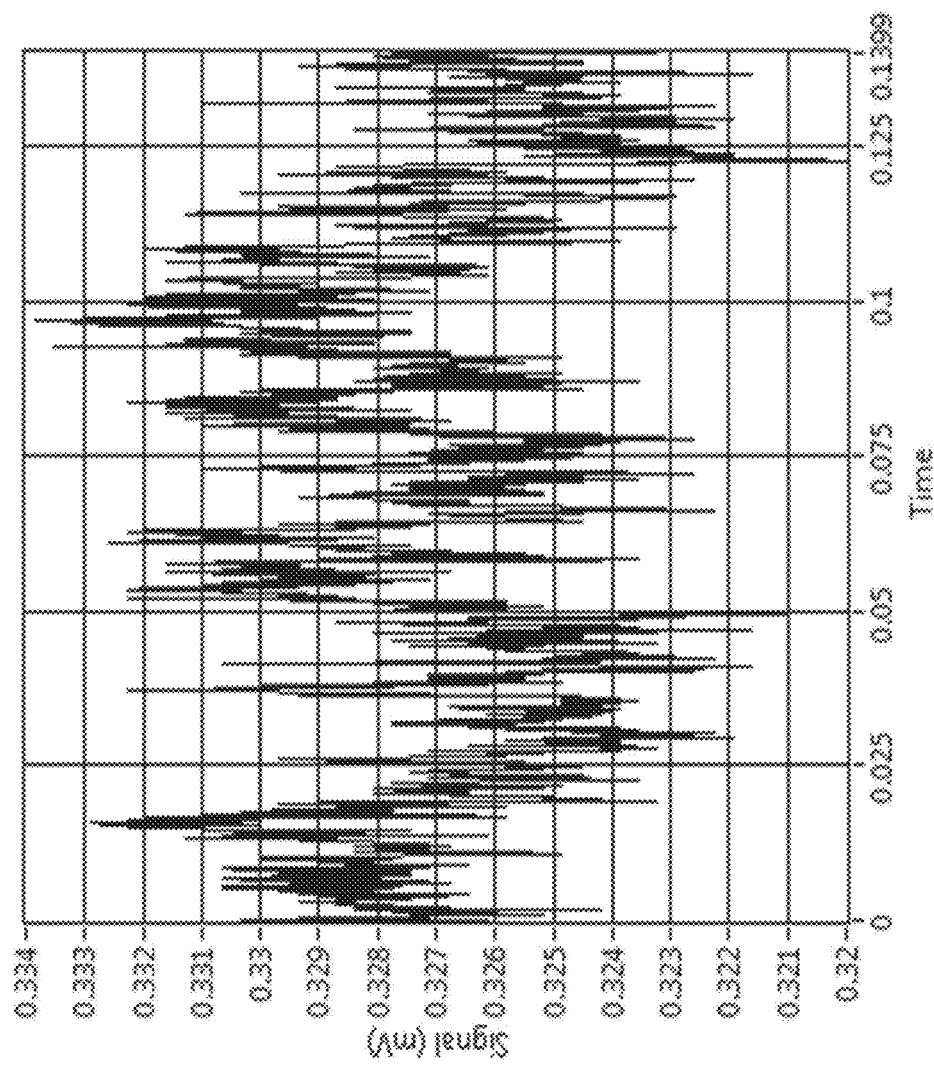
FIGS. 8A-8D demonstrate the effectiveness of noise reduction by the y-direction oscillation and triggered averaging in accordance with certain implementations described herein.
Figure 8B:
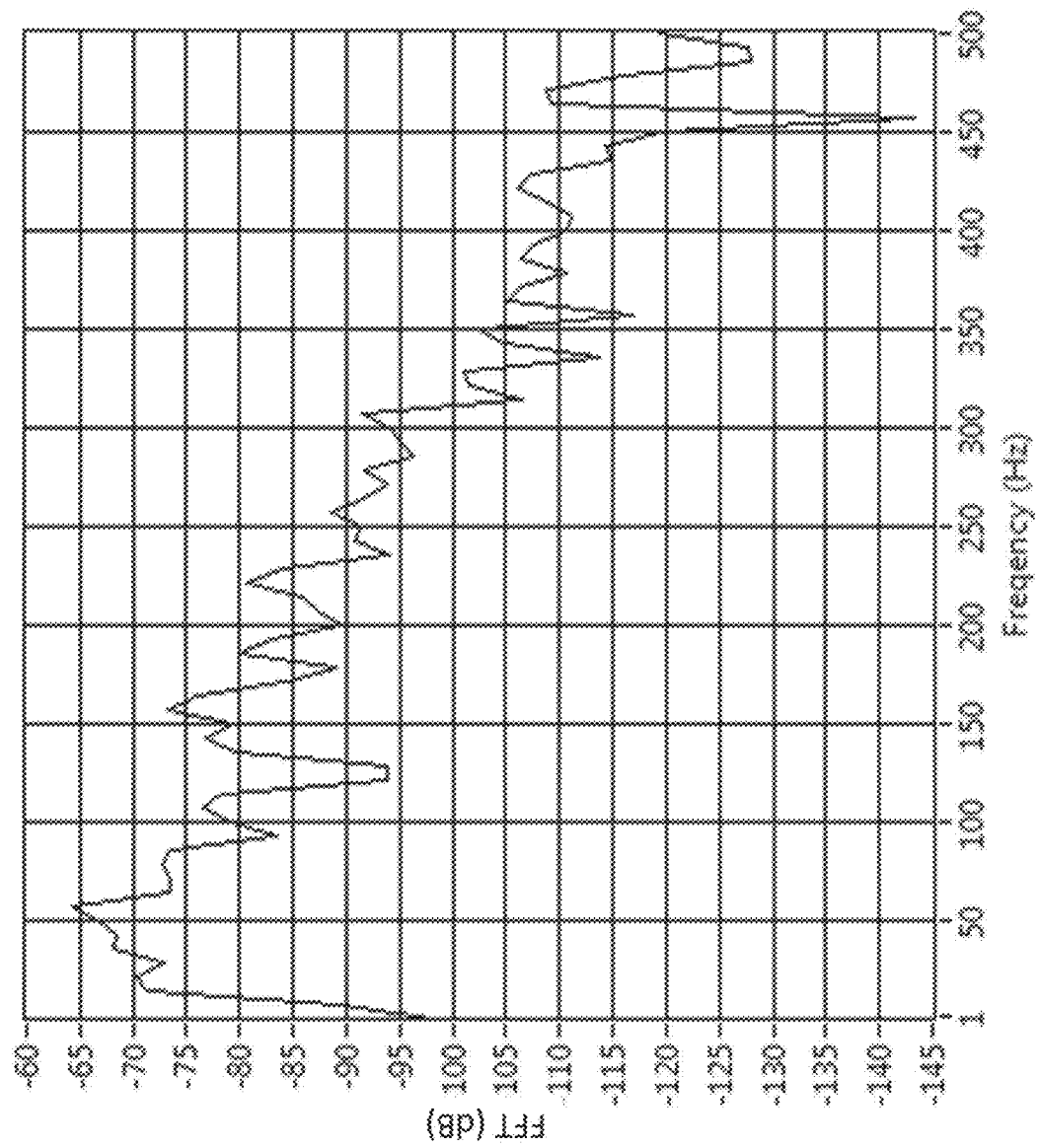
Figure 8C:
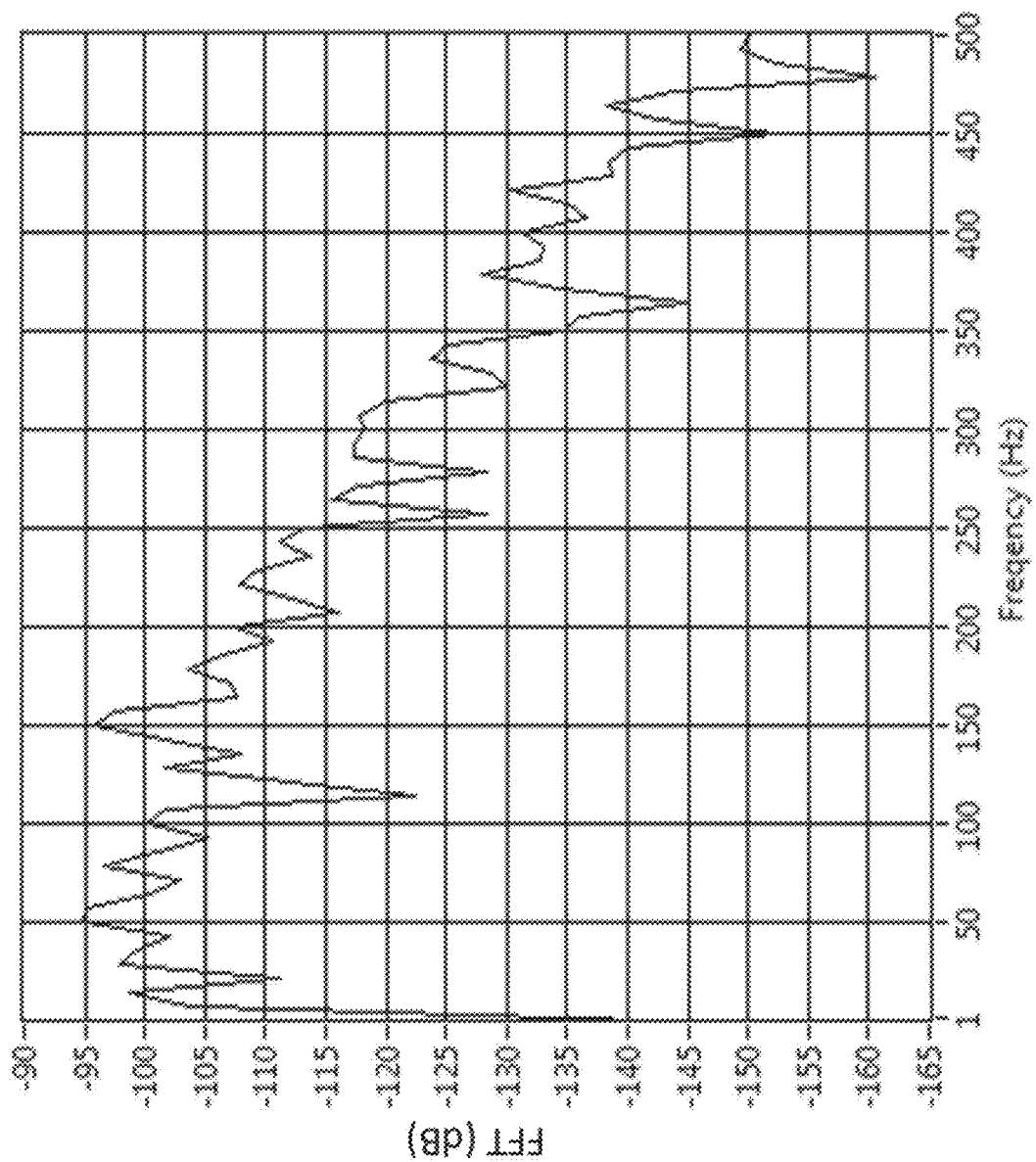
Figure 8D:
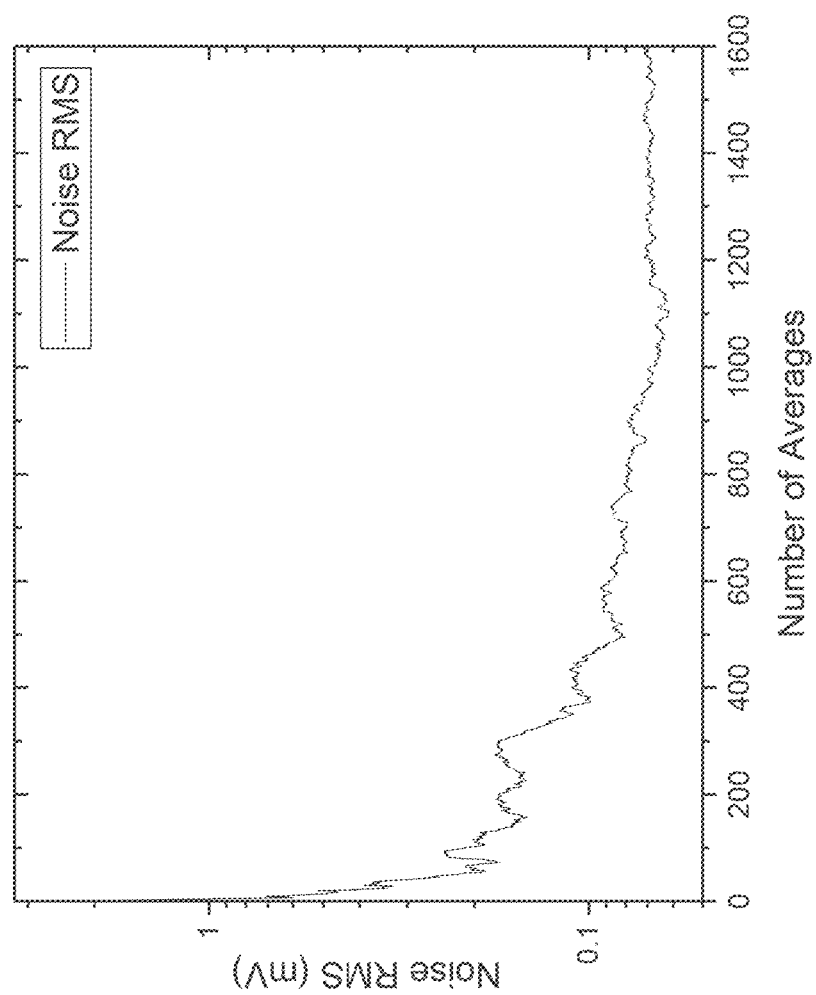

FIGS. 8A-8D demonstrate the effectiveness of noise reduction by the y-direction oscillation and triggered averaging in accordance with certain implementations described herein. For FIGS. 8A-8D, a blank lateral flow strip (e.g., a lateral flow strip without running any assay and free of magnetic particles) was tested to examine the background electric noise. FIG. 8A is a plot of a raw signal, displaying the typical 1/f type of noise superimposed with high frequency noise. FIG. 8B is a plot of the fast Fourier transform (FFT) noise spectrum of the raw signal, where the noise level at 50 Hz is −65 dB. FIG. 8C is a plot of the FFT noise spectrum of the signal after 1000 averages, where the noise level at 50 Hz drops to −95 dB, illustrating the effectiveness of the noise reduction scheme in certain implementations described herein. FIG. 8D is a plot showing the quick drop of the root mean square (RMS) value of noise with an increasing number of averages, which plateaus after 1000 times. With an oscillation frequency of 4 Hz, the measurement takes 4 min to finish, which is sufficiently fast for a rapid test.

Figure 9A:
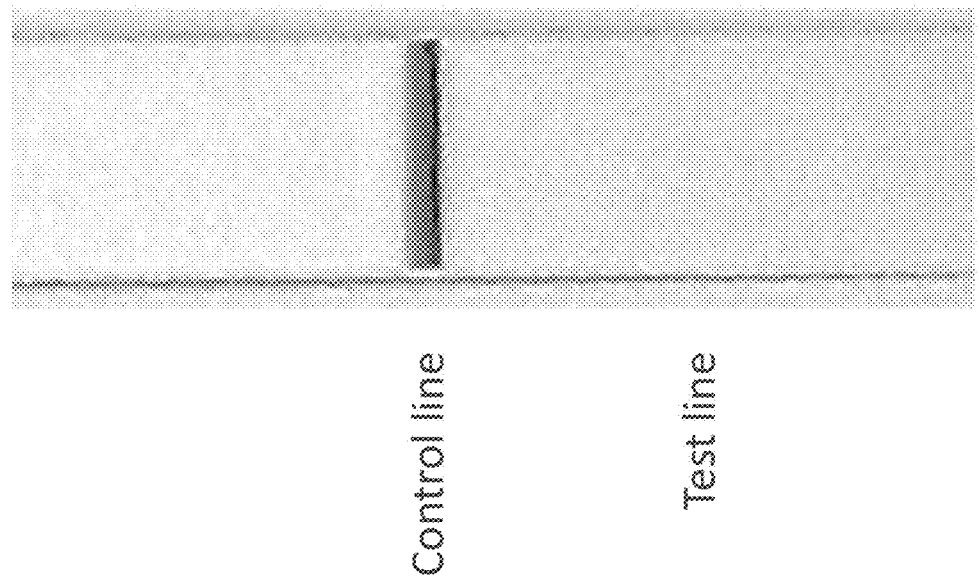
FIGS. 9A-9C show a demonstration of the high sensitivity of an assay of human chorionic gonadotropin (hCG) in accordance with certain implementations described herein and FIG. 9D is a plot of the FFT spectrum of the voltage signal.
Figure 9B:
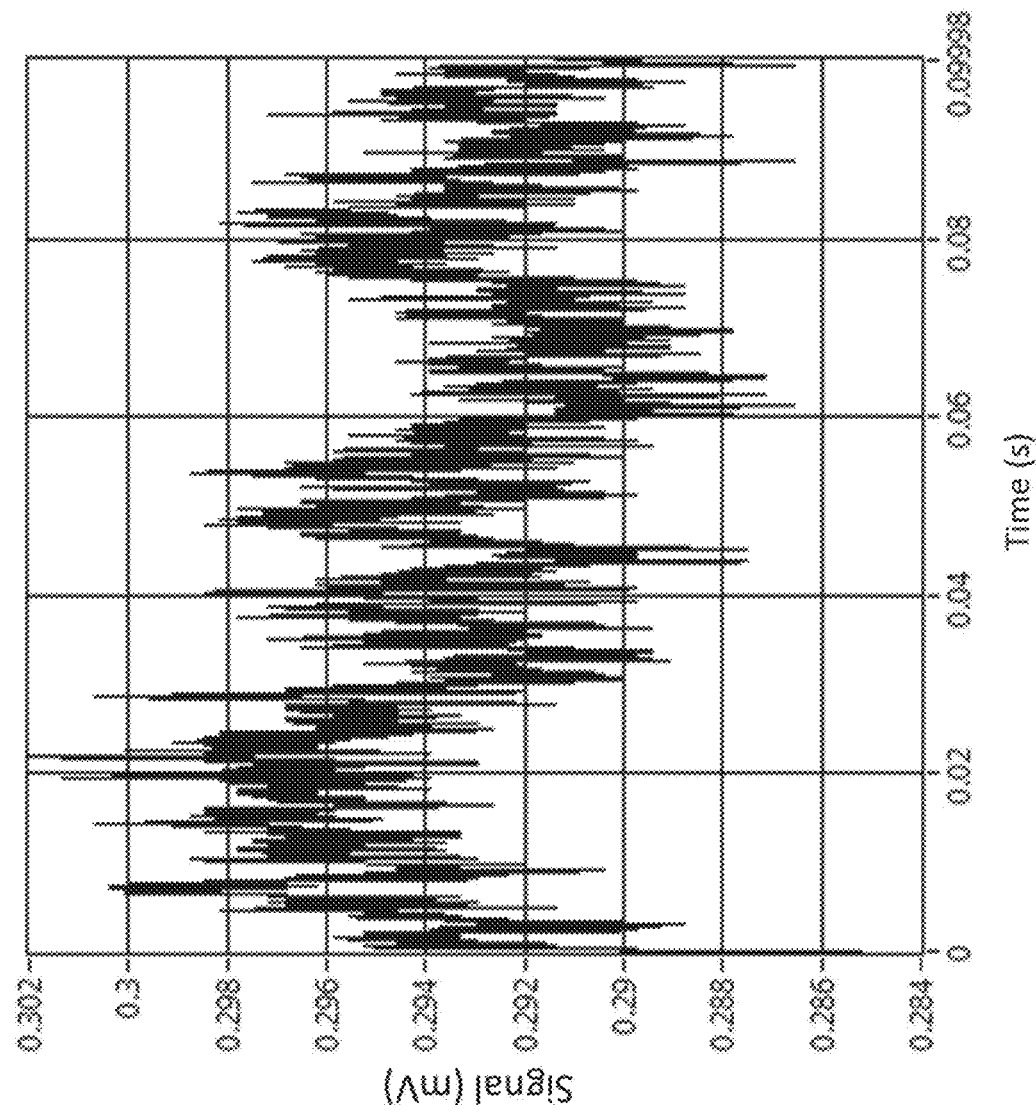
Figure 9C:
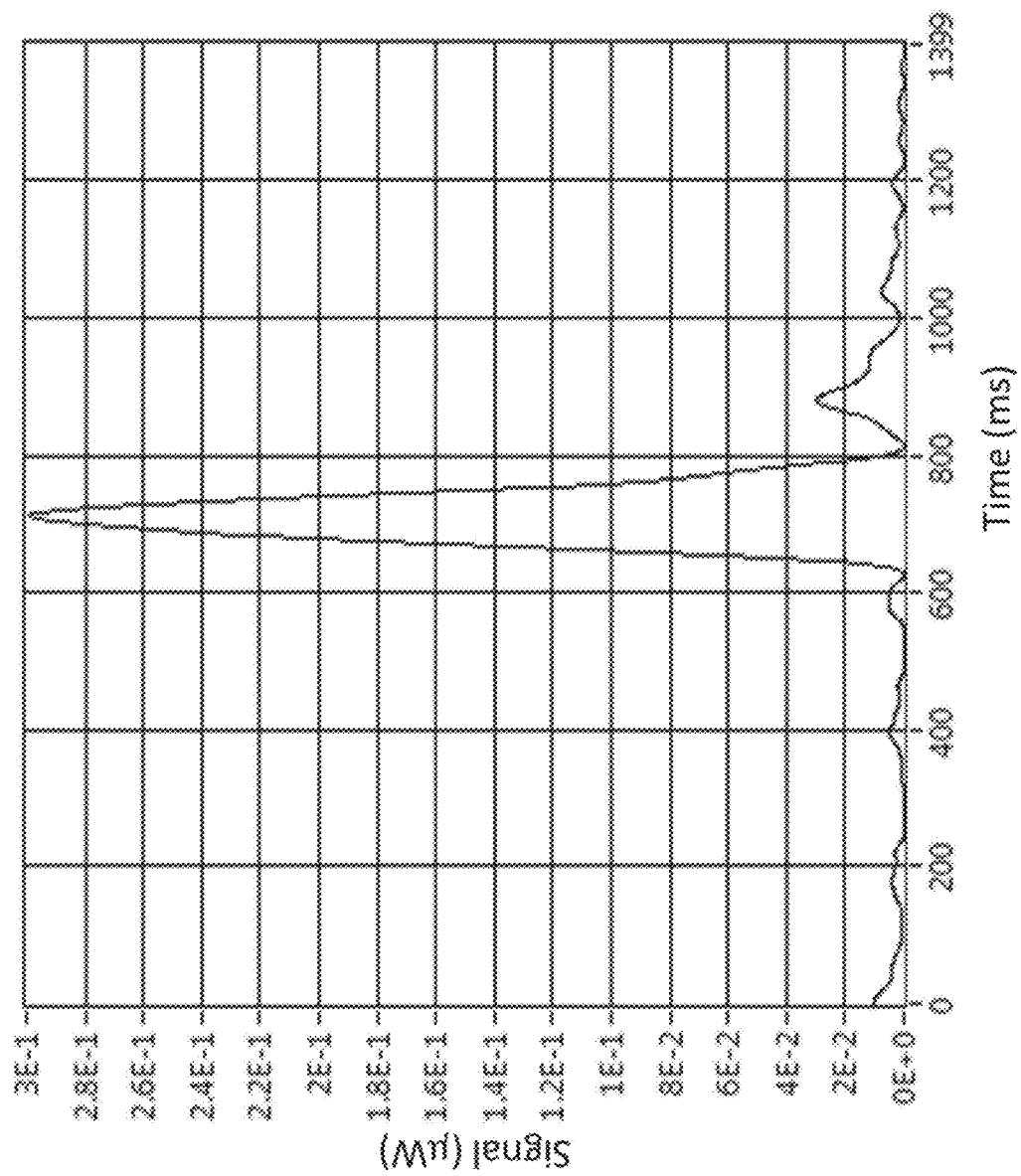
Figure 9D:
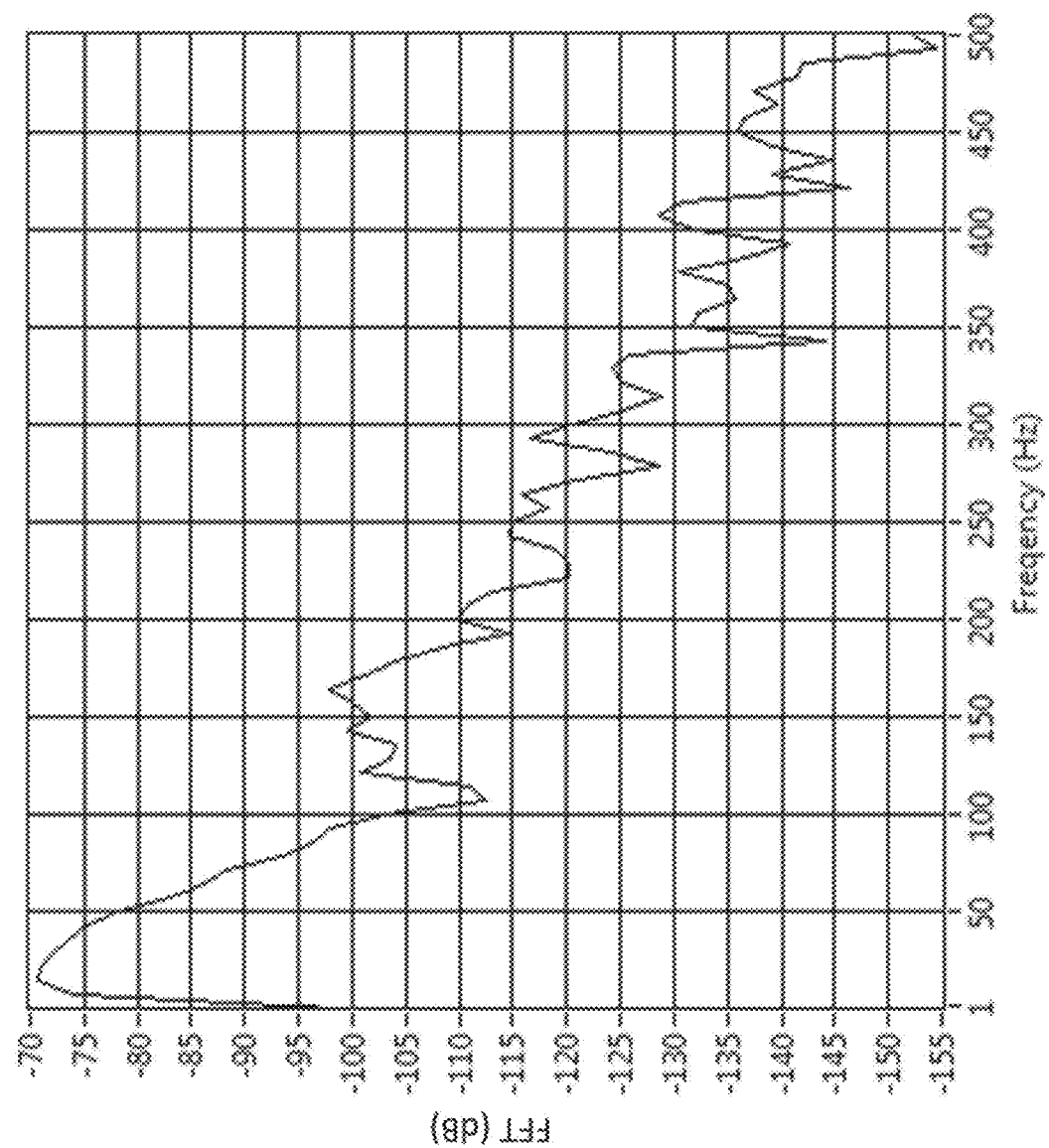

FIGS. 9A-9C show a demonstration of the high sensitivity of an assay of human chorionic gonadotropin (hCG) in accordance with certain implementations described herein. FIG. 9A is a photograph of a test strip with an hCG concentration of 0.1 ng/ml in the sample solution. At the concentration of 0.1 ng/ml, the lateral flow test line 42b is completely invisible to human eyes. FIG. 9B is a plot of the raw sensor signal dominated by 1/f noise and high frequency noise, with the test line signal deeply buried in the noise. FIG. 9C is a plot of the recovered test line signal, obtained by following the noise reduction techniques described herein. To be consistent with optical sensors, such as photodiodes, whose output is linearly related to energy, the signal reported herein is the electric power in watts, calculated as $V^2/R$, where V is the voltage signal amplitude and R is the sensor's impedance. The scheme of mechanical oscillation modulation and synchronized time averaging in certain implementations described herein works satisfactorily such that the recovered test line signal is a clean sharp peak as shown in FIG. 9C. FIG. 9D is a plot of the FFT spectrum of the voltage signal, showing a clear peak in the frequency domain, peaking at about 25 Hz, with a half width of about 50 Hz, and a good signal-to-noise ratio of 30 dB. The method in accordance with certain implementations described herein can detect down to 0.01 ng/ml of hCG. Such sensitivity is superior by two orders of magnitudes to the hCG assays previously reported, which include both TMR sensing (see, e.g., Lei et al. cited herein) and fluorescence sensing (see, e.g., U.S. Pat. No. 9,488,585).

Figure 10:
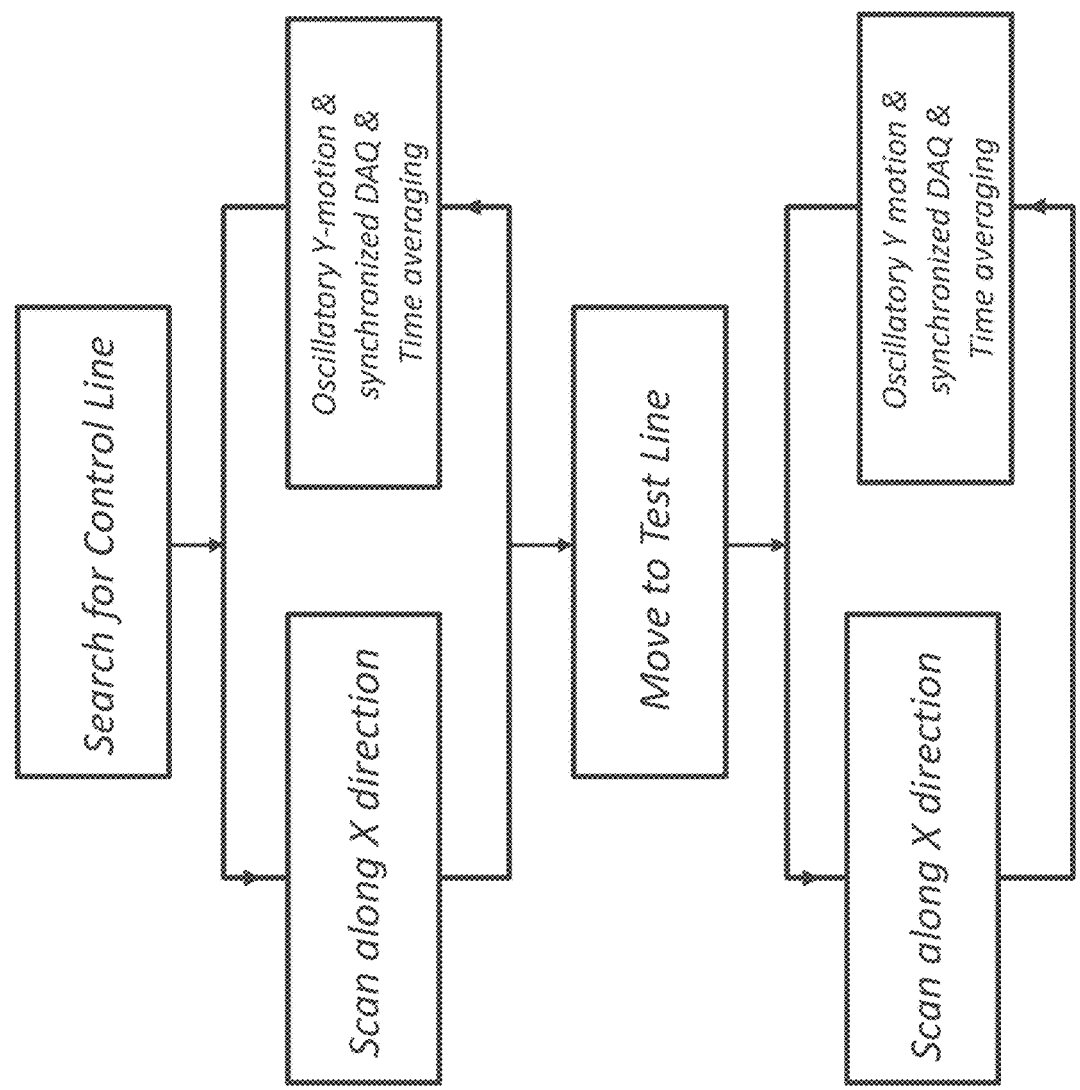
FIG. 10 schematically illustrates an example geometric setup and block diagram of the motion program in accordance with certain implementations described herein.
Figure 10:
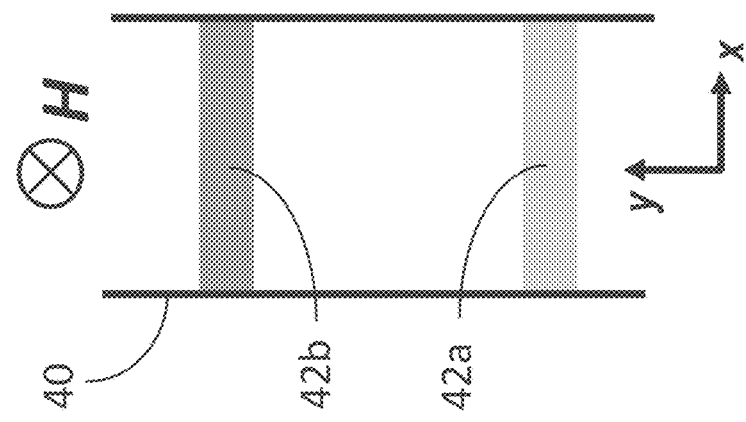

In certain implementations, the linear stepper (or DC) motor sub-stage 52 also provides scanning motion along the test and control line (e.g., along the x-direction). The advantage of the small size of MR sensors 20 in obtaining spatially resolved signals is demonstrated by a programmed x-y scanning of the membrane 40 relative to the magnetic field sensor 20. FIG. 10 schematically illustrates an example geometric setup and block diagram of the motion program in accordance with certain implementations described herein. The membrane 40 has a test line 42a and a control line 42b. Magnetization field H is perpendicular to the plane of the membrane 40. In certain implementations, the motion control program automatically searches for the control line 42b in the upper half of the membrane 40 by determining the location of the signal peak along the y-direction. The membrane 40 then moves stepwise along the x-direction while the stage 50 provides periodic oscillation to produce an x-y scan of the sensor along the control line 42b. The program then moves the membrane 40 by a defined distance to the position of the test line 42a and performs the x-y scan along the test line 42a. The scan speed, the step size, and/or the number of triggered averages can vary depending on the signal intensity. In certain implementations, the result is a 2D mapping of the signal of the test and control lines 42a, 42b, which is unavailable with previous magnetic sensing systems in lateral flow assay. As described herein, magnetic particles can be trapped in the lateral flow membrane pores, contributing to nonspecific background signals. Certain implementations described herein advantageously distinguish between bound particles at the test line 42a from the unbound particles in the background, thereby improving the assay specificity, reliability, and quantification.

Figure 11A:
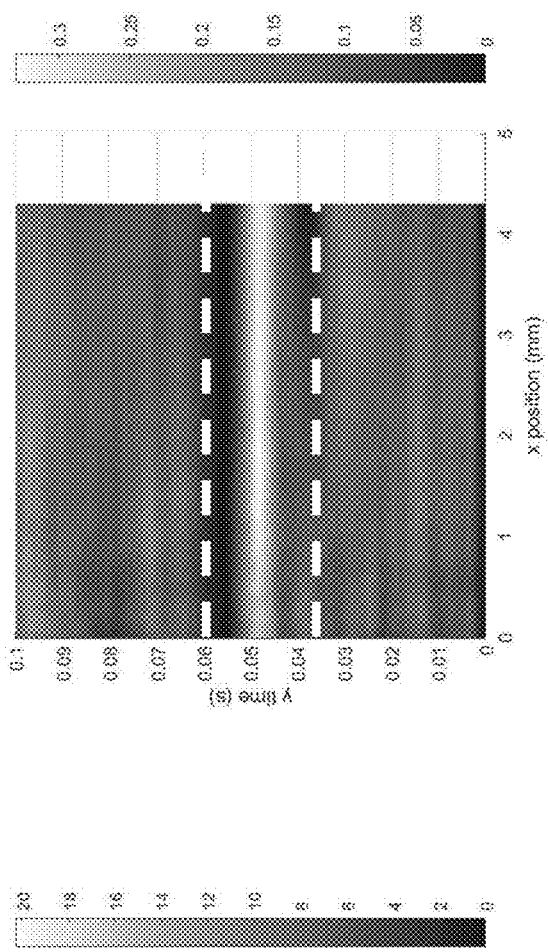
FIGS. 11A-11B show two example magnetic 2D mappings of test lines of an hCG assay with hCG concentrations of 1 ng/ml and 0.1 ng/ml, respectively, in accordance with certain implementations described herein.
Figure 11B:
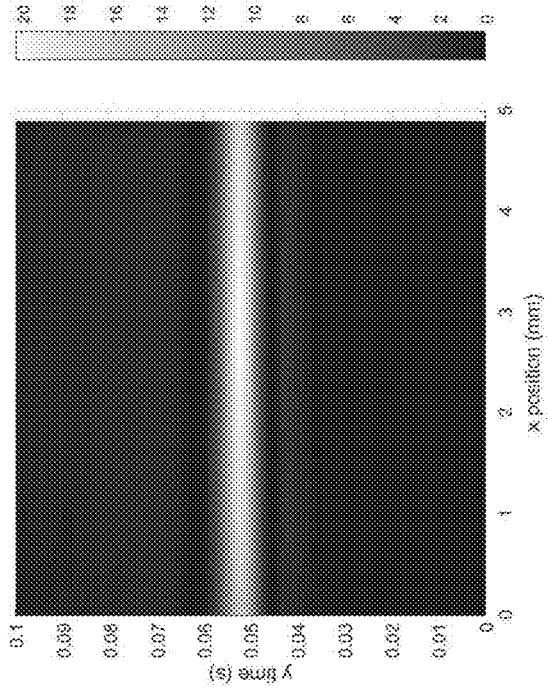
Figure 11C:
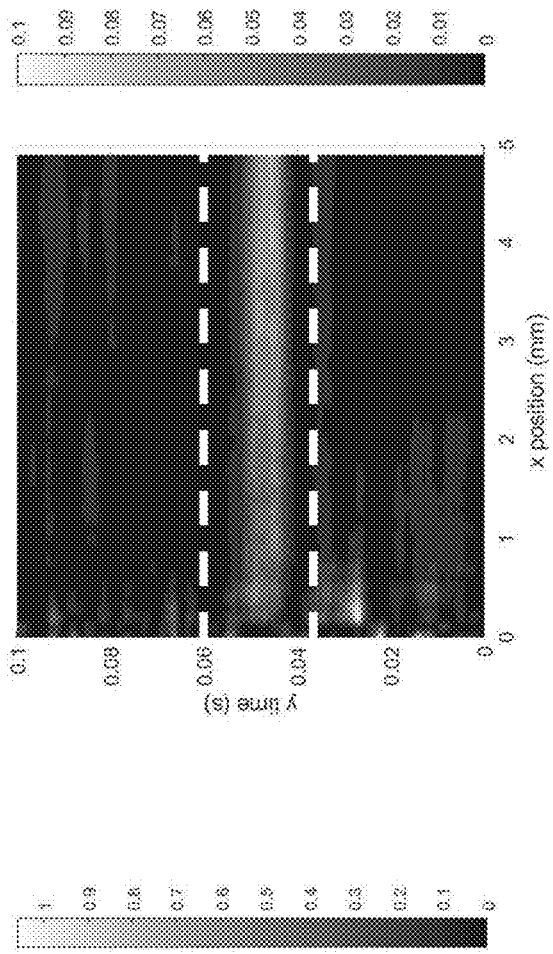
FIGS. 11C-11D show two example magnetic 2D mappings of test lines of a cTnI assay with cTnI concentrations of 1 ng/ml and 0.1 ng/ml, respectively.
Figure 11D:
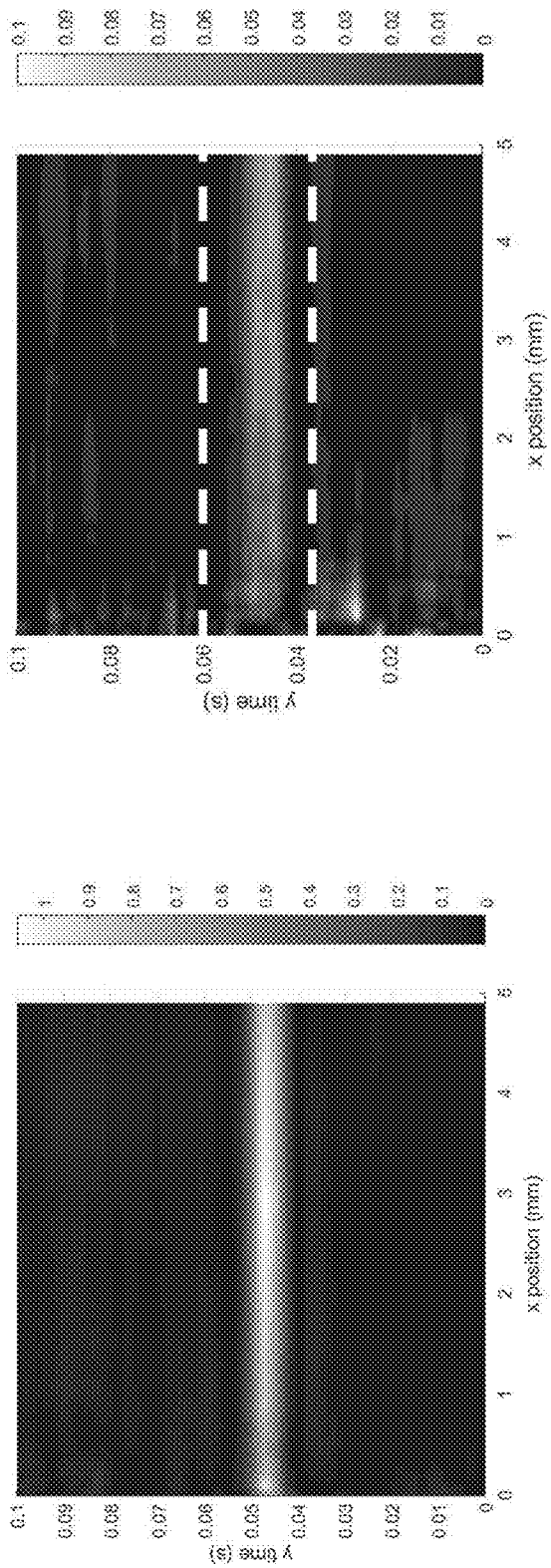

FIGS. 11A-11B show example magnetic 2D mappings of test lines 42a of a hCG assay with hCG concentrations of 1 ng/ml and 0.1 ng/ml, respectively, in accordance with certain implementations described herein. FIGS. 11C-11D show two example magnetic 2D mappings of test lines of a cTnI assay with cTnI concentrations of 1 ng/ml and 0.1 ng/ml, respectively, in accordance with certain implementations described herein. The scan in the x-direction (e.g., along the test line 42a) moves in steps of 0.1 mm, each step being given 50 triggered averages in synchronization with the oscillation in the y-direction (e.g., perpendicular to the test line 42a). The gray scale represents the signal intensity, the scales of which (in units of electric power) are shown by the scale bars. The smearing background in FIG. 11B outside the test line region (marked by the two dotted lines) are likely due to unbound magnetic particles trapped in the membrane 40. In the cTnI assay, an additional washing step is adopted to reduce (e.g., remove; chase away) the unbound magnetic particles after the assay. As a result, FIG. 11D of the same antigen concentration shows negligible smearing background. The test line of FIG. 11A was visible to the naked eye, while the other three test lines of FIG. 11B-11D were invisible to the naked eye. More details of the two assays, including photos of the membranes, are described in the sections describing Example 1 and Example 2. Also, while the number of averages of 50 in these examples does not fully achieve the noise reduction capacity demonstrated in FIG. 8D, a larger number of averages can be used in certain implementations if higher sensitivity is desired (e.g., with correspondingly longer acquisition time). These examples highlight that, in certain implementations, magnetic sensing is highly sensitive to low antigen concentrations where the test lines are invisible to the naked eye, and can show features previously unavailable (e.g., unbound magnetic particles trapped in the membrane and/or non-uniformities in test line preparation such as during printing of the capture antibody), thus helping lateral flow assay developers identify hidden factors and assay manufacturers improve quality control.

The 2D mapping method described herein is not limited to applications measuring the test and control lines 42a, 42b in lateral flow assay. In a plural of assay formats, magnetic nanoparticles can be immobilized on 2D arrays of dots spotted on a solid surface. The advantage of 2D array of dots are that each dot can be designed to have biological detection specific to a different analyte, providing multiplexed assays.

Assay Examples

The following description provides information regarding various components of certain implementations described herein, including the sample, detection and capture ligands, and magnetic probe, as well as examples of assays and comparisons with standard colorimetric lateral flow readers.

Figure 12:
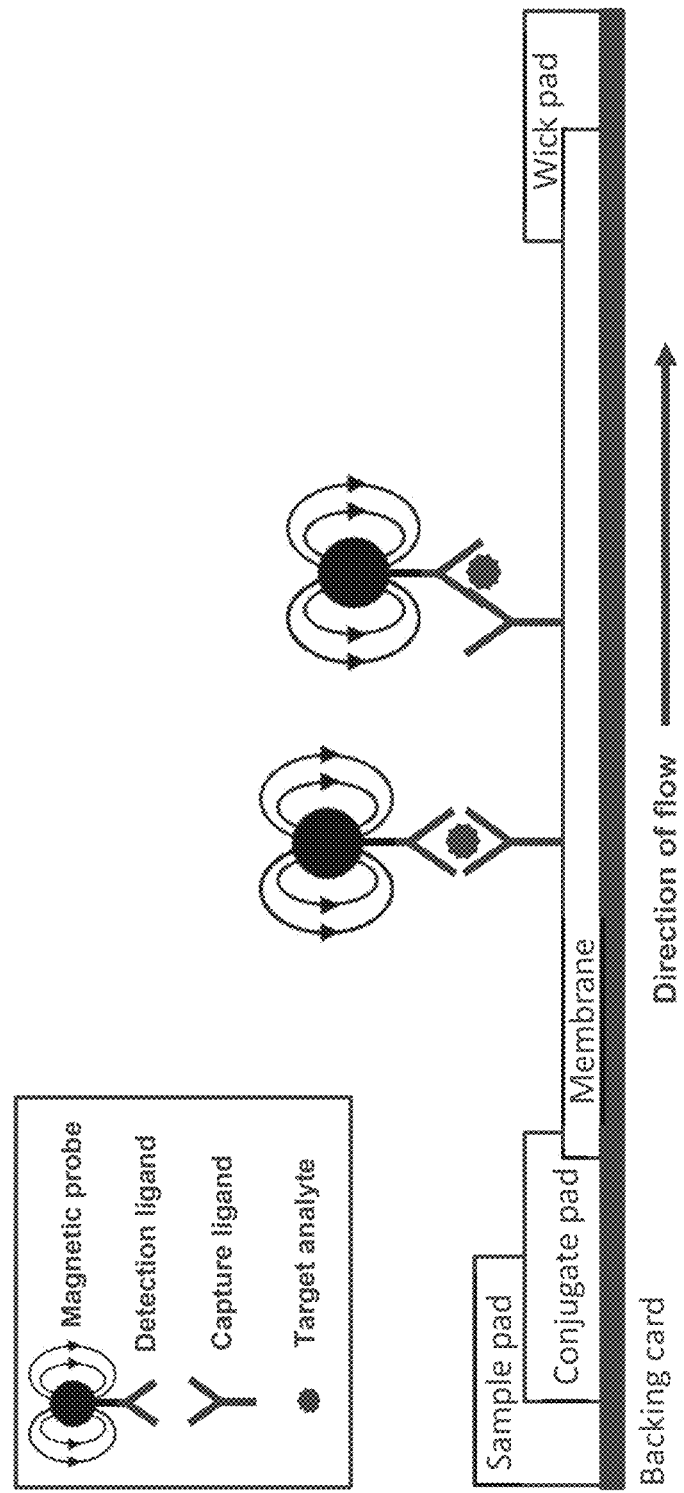
FIG. 12 schematically illustrates a lateral flow assay in accordance with certain implementations described herein.

FIG. 12 schematically illustrates a lateral flow assay in accordance with certain implementations described herein. The components include a membrane 40, detection and capture ligands, magnetic probes, a wicking pad, a backing card, a sample pad, and a conjugate pad. FIG. 12 also schematically illustrates a target analyte, which may or may not be present in a sample of interest. The lateral flow assay can also be housed within a cassette 44 or holder to keep all the components together and facilitate flow. In certain implementations, only the membrane 40, detection and capture ligands, and magnetic probes are included for the assay, while certain other implementations also include a wicking pad and a backing card, and may include the other components as warranted.

During testing, a sample (as described herein) is either applied to the sample pad or directly onto the membrane (e.g. by dipping the membrane 40 into the sample) and the liquid is pulled up through the assay via capillary action maintained by the presence of the wicking pad. If the conjugate pad is present, the sample can then encounter the magnetic probe functionalized with a detection ligand. If there is no conjugate pad in the assay, the magnetic probe can be mixed in with the sample along with a buffer. If analyte is present in the sample, it can bind to the magnetic probe to form a binding complex (as described herein). As the binding complex continues to move through the assay, it can be immobilized at a capture zone by the capture ligands therein, as described herein, and the assay can be analyzed before or after the assay has dried.

The lateral flow assay can have one or more capture zones. In some implementations, there can be two capture zones. The first capture zone can be designed to indicate the presence or absence of a target analyte (e.g., test line), and the second capture zone can be designed to indicate that the assay is operational (e.g., control line). For example, in a sandwich assay format, as shown in FIG. 12, the test line capture zone can comprise an immobilized capture ligand specific to the target analyte. In certain implementations, there can be two test lines which are each designed to indicate the presence or absence of a distinct (e.g., different) target analyte. Other possible assay formats for assaying multiple target analytes simultaneously can be used in other certain implementations.

The lateral flow assay can include a sample which may or may not contain an analyte of interest. Herein, the terms "target analyte," "analyte of interest," and the like refer to a molecule or moiety that may have some significance when present in the sample. For example, a target analyte can be a DNA fragment from a pathogen that may contaminate food. The target analyte can include many molecules depending on the intended application of the lateral flow test. For example, for human or animal diagnostic use, the target analyte can be a biological molecule, such as an antibody or other protein; a peptide; a nucleic acid, including single- and double-stranded DNA and RNA, and their fragments (e.g., oligos); a polysaccharide; a small molecule such as an inhibitor or hormone; or a combination thereof, such as a protein/RNA complex. In certain implementations, identifying the presence or absence of such molecules in a sample can be indicative of diseases, infectious or otherwise, or other conditions which can impact the body, such as pregnancy or genetic mutations. As another example, in testing for contamination of food, water, soil, air, or other environmental material, the analyte of interest can include foodborne pathogen markers, such as viral RNA; small molecules, including toxins and organic compounds; or heavy metals. Certain implementations advantageously quickly identify environmental hazards. As a final example, the analyte of interest can be synthetically-derived, as with testing for drugs of abuse. In each of these examples, the use of a lateral flow assay can be desirable because it can enable faster results (e.g., time of measurement less than 6 minutes) than conventional testing methods.

The sample applied to the lateral flow strip may or may not contain the analyte of interest. The sample may or may not be biologically derived and may contain many distinct (e.g., different) molecules or moieties aside from the target analyte. In certain implementations, the sample can include material derived from humans, animals, plants, fungi, yeast, bacteria, tissue culture, viral cultures, or combinations thereof. The sample can also include extractions from food, water, soil, air, or other environmental material, or can include extractions from synthetic materials. Examples of human-derived samples include but are not limited to: whole blood, serum, plasma, urine, stool, saliva, cheek swabs and other tissue samples, perspiration, and more. In certain implementations, the sample can be manipulated in some way to make it compatible with the lateral flow assay format, or to remove interfering molecular entities. For example, whole blood can be filtered so that only serum is applied the membrane, or food samples can be dissolved so that their component molecular entities can flow up the strip. The sample can also be modified with additives, which can either be added directly to the sample before testing or included on the sample pad. Such additives can be used to regulate pH (e.g., buffers), to support antibody binding (e.g., salts), or to minimize non-specific interactions (e.g., surfactants, blockers), among other purposes.

In certain implementations, the sample can comprise components artificially mixed to replicate one or more of the clinically, environmentally, or otherwise relevant samples listed herein. Certain implementations use such an artificial sample as a tool for assay development. In such samples, the concentration of the target analyte can be controlled in order to test possible assay outcomes. As with other samples, artificially-derived samples can include many distinct molecules or moieties aside from the target analyte. In the case of assay development, such inclusions can provide information about cross-reactivity or interference caused by their presence.

The detection and capture ligands can be any molecules, whether biologically or synthetically derived, which can strongly and/or specifically bind to the analyte of interest. In certain implementations described herein, the detection ligands refer to those analyte binding molecules attached to the probes (e.g., the magnetic particle probes). The process of attaching detection ligands to the probes is also known as conjugation or labeling. The capture ligands refer to those analyte binding molecules localized (e.g., by printing) at the capture zones on the membrane 40, where specific binding of analyte occurs complementary to the detection ligand-analyte binding. As used herein, the terms "specifically bind," "specific binding," and the like have their reasonable ordinary meanings, including but not limited to that one binding molecule or moiety can preferentially bind to a second molecule or moiety relative to other molecules or moieties in a solution or sample. For example, an antibody can specifically bind a certain antigen.

The exact composition of the detection and capture ligands can depend on the analyte of interest and the type of assay (e.g. sandwich, competitive, etc.). In a competitive assay, a detection ligand can simply comprise the analyte of interest. In various implementations, the assay can follow the convention of a sandwich assay where the detection and capture ligands bind to the analyte of interest complementarily.

In certain implementations, the detection and capture ligands can be one member of a binding pair. As used herein, the term "binding pair" has its reasonable ordinary meaning, including but not limited to a pair of complementary molecules or moieties that specifically bind to one another and form a binding complex. The second member of the binding pair can be the analyte, the magnetic probe, or other assay components, or can be used to modify those components. In this way, the binding pair can be used to form a binding complex between the analyte, the magnetic probe, and the assay. The binding complex can then allow the analyte to be detected in accordance with certain implementations described herein. Examples of suitable binding pairs include but are not limited to: antibody/antigen pairs, ligand/receptor pairs, enzyme/substrate pairs, biotin/avidin, biotin/streptavidin, and antigen- or ligand-binding fragments of antibodies or receptors. The binding pair for a given assay can be determined by the analyte of interest and the type of assay.

In certain implementations, the detection and capture ligands can be antibodies, and the target analyte can be an antigen. In a sandwich assay, the capture antibody can bind to one epitope of the antigen which is complementary to (e.g., non-overlapping) the epitope which binds to a detection antibody on the magnetic probe. In this way, the antigen can bind to both the magnetic probe and the capture ligand and thus be detected at the test line.

The magnetic probes used in certain implementations described herein are magnetic particles, with magnetic properties as described herein. The magnetic probes can be conjugated with detection ligands in order to specifically bind to the target analyte. In certain implementations, the conjugation can comprise one member of a binding pair, as described herein as the detection ligands. The capture ligand printed at the capture zones can be part of a complementary binding pair to that of the detection ligand, allowing the target analyte to be bound to both the capture ligand and detection ligand on the magnetic probe.

In certain implementations, the magnetic probe can be functionalized with specific binding moieties (e.g., detection ligands) via covalent binding. Such process is also referred to as functionalization. Covalent binding can be achieved either by reaction of the binding moiety with the magnetic probe surface or by reaction of the binding moiety with functional groups (e.g., —COOH) that have previously been added to the magnetic probe's surface. Covalent functionalization can be stable over a wide range of assay conditions. In other implementations, specific binding moieties can be stably and non-covalently associated with the magnetic probe surface under the assay conditions. Non-covalent association mechanisms can include non-specific adsorption, electrostatic interactions, hydrophobic interactions, hydrogen bonding interactions, or combinations thereof.

In some implementations, the surface of the magnetic probe can be modified prior to functionalization with a specific binding moiety. In some instances, the surface of the magnetic probe can be coated or functionalized with a layer designed to facilitate the functionalization with a specific binding moiety. For example, a layer of dextran, polyethylene glycol (PEG), or other similar substance can facilitate the association of a specific binding moiety with the magnetic probe surface. As another example, polymers end functionalized with carboxylic groups can be bound to the magnetic probe surface to allow an EDC/NHS reaction to covalently bind a protein (e.g., streptavidin). In some implementations, the surface can be additionally modified with a surfactant configured to improve the solubility of the magnetic probe. In some implementations, the surface of the magnetic probe can be modified with a passivating layer, such as polymers, or small proteins such as bovine serum albumin (BSA), with the intention of improving the chemical stability of the magnetic probe (e.g., prevent aggregation).

In certain implementations, the magnetic probe can be blocked after conjugation with a specific binding moiety in order to reduce or prevent non-specific interactions. As used herein, "non-specific interactions" has its reasonable ordinary meaning, including but not limited to binding between assay components (e.g., magnetic probe and capture ligand) which are not intended to interact. Non-specific interactions can lead to false test results (e.g., false positives in a sandwich assay format) and are therefore avoided inasmuch as possible. Blocking of the magnetic probe can involve the association of an additional, non-reactive molecule or moiety with the probe's surface. Example blocking moieties include but are not limited to: bovine serum albumin (BSA), Tween-20, Triton X-100, casein, "irrelevant" immunoglobulins (e.g., immunoglobulins that do not bind to other assay components), fish skin gelatin, polyethylene glycol (PEG), nonspecific serum (e.g., horse or fish), commercial blockers, or others, including combinations thereof. The optimal blocking formulation can be determined empirically during assay development.

In some implementations, the magnetic probe can be applied to a conjugate pad. For example, the magnetic probe can be applied in a solubilized state and then dried, with the intention that the magnetic probe will re-solubilize immediately when it comes in contact with the sample solution. The magnetic probe solution can be applied to the conjugate pad via spraying, pipetting, dipping, or other methods. In certain implementations, the magnetic probe solution that is applied can contain a low concentration buffer for pH control and a low concentration of a carbohydrate to enhance re-solvation. The optimal contents, application volume, and application method may be determined empirically during assay development.

Several representative lateral flow assays can be used to demonstrate the improved sensitivity of certain implementations described herein over conventional optical-based assay readers known as colorimetric readers. The term "limit of detection (LOD)" in these examples has its reasonable ordinary meaning, including but not limited to the lowest concentration at which a target analyte can be detected and at which a sample or solution can be unequivocally distinguished from a solution without the target analyte. The term "sensitivity" has its reasonable ordinary meaning, including but not limited to that concentration inversely, e.g., a higher sensitivity refers to capability of detecting lower concentration. In some cases, the magnetic probe can bind to the capture zone when the target analyte is not present, called non-specific binding in these examples. A large amount of non-specific binding can lead to decreases in the overall sensitivity of an assay, because it makes a true positive test more difficult to distinguish.

Example 1, hCG Assay

In Example 1, a dose response curve for the pregnancy indicator human chorionic gonadotropin (hCG) was produced. A dose response curve is a plot of assay signal versus antigen concentration which can be used to determine an assay's sensitivity or to quantify the amount of antigen present in a sample. The sensitivity can be defined by the concentration below which the assay signal reaches a saturation point, e.g., the signal does not change or changes very little at the next lowest concentration.

A half-strip lateral flow assay was designed and assembled as follows. The assay included a membrane, two antibody capture zones, antibody-functionalized magnetic nanoparticles, a backing card, and a wicking pad. The nitrocellulose membrane had a capillary flow rate of 120 s (e.g., to flow a distance of 4 cm). The first capture zone was an anti-hCG primary antibody and the second was a goat anti-mouse secondary antibody. Each capture zone antibody solution was applied to the membrane at a concentration of 1 mg/mL. They were sprayed in two lines across the strip with 1 cm between them. Subsequent preparation steps of baking, blocking, drying, assembly with backing cards and wick pads, cutting, etc. followed the standard practice in lateral flow assay.

Antibody-conjugated magnetic gold-iron alloy (Au—Fe) nanoparticles were used as the magnetic probe in this assay. The average size of the magnetic nanoparticles was 150 nm, measured by dynamic light scattering (DLS). The nanoparticle solution had a particle mass concentration of 3 mg/ml. Surface functionalized magnetic nanoparticles were mixed in a 1:1 volumetric ratio with a 1 mg/mL solution of a mouse anti-hCG primary antibody complementary to that used for the first capture zone. After the reaction, the nanoparticles were blocked with bovine serum albumin (BSA). The nanoparticle-antibody conjugates were centrifuged to remove excess reactants and re-suspended in a buffered solution.

To produce a dose response curve, seven solutions containing varying concentrations of the antigen hCG were made, from 100 ng/mL to 0 ng/mL. The hCG was diluted in a buffer containing a small amount of Tween-20, designed to reduce or prevent nanoparticle aggregation and non-specific binding. 50 µL of each antigen solution was pipetted into a separate well of a 96-well plate. 10 µL of the conjugated magnetic particles (at ~1.2 mg/mL) were then added to each well. One lateral flow strip was placed into each well such that the membrane was partially submerged in the mixture and the wicking pad stuck up out of the well. The liquid was allowed to run up the strip for 15 minutes, and then the strip was removed and allowed to dry for at least 1 hour before further analysis.

Figure 13:
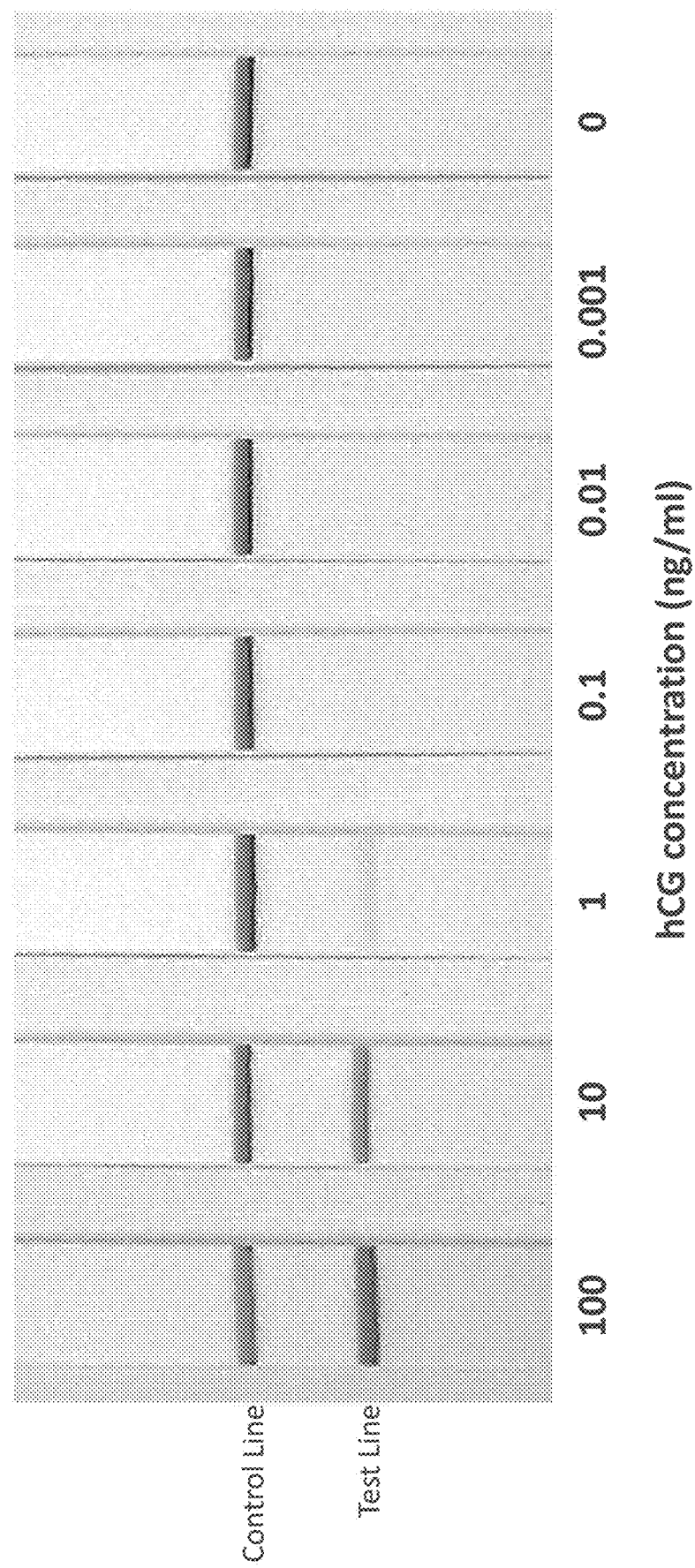
FIG. 13 illustrates a photograph of seven resulting lateral flow strips of different hCG concentrations.

FIG. 13 illustrates a photograph of the seven resulting lateral flow strips of different hCG concentrations. The gray line in the lower half of the strip is the first capture zone (e.g., the test line), which binds the hCG antigen and is visible only when antigen of sufficient concentration is present and binds to the magnetic probe. The dark line in the upper half of the strip is the second capture zone (e.g., the control line) which binds directly to the antibody-functionalized magnetic nanoparticles and is used to indicate that the test is functioning properly. As can be seen, the visibility of the test line quickly drops off as the hCG concentration decreases. At 1 ng/ml, the test line is barely visible to the naked eye. At 0.1 ng/mL, the color can barely be detected by a colorimetric detector (see below).

Figure 14A:
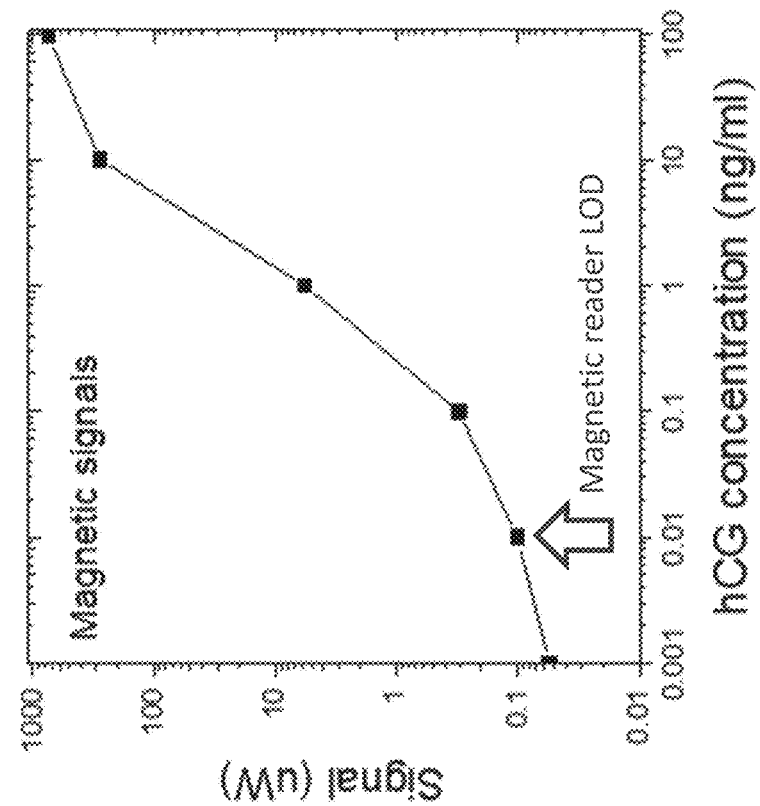
FIGS. 14A-14B illustrate plots of the dose response curves produced using the colorimetric reader and in accordance with certain implementations described herein, respectively.
Figure 14B:
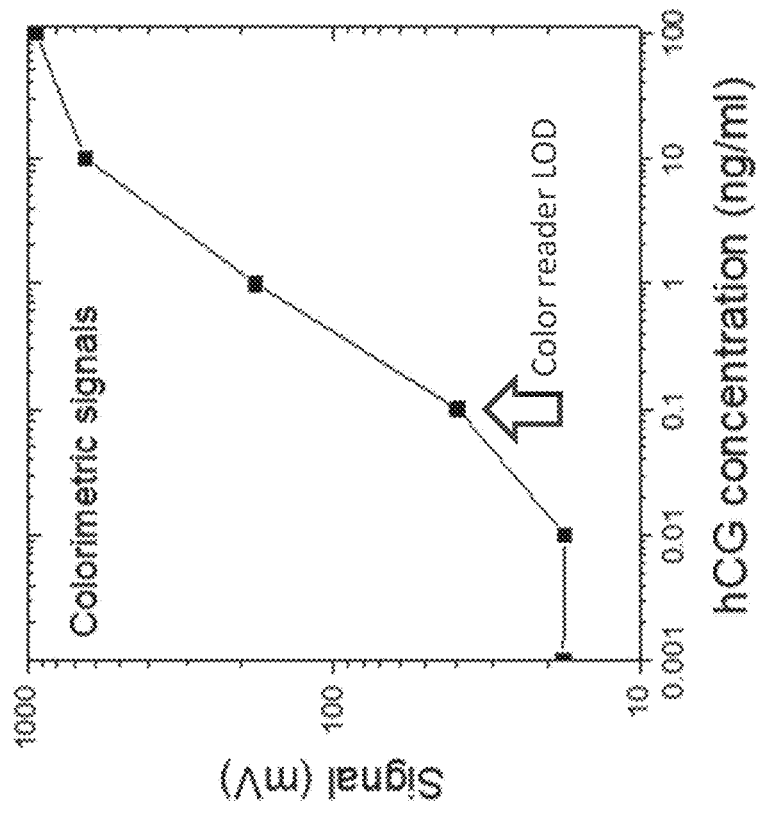

The assay test strips were measured using both a standard colorimetric lateral flow reader and the magnetic reader in accordance with certain implementations described herein. FIGS. 14A-14B illustrate plots of the dose response curves produced using the colorimetric reader and in accordance with certain implementations described herein, respectively. The curve produced with the colorimetric reader plateaus at a concentration of 0.01 ng/mL, thus the limit of detection (LOD) is 0.1 ng/mL, or 100 pg/mL. The curve produced in accordance with certain implementations described herein shows no plateau over the concentrations examined. The signal at 0 ng/mL is approximately the same as that at 0.001 ng/mL (0.05 pW). The signal at both of these concentrations can be attributed to nonspecific binding of the magnetic particles to the test line. Since the signal at 0.01 ng/mL (0.1 pW) is significantly higher than the nonspecific binding signal, it is considered the LOD of this hCG assay by the system in accordance with certain implementations described herein, illustrating that the sensitivity of this assay has been improved by one order of magnitude when compared to a standard colorimetric reader, and two orders of magnitude when compared to the naked eye.

The system in accordance with certain implementations described herein has a broader dynamic range of signal of five orders of magnitude compared with the two orders of magnitude from the standard colorimetric reader system. The nonspecific binding signals of the system in accordance with certain implementations described herein (e.g., at 0.001 ng/ml and 0 ng/ml) still have a signal-to-noise ratio greater than 10 (e.g., greater than 20). In the colorimetric reader system, the test lines of these strips are completely beyond detection. Therefore, the sensitivity of the system in accordance with certain implementations described herein is limited by the imperfect binding chemistry that leaves nonspecific binding of magnetic particles at the test line, rather than by the system in accordance with certain implementations described herein.

Example 2. cTnI Assay

In Example 2, a system in accordance with certain implementations described herein was used to produce a dose response curve for the cardiac injury biomarker cardiac troponin I (e.g., cTnI). cTnI and another subunit of the cardiac troponin complex, cTnT, have been established as markers for the diagnosis of acute myocardial infarction (e.g., heart attack) as well as other cardiac injuries. Currently, high-sensitivity cardiac troponin assays have a limit of detection of around 0.01 ng/mL, allowing for the detection of myocardial injury within 1 to 3 hours of symptom onset. Less sensitive assays can only be able to detect such injuries within 3 to 6 hours of symptom onset. Thus, it can be advantageous to have a limit of detection on the order of 0.01 ng/mL for a cTnI assay to be clinically relevant. However, such sensitivity is difficult to achieve in a lateral flow assay utilizing optical measurements. Herein, it is shown that the sensitivity of a cTnI lateral flow assay can be improved using magnetic detector particles in accordance with certain implementations described herein.

Half-strip lateral flow assay strips were produced as described above in Example 1 with several changes. The nitrocellulose membrane had a capillary flow rate of 80 s (e.g., for a distance of 4 cm). The first capture zone (e.g., the test line) was an anti-cTnI primary antibody, applied at a concentration of 1.5 mg/mL, and the second capture zone (e.g., the control line) was a goat anti-mouse secondary antibody, applied at a concentration of 1 mg/mL. The two lines were printed 1 cm apart. Subsequent preparation steps of baking, blocking, drying, assembly with backing cards and wick pads, cutting, etc. followed the standard practice in lateral flow assay.

Magnetic gold-iron alloy (Au—Fe) nanoparticles were conjugated with anti-cTnI primary antibodies and were used as the magnetic probe in this assay. Surface-functionalized magnetic nanoparticles were incubated in a 1:1 volumetric ratio with a 1 mg/mL solution of a mouse anti-cTnI primary antibody complementary to that used for the first capture zone. After the reaction, the particles were blocked with bovine serum albumin (BSA), then centrifuged to remove excess reactants.

For the dose response curve, eight solutions each containing a different concentration of the cTnI antigen were prepared via serial dilutions, from 100 ng/mL to 0 ng/mL. The cTnI was diluted in a running buffer containing a small amount of Tween-20, designed to reduce or prevent non-specific binding. 50 µL of each antigen solution was pipetted into a separate well of a 96-well plate. 5 µL of the conjugates (at about 1 mg/mL) were then added to each well and the mixture was stirred with a pipette tip. One lateral flow strip was placed into each well with the membrane partially submerged and the wicking pad sticking up out of the well. The liquid was allowed to run up the membrane for 10 minutes. The strips were then removed and immediately transferred to a new well containing 50 µL of the running buffer containing no antigen. This chase step was included to help reduce non-specific binding of the magnetic probes to the test line and to the membrane. After 10 more minutes, the strips were removed and allowed to dry for at least 1 hour before further analysis.

Figure 15:
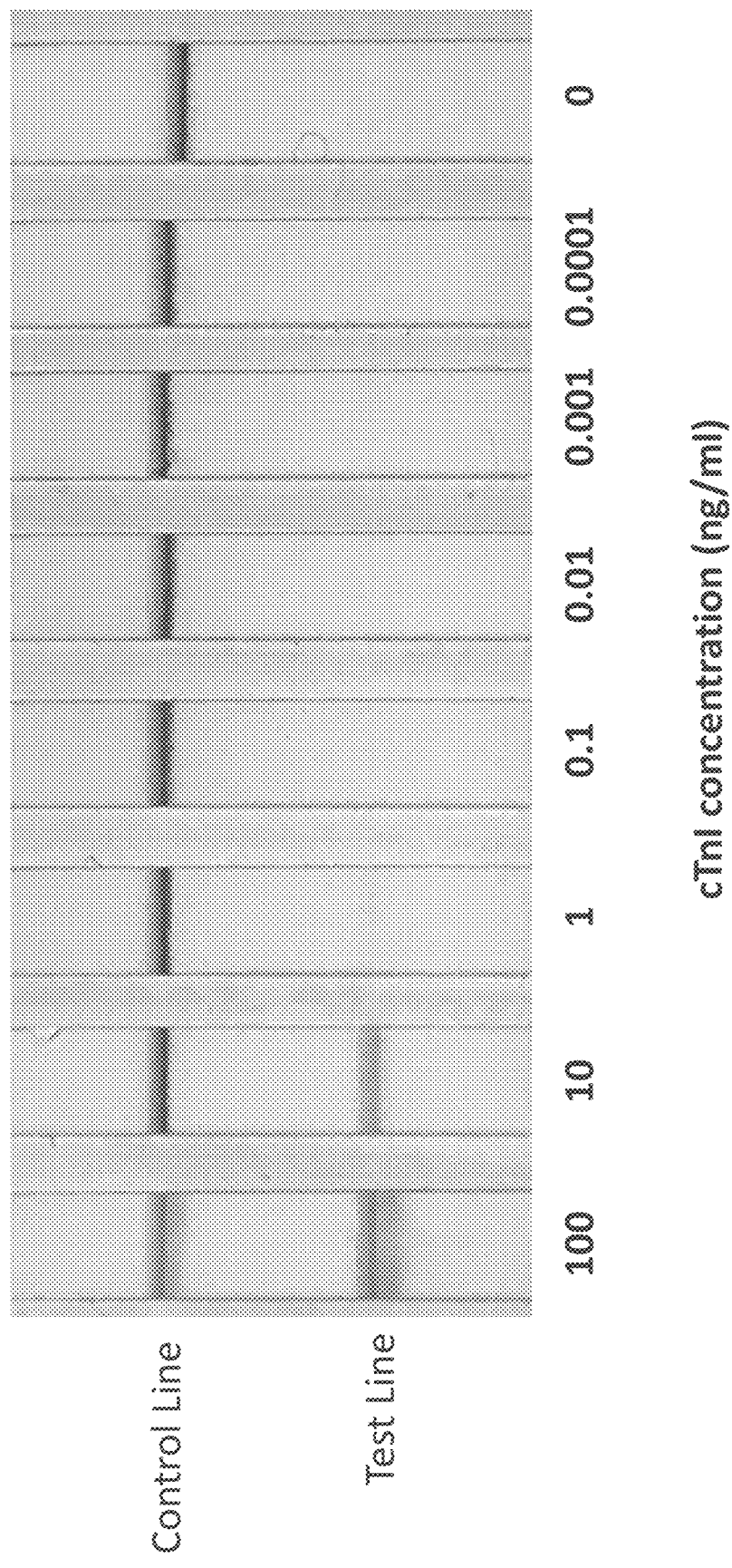
FIG. 15 illustrates a photograph of eight lateral flow strips of different cTnI concentrations.

FIG. 15 illustrates a photograph of the eight lateral flow strips of different cTnI concentrations. The line in the bottom half of the strip is the test line, and the line in the top half of the strip is the control line. The visibility of the test line is a quick measure of the presence and amount of cTnI antigen present in the sample. Visually, the test line can only be distinguished with the naked eye down to a concentration of 10 ng/mL.

The strips were each analyzed with both a standard colorimetric lateral flow reader and a system in accordance with certain implementations described herein. Each strip was measured once with the colorimetric reader. The strips were measured three times each with the system in accordance with certain implementations described herein and the signals were averaged at each cTnI concentration.

Figure 16B:
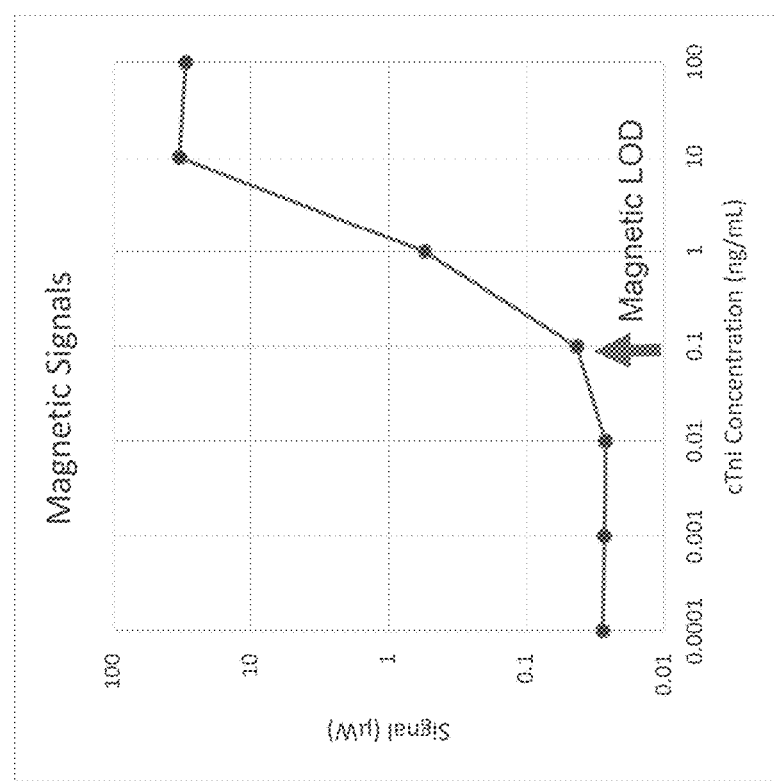
FIGS. 16A-16B show dose response curves produced using the standard colorimetric reader and the system in accordance with certain implementations described herein, respectively.
Figure 16A:
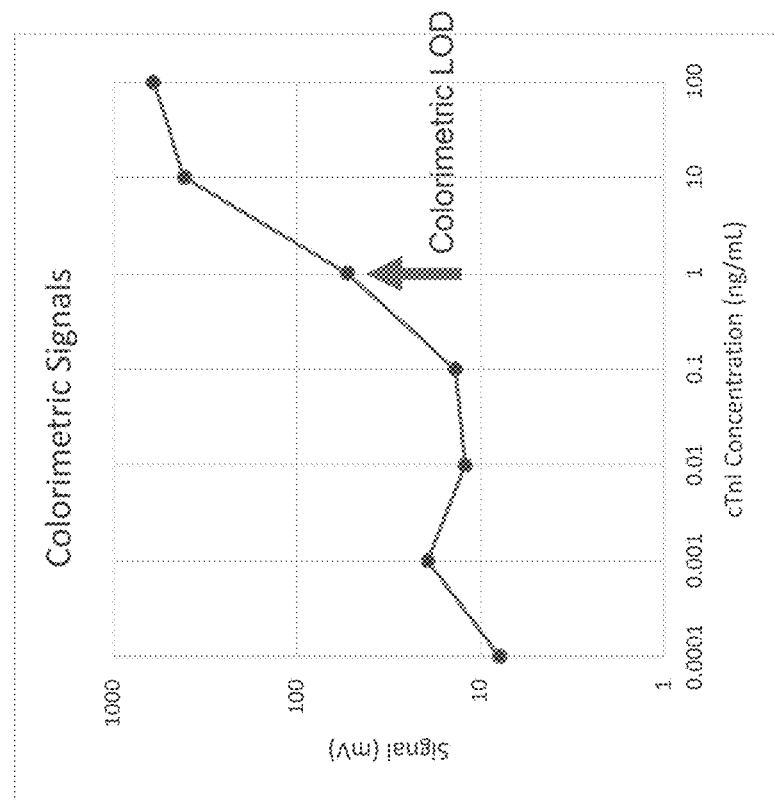

FIGS. 16A-16B show dose response curves produced using the standard colorimetric reader and the system in accordance with certain implementations described herein, respectively. The colorimetric reader has a limit of detection of 1 ng/mL for this system (see, FIG. 16A), as the signals for the lower concentrations are nearly equal to each other and quite close to the lower detection limit of the device, which varies between 0-15 mV when no line is visible. The relatively high signal at 0.001 ng/mL may have been caused by a scratch on the membrane surface, which cannot be easily distinguished from a test line signal using a colorimetric reader. One way in which the system in accordance with certain implementations described herein improves upon such conventional readers is that the magnetic signal intensity is not affected by such optical defects.

The limit of detection of this assay measured using the system in accordance with certain implementations described herein is 0.1 ng/mL, as shown in FIG. 16B. In order for a cTnI assay to be clinically relevant, the limit of detection can be on the order of 0.01 ng/mL. The assay results described herein do not meet this specification. However, the cTnI assay sensitivity is likely limited by the chemistry of the assay rather than by the detection capability of the system in accordance with certain implementations described herein. In FIG. 16B, the signal to noise ratio in the plateau region below 0.1 ng/ml is still greater than 20. This result implies that if the assay chemistry is improved (e.g., non-specific binding reduced and/or efficiency of cTnI binding to the nanoparticles or test line increased), the sensitivity of the assay can increase. Such improvements would not be available on the colorimetric reader, as the blank signal (9 mV) is already within the noise range of that reader (approximately 0-15 mV), and any optical imperfection such as scratch or stains would disrupt the color signal. Thus, the system in accordance with certain implementations described herein may allow for a greater improvement in sensitivity over the colorimetric reader, given more thorough development of the assay chemistry.

Example 3. Streptavidin/Biotin Assay

In Example 3, the system in accordance with certain implementations described herein was used in conjunction with half-strip lateral flow assays to evaluate the conjugation efficiency of streptavidin onto magnetic Au—Fe nanoparticles. The half-strip assays were produced using the same methods as described in Example 1, with only the composition and location of the capture zones differing. In this example, both the control line and test line included biotinylated bovine serum albumin (biotin-BSA), with the control line having a significantly higher concentration of biotin-BSA (0.5 mg/mL). The test line biotin-BSA concentration varied between 0.1-10 µg/mL. Biotin-BSA was chosen because of the strong binding interaction between biotin and streptavidin and the relatively higher molecular weight of BSA, which allows the molecule to bind more strongly to the nitrocellulose membrane. The control line and test line were approximately 6 mm apart.

The magnetic Au—Fe nanoparticles were conjugated with streptavidin in a similar method as in Examples 1 and 2. The conjugates were tested using lateral flow by mixing 5 µL of conjugates with 50 µL of running buffer (1×TBS+1%

Figure 17:
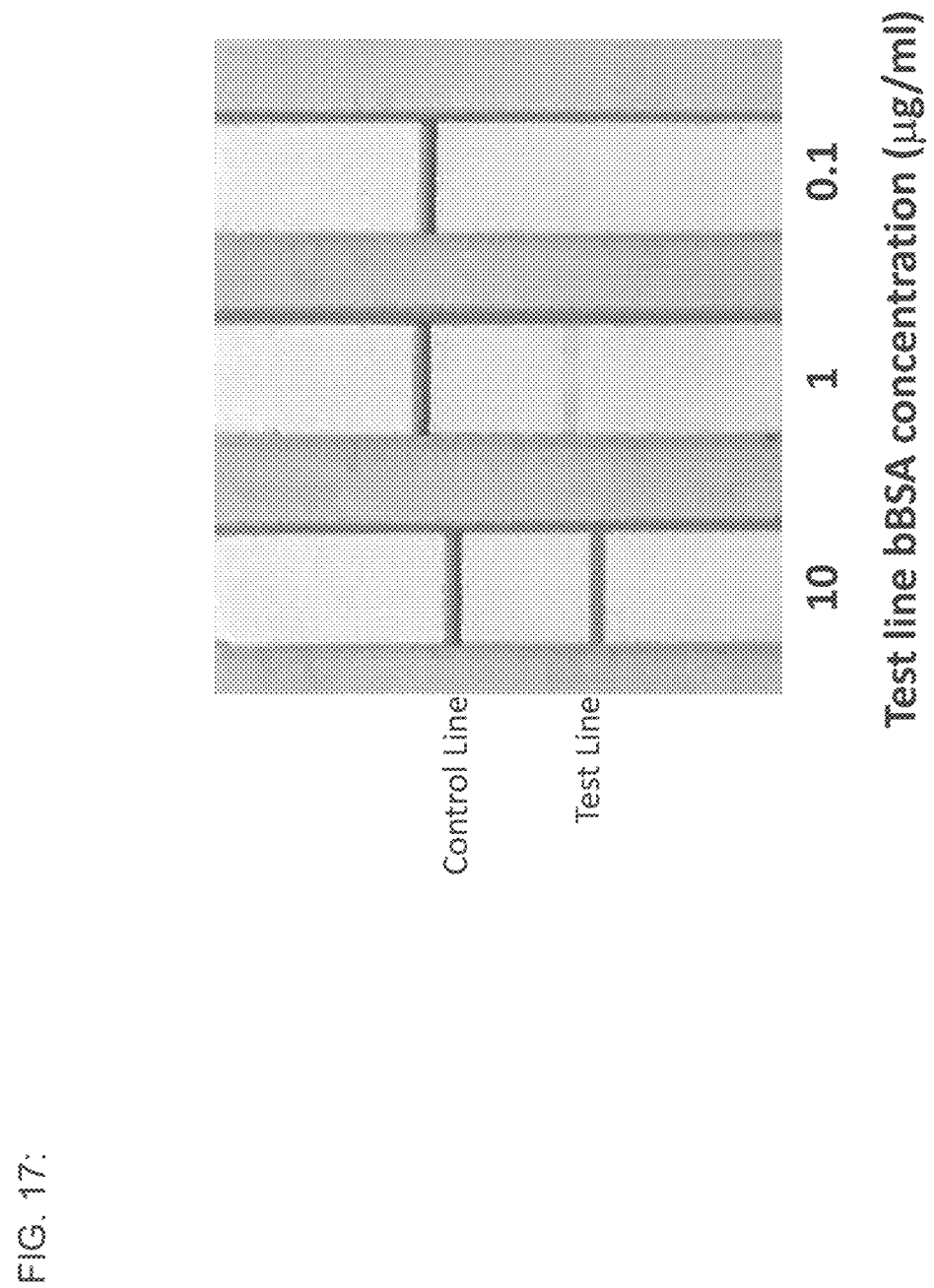
FIG. 17 illustrates a photograph of three representative strip at different biotin-BSA concentrations.

Tween-20) in one well of a 96-well plate, inserting the half-strip dipstick assay into it, and allowing capillary flow for 15 minutes. Three test line concentrations of biotin-BSA were each tested three times to establish reproducibility: 0.1, 1, and 10 µg/mL. FIG. 17 illustrates a photograph of three representative strip at different biotin-BSA concentrations. At 1 µg/mL the test line is barely visible to the naked eye, and at 0.1 µg/mL, the test line becomes invisible.

Figure 18A:
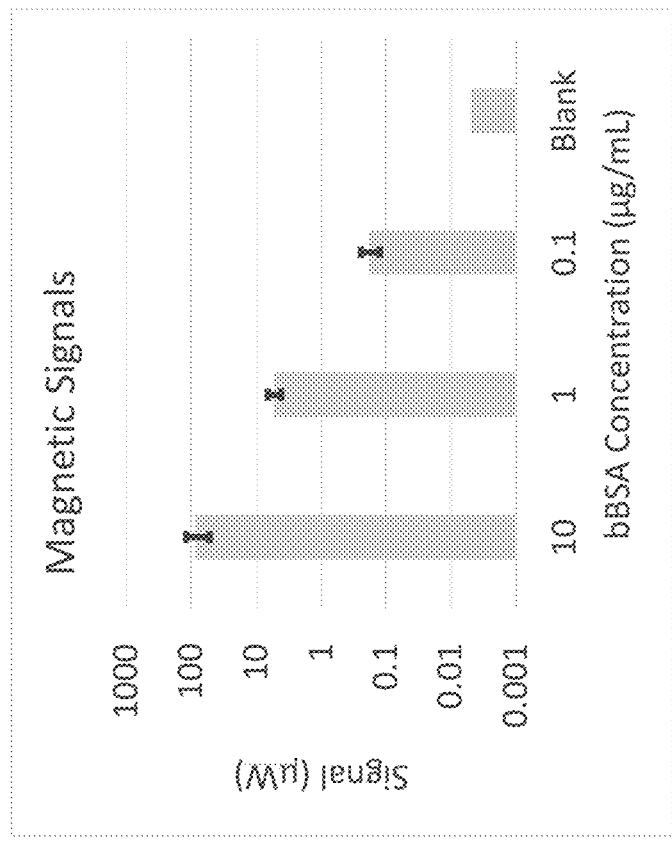
FIGS. 18A-18B illustrate the average magnetic and optical signals at each concentration, as well as the approximate average noise signal using the standard colorimetric reader and the system in accordance with certain implementations described herein, respectively.
Figure 18B:
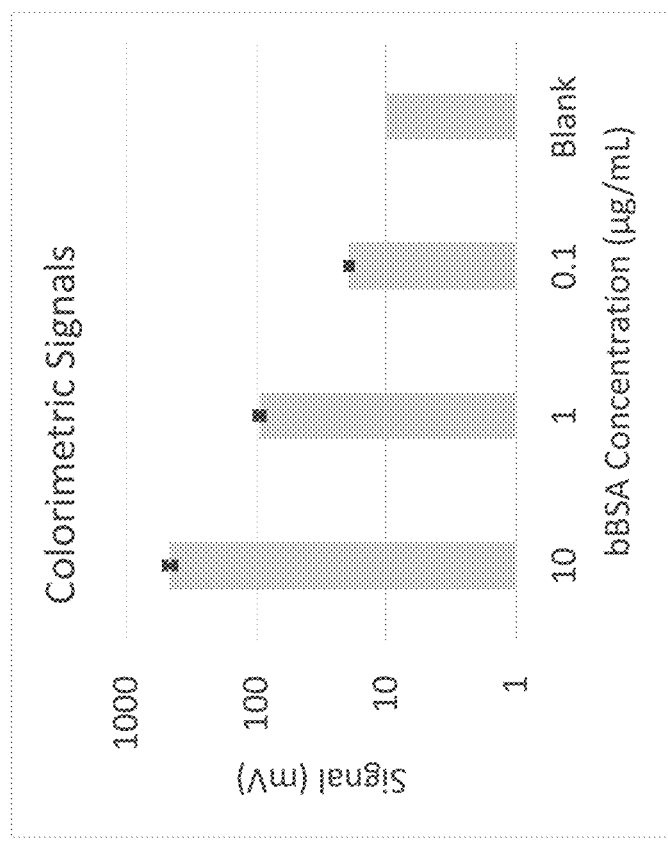

The nine lateral flow strips were measured using both a conventional colorimetric lateral flow reader and the system in accordance with certain implementations described herein. Each strip was measured three times with each device to establish the variation associated with each reader device. FIGS. 18A-18B illustrate the average magnetic and optical signals at each concentration, as well as the approximate average noise signal using the standard colorimetric reader and the system in accordance with certain implementations described herein, respectively. The system in accordance with certain implementations described herein had a broader dynamic range of signal of five orders of magnitude above the noise level, as compared to two orders of magnitude for the colorimetric system. In FIG. 18B, the signal-to-noise ratio of the magnetic signal at 0.1 µg/ml is greater than 20, while the signal-to-noise ratio for the colorimetric signal is about 2, which can be too low to be accepted for a valid measurement. While the test line of 0.1 µg/ml is barely above the detection limit of the colorimetric reader, as compared with a blank strip, the magnetic signal from the same test line is more than an order of magnitude stronger than the magnetic signal from the blank line, again proving the superior sensitivity of the system in accordance with certain implementations described herein.

FIGS. 19A-19B schematically illustrates an example voice coil linear actuator 200 and an example system 100 utilizing the voice coil linear actuator 200, respectively, in accordance with certain implementations described herein. The voice coil linear actuator 200 is configured to provide oscillational movement of the sample membrane 40 relative to the magnetic field sensor 20 of the apparatus 10 (e.g., in a y-direction substantially perpendicular to the control and test lines 42a, 42b, as shown in FIG. 19B).

The example voice coil linear actuator 200 schematically illustrated by FIG. 19A comprises a permanent magnet 202 extending within an electrically conductive coil 204 along an axial direction 206 of the coil 204. When an AC electrical current is applied to the coil 204, an oscillatory motion (e.g., back and forth) along the axial direction 206 of one or both of the magnet 202 and the coil 204 is generated in response to the electromotive force (EMF). In certain implementations, the coil 204 is fixed to a frame (not shown) and the magnet 202 is free to move in an oscillatory motion, while in certain other implementations, the magnet 202 is fixed to a frame (not shown) and the coil 204 is free to move in an oscillatory motion. In certain implementations, as compared with a piezo actuator, the voice coil linear actuator 200 advantageously provides (i) little or no mechanical hysteresis, (ii) higher operational frequencies (e.g., up to 100 Hz) and speeds (e.g., up to several hundred mm/s), and/or (iii) longer stroke lengths (e.g., up to several centimeters).

In certain implementations, the voice coil linear actuator 200 has a substantial stray magnetic field which can produce a strong background signal in the signal generated by the magnetic field sensor 20. In certain such implementations, the system 100 comprises magnetic shielding configured to reduce the portion of the stray magnetic field that affects the signal generated by the magnetic field sensor 20. For example, as schematically illustrated by FIG. 19B, the voice coil linear actuator 200 can comprise a magnetic shielding housing 210 at least partially containing the magnet 202 and the coil 204 and a shaft 220 in mechanical communication with the stage 50 and with the magnet 202 or the coil 204 that is configured to move. For example, the magnetic shielding housing 210 can comprise mu-metal (e.g., an alloy made of Ni and Fe configured to provide magnetic shielding) and the shaft 220 and the stage 50 can comprise non-magnetic materials (e.g., plastics). In certain implementations, the voice coil linear actuator 200 can be positioned to reduce or minimize the effects of the stray magnetic field on the signal generated by the magnetic field sensor 20. For example, axial positioning can help further avoid the stray magnetic fields since the magnetic fields are split into a left bunch and a right bunch, leaving the center area free of magnetic field.

Figure 20A:
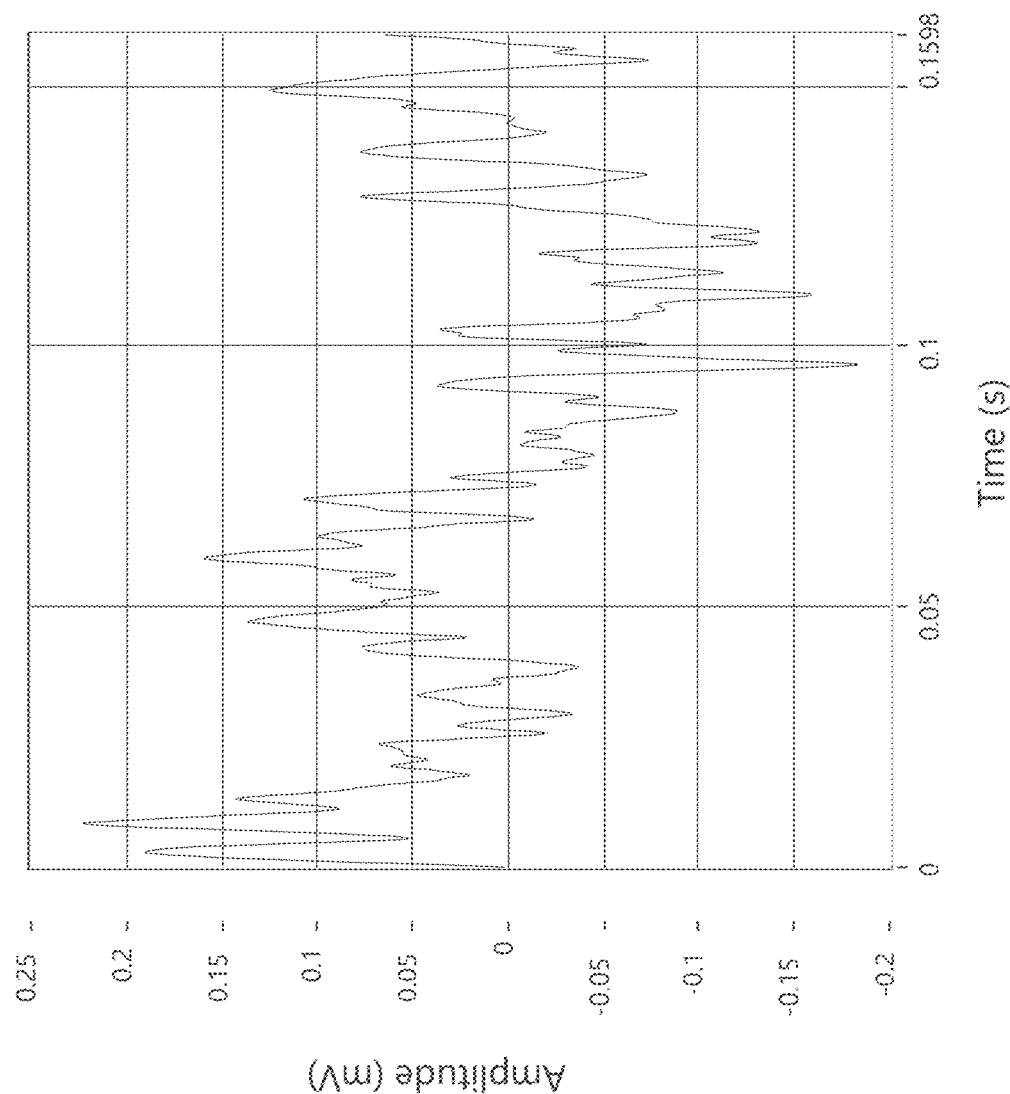
FIGS. 20A-20B show example plots of the time-averaged background noise on the MR sensor used with a voice coil linear actuator, magnetic shielding, and axial positioning in accordance with certain implementations described herein.
Figure 20B:
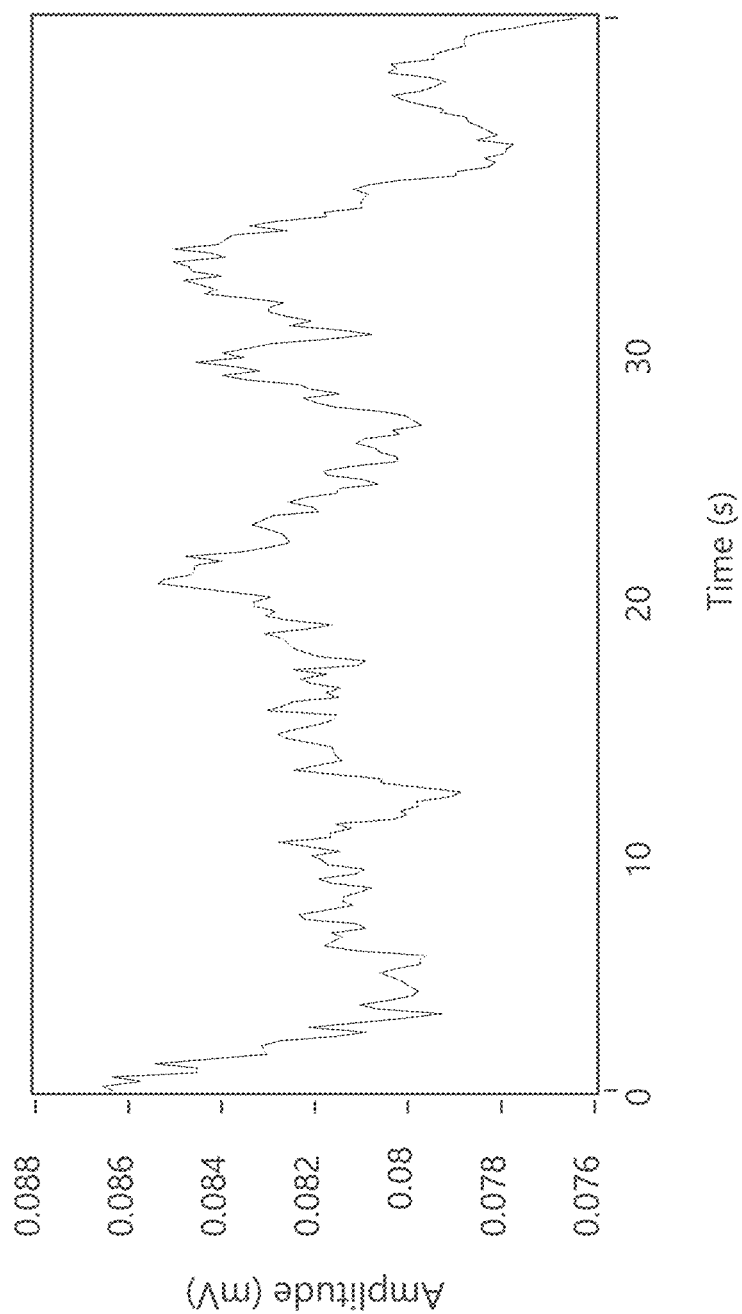

FIGS. 20A-20B show example plots of the time-averaged background noise on the magnetic field sensor 20 used with a voice coil linear actuator, magnetic shielding, and axial positioning in accordance with certain implementations described herein. FIG. 20A shows the background noise over relatively short time periods (e.g., less than 0.2 second) and FIG. 20B shows the background noise over relatively longer time periods (e.g., over hundreds of seconds). The relatively clean background signals shown in FIGS. 20A-20B illustrate the effectiveness of the mu-metal shielding and axial positioning. As seen in FIG. 20B, the time-averaged background noise level as an amplitude of about 0.08 mV, which is comparable to the noise level obtained with a piezo oscillation actuator (see, e.g., FIG. 8D).

Figure 21B:
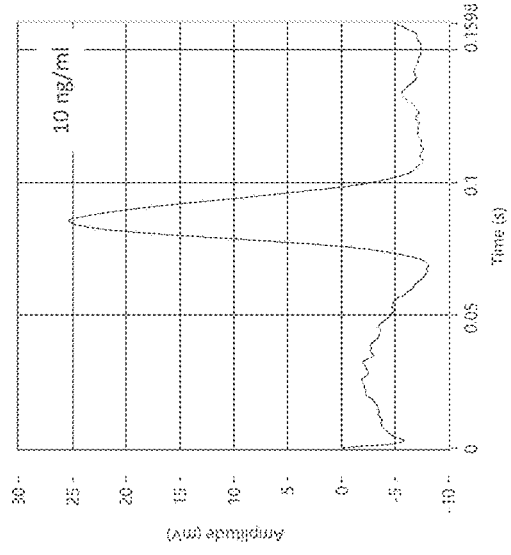
FIGS. 21A-21H show an example series of measurements of hCG assay taken using a voice coil linear actuator in accordance with certain implementations described herein.
Figure 21D:
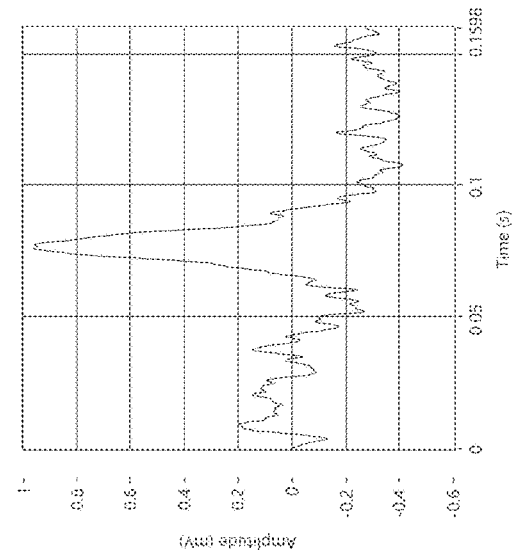
Figure 21A:
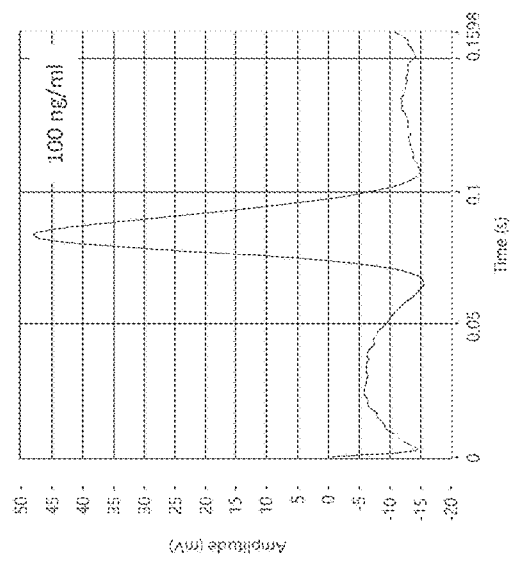
Figure 21C:
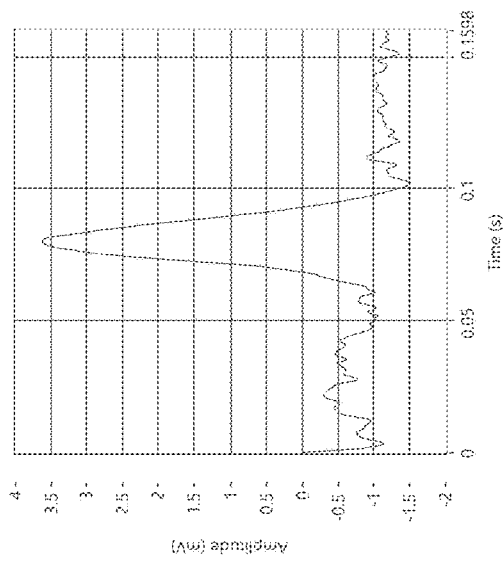
Figure 21E:
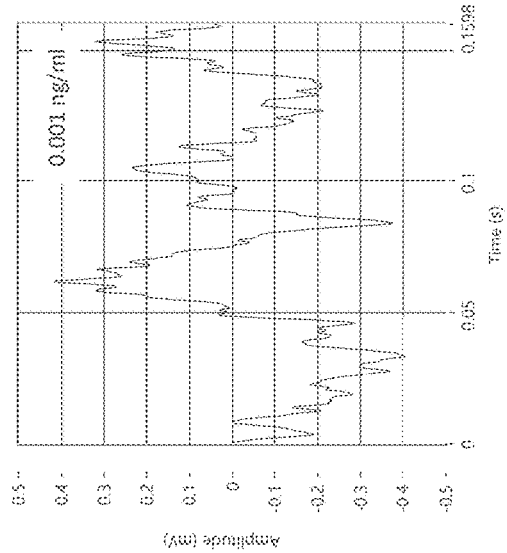
Figure 21F:
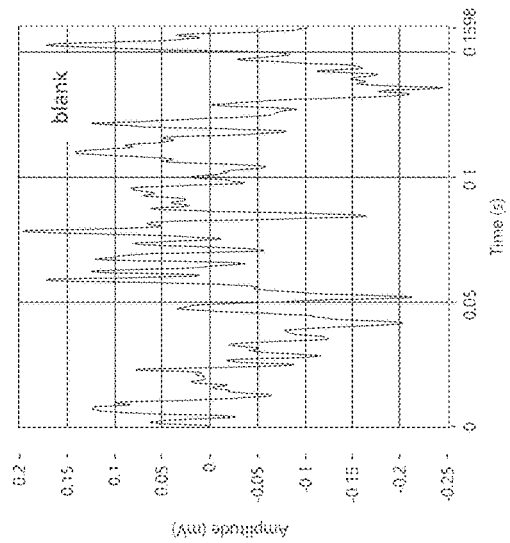
Figure 21G:
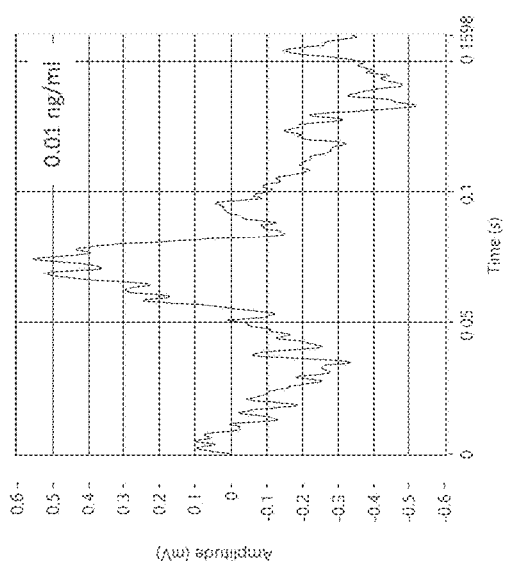
Figure 21H:
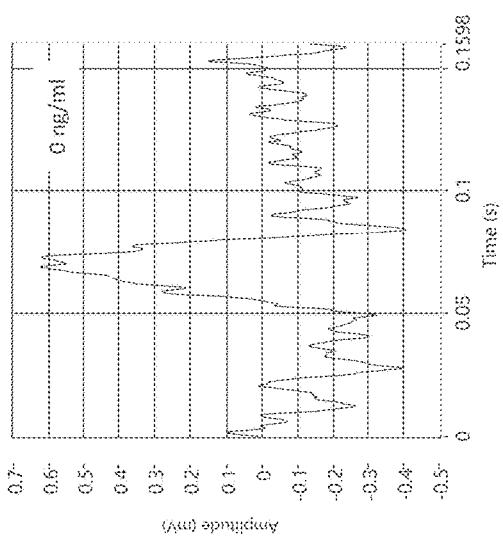

FIGS. 21A-21H show an example series of measurements using the voice coil linear actuator in accordance with certain implementations described herein. FIGS. 21A-21F show measurements of hCG assay membranes (e.g., fabricated as described in Example 1) with hCG concentrations from 100 ng/ml to 0.001 ng/ml in log 10 steps (see FIG. 13 for photographs of such hCG assay membranes). FIG. 21G shows a negative control and FIG. 21H shows a measurement with a blank membrane. These results have the same sensitivity as do the implementation using a piezo actuator.

Figure 22A:
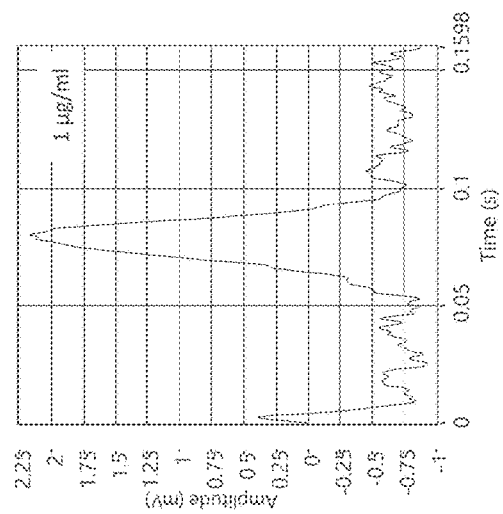
FIGS. 22A-22D show another example series of measurements of Streptavidin/Biotin assay membranes using the voice coil linear actuator in accordance with certain implementations described herein.
Figure 22B:
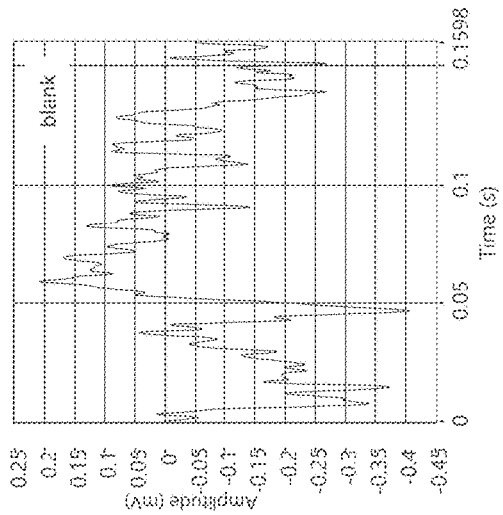
Figure 22C:
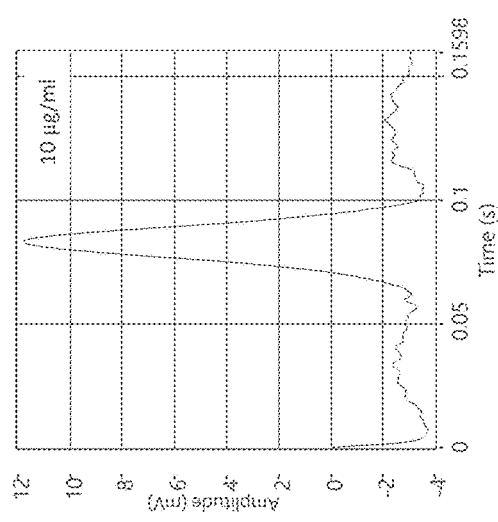
Figure 22D:
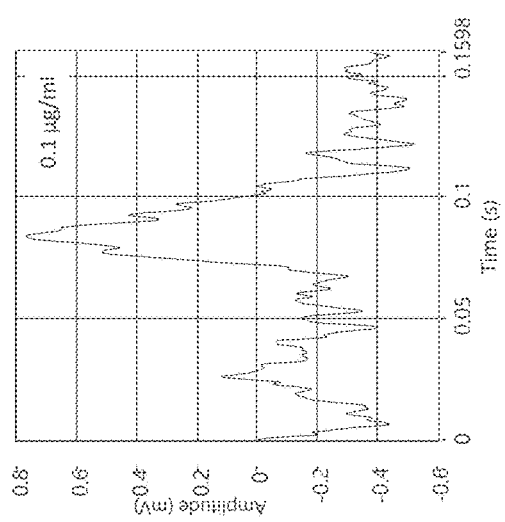

FIGS. 22A-22D show another example series of measurements of Streptavidin/Biotin assay membranes (e.g., fabricated as described in Example 3) using the voice coil linear actuator in accordance with certain implementations described herein. FIGS. 22A-22C show the measurements of Streptavidin/Biotin assay membranes with printed Biotin-BSA concentrations of 10 µg/ml, 1 µg/ml, 0.1 µg/ml, respectively, and FIG. 22D shows the measurements from a blank sample (e.g., 0 µg/ml). In particular, the clear detection of the 0.1 µg/ml sample, where the visual color of the test line diminishes (see FIG. 17 for photographs of such strips), demonstrates the superior sensitivity of the system 100 of certain implementations as compared with colorimetric detection.

Figure 23:
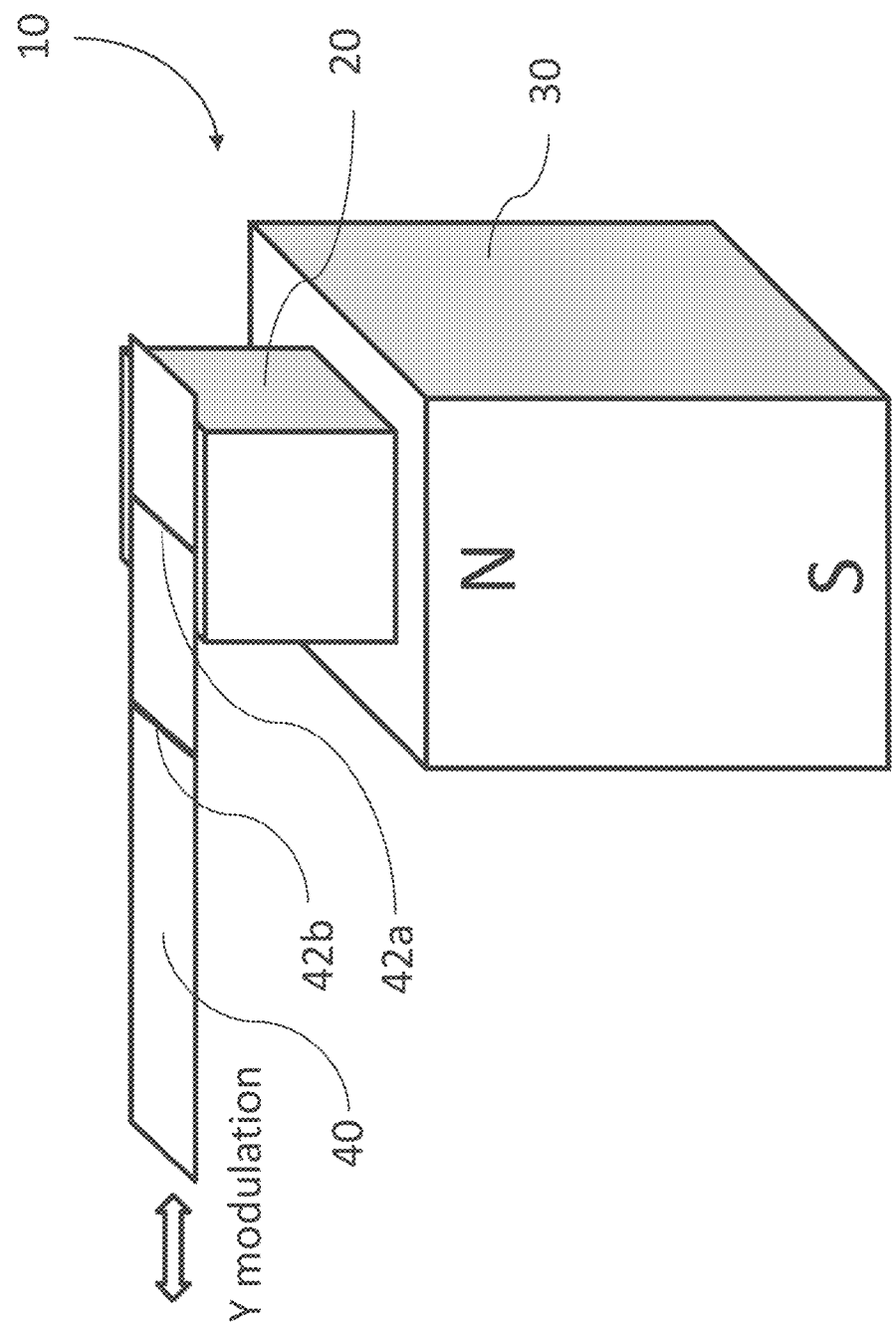
FIG. 23 schematically illustrates an example apparatus having the magnetic field sensor positioned beneath the membrane in accordance with certain implementations described herein.

FIG. 23 schematically illustrates an example apparatus 10 having the magnetic field sensor 20 positioned beneath the membrane 40 in accordance with certain implementations described herein. In certain implementations, this arrangement advantageously simplifies the lateral flow cassette design such that the top of the membrane 40 can be exposed for simultaneous visual examination and optical (colorimetric) detection. Although the thickness of the membrane 40 (e.g., typically between 0.1 mm-0.5 mm) reduces the signal intensity at the magnetic field sensor 20 positioned beneath the membrane 40, the apparatus 10 still exhibits sufficient sensitivity.

FIGS. 24A-24D show example measurements using a magnetic field sensor 20 positioned beneath a series of membranes 40 in accordance with certain implementations described herein. The membranes 40 of FIGS. 24A-24D are the same series of Streptavidin/Biotin assay membranes that were measured in FIGS. 22A-22D with the magnetic field sensor 20 positioned above the membrane 40. The visually invisible 0.1 µg/ml test line is still detectable, as shown in FIG. 24C, again demonstrating the high sensitivity of certain such implementations.

Example, non-limiting experimental data are included herein to illustrate results achievable by various implementations of the systems and methods described herein. All ranges of data and all values within such ranges of data that are shown in the figures or described in the specification are expressly included in this disclosure. The example experiments, experimental data, tables, graphs, plots, figures, and processing and/or operating parameters (e.g., values and/or ranges) described herein are intended to be illustrative of operating conditions of the disclosed systems and methods and are not intended to limit the scope of the operating conditions for various implementations of the methods and systems disclosed herein. Additionally, the experiments, experimental data, calculated data, tables, graphs, plots, figures, and other data disclosed herein demonstrate various regimes in which implementations of the disclosed systems and methods may operate effectively to produce one or more desired results. Such operating regimes and desired results are not limited solely to specific values of operating parameters, conditions, or results shown, for example, in a table, graph, plot, or figure, but also include suitable ranges including or spanning these specific values. Accordingly, the values disclosed herein include the range of values between any of the values listed or shown in the tables, graphs, plots, figures, etc. Additionally, the values disclosed herein include the range of values above or below any of the values listed or shown in the tables, graphs, plots, figures, etc. as might be demonstrated by other values listed or shown in the tables, graphs, plots, figures, etc. Also, although the data disclosed herein may establish one or more effective operating ranges and/or one or more desired results for certain implementations, it is to be understood that not every implementation need be operable in each such operating range or need produce each such desired result. Further, other implementations of the disclosed systems and methods may operate in other operating regimes and/or produce other results than shown and described with reference to the example experiments, experimental data, tables, graphs, plots, figures, and other data herein.

The invention has been described in several non-limiting implementations. It is to be understood that the implementations are not mutually exclusive, and elements described in connection with one implementation may be combined with, rearranged, or eliminated from, other implementations in suitable ways to accomplish desired design objectives. No single feature or group of features is necessary or required for each implementation.

For purposes of summarizing the present invention, certain aspects, advantages and novel features of the present invention are described herein. It is to be understood, however, that not necessarily all such advantages may be achieved in accordance with any particular implementation. Thus, the present invention may be embodied or carried out in a manner that achieves one or more advantages without necessarily achieving other advantages as may be taught or suggested herein.

As used herein any reference to "one implementation" or "some implementations" or "an implementation" means that a particular element, feature, structure, or characteristic described in connection with the implementation is included in at least one implementation. The appearances of the phrase "in one implementation" in various places in the specification are not necessarily all referring to the same implementation. Conditional language used herein, such as, among others, "can," "could," "might," "may," "e.g.," and the like, unless specifically stated otherwise, or otherwise understood within the context as used, is generally intended to convey that certain implementations include, while other implementations do not include, certain features, elements and/or steps. In addition, the articles "a" or "an" or "the" as used in this application and the appended claims are to be construed to mean "one or more" or "at least one" unless specified otherwise.

As used herein, the terms "comprises," "comprising," "includes," "including," "has," "having" or any other variation thereof, are open-ended terms and intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), or both A and B are true (or present). As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain implementations require at least one of X, at least one of Y, and at least one of Z to each be present.

Thus, while only certain implementations have been specifically described herein, it will be apparent that numerous modifications may be made thereto without departing from the spirit and scope of the invention. Further, acronyms are used merely to enhance the readability of the specification and claims. It should be noted that these acronyms are not intended to lessen the generality of the terms used and they should not be construed to restrict the scope of the claims to the implementations described therein.

What is claimed is:

1. A system comprising:
   an apparatus comprising:
   at least one permanent magnet; and
   at least one magnetic field sensor at a pole of the at least one permanent magnet and configured to be positioned relative to a surface of a membrane containing immobilized magnetic particles selectively bound to an analyte such that the magnetic particles are magnetized by the at least one permanent magnet;
   a stage mechanically coupled to at least one of the apparatus and the membrane, the stage configured to move at least one of the apparatus and the membrane relative to one another with an oscillatory movement along a first direction parallel to the surface of the membrane;

at least one controller configured to control the oscillatory movement of the stage and to generate first synchronization trigger signals indicative of the oscillatory movement; and a data acquisition unit configured to receive sensor signals from the at least one magnetic field sensor and the first synchronization trigger signals from the at least one controller.

2. The system of claim 1, wherein the stage comprises a linear motion sub-stage configured to move at least one of the apparatus and the membrane relative to one another with a linear mechanical movement in a second direction parallel to the surface of the membrane, the second direction perpendicular to the first direction, the at least one controller further configured to control the movement of the sub-stage along the second direction and to generate second synchronization trigger signals indicative of the linear mechanical movement, the data acquisition unit further configured to receive the second synchronization trigger signals from the at least one controller.

3. The system of claim 1, wherein the stage comprises at least one piezoelectric actuator and/or at least one voice coil actuator.

4. The system of claim 1, wherein the at least one magnetic field sensor comprises at least one magnetoresistance (MR) sensor.

5. The system of claim 4, wherein the at least one MR sensor comprises a Wheatstone bridge comprising four individual MR sensors.

6. The system of claim 1, wherein the oscillatory movement has a frequency in a range of 1 Hz to 100 Hz and an amplitude in a range of 0.1 mm to 10 mm.

7. The system of claim 6, wherein the oscillatory movement is generated by a piezoelectric actuator and/or a voice coil actuator.

8. The system of claim 1, wherein the magnetic particles are superparamagnetic, ferromagnetic, or have another form of magnetism such that the magnetic particles are configured to generate a magnetic induction upon magnetization by a magnetic field.

9. The system of claim 1, wherein the membrane contains a two-dimensional array of dots comprising deposited binding molecules, each dot having a different capture molecule reacting to a different analyte.

10. The system of claim 1, wherein the membrane comprises paper, glass, metal, and/or semiconductor.

11. The system of claim 1, wherein said at least one magnetic field sensor comprises a magnetoresistance sensor attached to the pole of said at least one permanent magnet and the sensor signals are acquired and averaged over time in synchronization with said oscillatory movement, said time acquisition and averaging being triggered by said first synchronization trigger signals.

12. The system according to claim 11,
wherein said membrane is transported along a second direction parallel to the surface of the membrane and perpendicular to said first direction, forming a two dimensional scanning motion substantially parallel to the surface of the membrane,
where second synchronization trigger signals are generated in synchronization with said two dimensional scanning motion along the second direction,
wherein said sensor signals are acquired in synchronization of said two dimensional scanning motion, and provide two dimensional distribution of signal substantially parallel to the surface of the membrane.

13. The system according to claim 11, further comprising a pressure sensor below said membrane or a container holding the membrane, the pressure sensor configured to monitor a contact between the membrane and the magnetoresistance sensor.

14. The system according to claim 13, wherein a third motion is provided to said membrane or to said magnetoresistance sensor, the third motion in a direction perpendicular to the surface of the membrane to adjust a distance between said membrane and said magnetoresistance sensor, said third motion is controlled by feedback signal from said pressure sensor.

15. The system according to claim 11, wherein the stage comprises a linear motion stage and/or a rotational motion stage configured to position said membrane.

16. The system according to claim 11, further comprising an optical camera positioned above the membrane and configured to record images and measure color intensity of said magnetic particles, whereby the concentration of analyte is obtained.

17. The system of claim 1, wherein the membrane comprises a lateral flow membrane containing the immobilized magnetic particles.

* * * * *

UNITED STATES PATENT AND TRADEMARK OFFICE
CERTIFICATE OF CORRECTION

| | | |
|---|---|---|
| PATENT NO. | : 11,885,800 B2 | Page 1 of 1 |
| APPLICATION NO. | : 17/037162 | |
| DATED | : January 30, 2024 | |
| INVENTOR(S) | : Bing Liu | |

It is certified that error appears in the above-identified patent and that said Letters Patent is hereby corrected as shown below:

In the Specification

In Column 22, Line 39, delete "ρW)." and insert --μW).--.

In Column 22, Line 42, delete "ρW)" and insert --μW)--.

Signed and Sealed this
Fourth Day of June, 2024

Katherine Kelly Vidal
*Director of the United States Patent and Trademark Office*